(12) United States Patent
Brock et al.

(10) Patent No.: US 10,329,621 B2
(45) Date of Patent: Jun. 25, 2019

(54) DNA METHYLATION MARKERS AND METHODS OF USE

(71) Applicant: The Johns Hopkins University, Baltimore, MD (US)

(72) Inventors: Malcolm V. Brock, Owings Mills, MD (US); Stephen B. Baylin, Baltimore, MD (US); James G. Herman, Lutherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/181,121

(22) Filed: Feb. 14, 2014

(65) Prior Publication Data

US 2015/0031022 A1    Jan. 29, 2015

Related U.S. Application Data

(63) Continuation of application No. 12/515,735, filed as application No. PCT/US2007/024308 on Nov. 20, 2007, now abandoned.

(60) Provisional application No. 60/860,196, filed on Nov. 20, 2006.

(51) Int. Cl.
  *C07H 21/04* (2006.01)
  *C12Q 1/68* (2018.01)
  *C12Q 1/6886* (2018.01)

(52) U.S. Cl.
  CPC ...... *C12Q 1/6886* (2013.01); *C12Q 2600/112* (2013.01); *C12Q 2600/118* (2013.01); *C12Q 2600/154* (2013.01); *C12Q 2600/16* (2013.01)

(58) Field of Classification Search
  None
  See application file for complete search history.

(56) References Cited

U.S. PATENT DOCUMENTS

| | | | |
|---|---|---|---|
| 5,856,094 | A | 1/1999 | Sidransky et al. |
| 6,756,200 | B2 | 6/2004 | Sukumar et al. |
| 7,563,567 | B1 | 7/2009 | Huang et al. |
| 2003/0224040 | A1 | 12/2003 | Baylin et al. |
| 2006/0051768 | A1 | 3/2006 | Hoon et al. |

FOREIGN PATENT DOCUMENTS

| WO | 2002-044331 A2 | 6/2002 |
|---|---|---|
| WO | 2005/042713 A2 | 5/2005 |

OTHER PUBLICATIONS

Toyooka (Mol Cancer Ther 2001 vol. 1 pp. 61-67).*
Duffy (European Journal of Cancer 2009 pp. 335-346).*
Feng (PNAS 2010 vol. 107 No. 19 pp. 8689-8694).*
Michels (Experimental Gerontology 2010 vol. 45 pp. 297-301).*
Lo (Cancer Research 59 pp. 3899-3903 Aug. 15, 1999).*
Momparler (Lung Cancer 34 2001 S111-S115).*
Tang Moying et al: "Wnt signaling promoter hypermethylation distinguishes lung primary adenocarcinomas from colorectal metastasis to the lung" vol. 119, No. 11, Dec. 2006 (Dec. 2006), pp. 2603-2606.
Kohonen-Corish Maija R J et al: "Promoter hypermethylation of the 0-6-methylguanine DNA methyltransferase gene and microsatellite instability in metastatic melanoma" Journal of Investigative Dermatology, vol. 126, No. 1, Jan. 2006 (Jan. 2006), pp. 167-171.
Ebert Matthias P A et al: "Hypermethylation of the TPEF/HPP1 gene in primary and metastatic colorectal cancers" Neoplasia (New York), vol. 7, No. 8, Aug. 2005 (Aug. 2005), pp. 771-778.
Yegnasubramanian Srinivasan et al: "Hypermethylation of CpG islands in primary and metastatic human prostate cancer." Cancer Research, vol. 64, No. 6, Mar. 15, 2004 (Mar. 15, 2004), pp. 1975-1986.
Takashi Arai er al: "Associationof GSTP1 CpG Islands Hypermethylation with Poor Prognosis in Human Breast Cancers" Breast Cancer Research and Treatment, Kluwer Academic Publishers, BO, vol. 100, No. 2, Jun. 22, 2006 (Jun. 22, 2006), pp. 169-176.
Chang et al. "Loss of E-cadherin expression resulting from promoter hypermethylation in oral tongue carcinoma and its prognostic significance", Cancer, vol. 94, No. 2, Jan. 15, 2002, pp. 386-392.
Kim JS, "Aberrant methylation of H-cadherin (CDH13) promoter is associated with tumor progression in primary nonsmall cell lung carcinoma." Cancer. Nov. 1, 2005;104(9):1825-33.
Toyooka KO, et al. "Loss of expression and aberrant methylation of the CDH13 (H-cadherin) gene in breast and lung carcinomas." Cancer Res. Jun. 1, 2001;61(11):4556-60.
Liu, Y. et al. "Hypermethylation of p16INK4a in chinese lung cancer patients: biological and clinical implications", Carcinogenesis, vol. 24, No. 12, Jan. 1, 2003, pp. 1897-1907.
Nakata Shoji et al. "The methylation status and protein expression of CDH1, p16(INK4A), and fragile histidine triad in nonsmall cell lung carcinoma—Epigenetic silencing, clinical features, and prognostic signficance", Cancer, vol. 106, No. 10, May 2006, pp. 2190-2199.
Harden Susan V. et al. "Gene promoter hypermethylation in tumors and lymph nodes of stage I lung cancer patients.". Clinical Cancer Research: An Official Journal of the American Association for Cancer Research APR 2003 LNKD-PUBMNED 12684406, vol. 9, No. 4, Apr. 2003, pp. 1370-1375.
Zochbauer-Muller S et al. "Aberrant promoter methylation of multiple genes in non-small cell lung cancers", Cancer Research, American Association for Cancer Research, US, vol. 61, No. 1, Jan. 1, 2001, pp. 249-255.

(Continued)

*Primary Examiner* — Jeanine A Goldberg
(74) *Attorney, Agent, or Firm* — Mintz Levin Cohn Ferris Glovsky and Popeo, P.C.; Peter F. Corless

(57) ABSTRACT

The present invention provides methods for identifying metastases by detecting nucleic acid hypermethylation of one or more genes in one or more samples, and in particular in the lymph nodes. The invention further relates to DNA methylation as a predictor of disease recurrence and patient prognosis, specifically in the field of cancer biology.

4 Claims, 8 Drawing Sheets
Specification includes a Sequence Listing.

(56) References Cited

OTHER PUBLICATIONS

Esteller M. et al. "Detection of aberrant promoter hypermethylation of tumor suppressor genes in serum DNA from non-small cell lung patients", Cancer Research, American Association for Cancer Research, US, vol. 59, Jan. 1, 1999, pp. 67-70.
Feng, Suhua et al. Conservation and divergence of methylation patterning in plants and animals. PNAS 2010 vol. 107 No. 19, pp. 8689-8694.
Toyooka, Shinichi et al. DNA methylation Profiles of Lung Tumors. Molecular Cancer Therapeutics Nov. 2001 vol. 1 pp. 61-67.
International Search Report, International Application No. PCT/US2007/024308 dated Aug. 25, 2008 and dated Sep. 30, 2008.
Sanchez-Cespedes et al., Clinical Cancer Research, V. 5, pp. 2450-2454, 1999.

\* cited by examiner

SEQUENCE LISTING

<160> NUMBER OF SEQ ID NOS: 7

<210> SEQ ID NO 1
<211> LENGTH: 713
<212> TYPE: PRT
<213> ORGANISM: Homo sapiens

<400> SEQUENCE: 1

```
Met Gln Pro Arg Thr Pro Leu Val Leu Cys Val Leu Leu Ser Gln Val
1               5                   10                  15

Leu Leu Leu Thr Ser Ala Glu Asp Leu Asp Cys Thr Pro Gly Phe Gln
                20                  25                  30

Gln Lys Val Phe His Ile Asn Gln Pro Ala Glu Phe Ile Glu Asp Gln
            35                  40                  45

Ser Ile Leu Asn Leu Thr Phe Ser Asp Cys Lys Gly Asn Asp Lys Leu
50                  55                  60

Arg Tyr Glu Val Ser Ser Pro Tyr Phe Lys Val Asn Ser Asp Gly Gly
65                  70                  75                  80

Leu Val Ala Leu Arg Asn Ile Thr Ala Val Gly Lys Thr Leu Phe Val
                85                  90                  95

His Ala Arg Thr Pro His Ala Glu Asp Met Ala Glu Leu Val Ile Val
            100                 105                 110

Gly Gly Lys Asp Ile Gln Gly Ser Leu Gln Asp Ile Phe Lys Phe Ala
        115                 120                 125

Arg Thr Ser Pro Val Pro Arg Gln Lys Arg Ser Ile Val Val Ser Pro
    130                 135                 140

Ile Leu Ile Pro Glu Asn Gln Arg Gln Pro Phe Pro Arg Asp Val Gly
145                 150                 155                 160

Lys Val Val Asp Ser Asp Arg Pro Glu Arg Ser Lys Phe Arg Leu Thr
                165                 170                 175

Gly Lys Gly Val Asp Gln Glu Pro Lys Gly Ile Phe Arg Ile Asn Glu
            180                 185                 190

Asn Thr Gly Ser Val Ser Val Thr Arg Thr Leu Asp Arg Glu Val Ile
        195                 200                 205

Ala Val Tyr Gln Leu Phe Val Glu Thr Thr Asp Val Asn Gly Lys Thr
    210                 215                 220

Leu Glu Gly Pro Val Pro Leu Glu Val Ile Ile Asp Gln Asn Asp
225                 230                 235                 240

Asn Arg Pro Ile Phe Arg Glu Gly Pro Tyr Ile Gly His Val Met Glu
                245                 250                 255

Gly Ser Pro Thr Gly Thr Thr Val Met Arg Met Thr Ala Phe Asp Ala
            260                 265                 270
```

```
Asp Asp Pro Ala Thr Asp Asn Ala Leu Leu Arg Tyr Asn Ile Arg Gln
            275                 280                 285

Gln Thr Pro Asp Lys Pro Ser Pro Asn Met Phe Tyr Ile Asp Pro Glu
        290                 295                 300

Lys Gly Asp Ile Val Thr Val Ser Pro Ala Leu Leu Asp Arg Glu
305                 310                 315                 320

Thr Leu Glu Asn Pro Lys Tyr Glu Leu Ile Ile Glu Ala Gln Asp Met
                325                 330                 335

Ala Gly Leu Asp Val Gly Leu Thr Gly Thr Ala Thr Ala Thr Ile Met
            340                 345                 350

Ile Asp Asp Lys Asn Asp His Ser Pro Lys Phe Thr Lys Lys Glu Phe
            355                 360                 365

Gln Ala Thr Val Glu Glu Gly Ala Val Gly Val Ile Val Asn Leu Thr
        370                 375                 380

Val Glu Asp Lys Asp Asp Pro Thr Thr Gly Ala Trp Arg Ala Ala Tyr
385                 390                 395                 400

Thr Ile Ile Asn Gly Asn Pro Gly Gln Ser Phe Glu Ile His Thr Asn
                405                 410                 415

Pro Gln Thr Asn Glu Gly Met Leu Ser Val Val Lys Pro Leu Asp Tyr
            420                 425                 430

Glu Ile Ser Ala Phe His Thr Leu Leu Ile Lys Val Glu Asn Glu Asp
        435                 440                 445

Pro Leu Val Pro Asp Val Ser Tyr Gly Pro Ser Ser Thr Ala Thr Val
            450                 455                 460

His Ile Thr Val Leu Asp Val Asn Glu Gly Pro Val Phe Tyr Pro Asp
465                 470                 475                 480

Pro Met Met Val Thr Arg Gln Glu Asp Leu Ser Val Gly Ser Val Leu
                485                 490                 495

Leu Thr Val Asn Ala Thr Asp Pro Asp Ser Leu Gln His Gln Thr Ile
            500                 505                 510

Arg Tyr Ser Val Tyr Lys Asp Pro Ala Gly Trp Leu Asn Ile Asn Pro
        515                 520                 525

Ile Asn Gly Thr Val Asp Thr Thr Ala Val Leu Asp Arg Glu Ser Pro
            530                 535                 540

Phe Val Asp Asn Ser Val Tyr Thr Ala Leu Phe Leu Ala Ile Asp Ser
545                 550                 555                 560

Gly Asn Pro Pro Ala Thr Gly Thr Gly Thr Leu Leu Ile Thr Leu Glu
                565                 570                 575

Asp Val Asn Asp Asn Ala Pro Phe Ile Tyr Pro Thr Val Ala Glu Val
            580                 585                 590

Cys Asp Asp Ala Lys Asn Leu Ser Val Val Ile Leu Gly Ala Ser Asp
        595                 600                 605

Lys Asp Leu His Pro Asn Thr Asp Pro Phe Lys Phe Glu Ile His Lys
    610                 615                 620

Gln Ala Val Pro Asp Lys Val Trp Lys Ile Ser Lys Ile Asn Asn Thr
625                 630                 635                 640

His Ala Leu Val Ser Leu Leu Gln Asn Leu Asn Lys Ala Asn Tyr Asn
                645                 650                 655

Leu Pro Ile Met Val Thr Asp Ser Gly Lys Pro Pro Met Thr Asn Ile
            660                 665                 670

Thr Asp Leu Arg Val Gln Val Cys Ser Cys Arg Asn Ser Lys Val Asp
        675                 680                 685

Cys Asn Ala Ala Gly Ala Leu Arg Phe Ser Leu Pro Ser Val Leu Leu
```

```
                690                 695                 700

Leu Ser Leu Phe Ser Leu Ala Cys Leu
705                 710

<210> SEQ ID NO 2
<211> LENGTH: 182
<212> TYPE: PRT
<213> ORGANISM: Homo sapiens

<400> SEQUENCE: 2

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr Asp Arg Val Asp Leu Gly Thr
65                  70                  75                  80

Leu Arg Gly Tyr Tyr Asn Gln Ser Glu Ala Gly Ser His Thr Ile Gln
                85                  90                  95

Met Met Tyr Gly Cys Asp Val Gly Pro Asp Gly Arg Leu Leu Arg Gly
            100                 105                 110

Tyr Gln Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr
            180

<210> SEQ ID NO 3
<211> LENGTH: 2843
<212> TYPE: PRT
<213> ORGANISM: Homo sapiens

<400> SEQUENCE: 3

Met Ala Ala Ala Ser Tyr Asp Gln Leu Leu Lys Gln Val Glu Ala Leu
1               5                   10                  15

Lys Met Glu Asn Ser Asn Leu Arg Gln Glu Leu Glu Asp Asn Ser Asn
            20                  25                  30

His Leu Thr Lys Leu Glu Thr Glu Ala Ser Asn Met Lys Glu Val Leu
        35                  40                  45

Lys Gln Leu Gln Gly Ser Ile Glu Asp Glu Ala Met Ala Ser Ser Gly
    50                  55                  60

Gln Ile Asp Leu Leu Glu Arg Leu Lys Glu Leu Asn Leu Asp Ser Ser
65                  70                  75                  80

Asn Phe Pro Gly Val Lys Leu Arg Ser Lys Met Ser Leu Arg Ser Tyr
                85                  90                  95

Gly Ser Arg Glu Gly Ser Val Ser Ser Arg Ser Gly Glu Cys Ser Pro
            100                 105                 110

Val Pro Met Gly Ser Phe Pro Arg Arg Gly Phe Val Asn Gly Ser Arg
```

-continued

```
            115                 120                 125
Glu Ser Thr Gly Tyr Leu Glu Glu Leu Glu Lys Glu Arg Ser Leu Leu
    130                 135                 140

Leu Ala Asp Leu Asp Lys Glu Lys Glu Lys Asp Trp Tyr Tyr Ala
145                 150                 155                 160

Gln Leu Gln Asn Leu Thr Lys Arg Ile Asp Ser Leu Pro Leu Thr Glu
                165                 170                 175

Asn Phe Ser Leu Gln Thr Asp Met Thr Arg Arg Gln Leu Glu Tyr Glu
                180                 185                 190

Ala Arg Gln Ile Arg Val Ala Met Glu Glu Gln Leu Gly Thr Cys Gln
                195                 200                 205

Asp Met Glu Lys Arg Ala Gln Arg Arg Ile Ala Arg Ile Gln Gln Ile
    210                 215                 220

Glu Lys Asp Ile Leu Arg Ile Arg Gln Leu Leu Gln Ser Gln Ala Thr
225                 230                 235                 240

Glu Ala Glu Arg Ser Ser Gln Asn Lys His Glu Thr Gly Ser His Asp
                245                 250                 255

Ala Glu Arg Gln Asn Glu Gly Gln Gly Val Gly Glu Ile Asn Met Ala
                260                 265                 270

Thr Ser Gly Asn Gly Gln Gly Ser Thr Thr Arg Met Asp His Glu Thr
                275                 280                 285

Ala Ser Val Leu Ser Ser Ser Thr His Ser Ala Pro Arg Arg Leu
    290                 295                 300

Thr Ser His Leu Gly Thr Lys Val Glu Met Val Tyr Ser Leu Leu Ser
305                 310                 315                 320

Met Leu Gly Thr His Asp Lys Asp Asp Met Ser Arg Thr Leu Leu Ala
                325                 330                 335

Met Ser Ser Gln Asp Ser Cys Ile Ser Met Arg Gln Ser Gly Cys
                340                 345                 350

Leu Pro Leu Leu Ile Gln Leu Leu His Gly Asn Asp Lys Asp Ser Val
                355                 360                 365

Leu Leu Gly Asn Ser Arg Gly Ser Lys Glu Ala Arg Ala Arg Ala Ser
    370                 375                 380

Ala Ala Leu His Asn Ile Ile His Ser Gln Pro Asp Asp Lys Arg Gly
385                 390                 395                 400

Arg Arg Glu Ile Arg Val Leu His Leu Leu Glu Gln Ile Arg Ala Tyr
                405                 410                 415

Cys Glu Thr Cys Trp Glu Trp Gln Glu Ala His Glu Pro Gly Met Asp
                420                 425                 430

Gln Asp Lys Asn Pro Met Pro Ala Pro Val Glu His Gln Ile Cys Pro
    435                 440                 445

Ala Val Cys Val Leu Met Lys Leu Ser Phe Asp Glu Glu His Arg His
                450                 455                 460

Ala Met Asn Glu Leu Gly Gly Leu Gln Ala Ile Ala Glu Leu Leu Gln
465                 470                 475                 480

Val Asp Cys Glu Met Tyr Gly Leu Thr Asn Asp His Tyr Ser Ile Thr
                485                 490                 495

Leu Arg Arg Tyr Ala Gly Met Ala Leu Thr Asn Leu Thr Phe Gly Asp
                500                 505                 510

Val Ala Asn Lys Ala Thr Leu Cys Ser Met Lys Gly Cys Met Arg Ala
                515                 520                 525

Leu Val Ala Gln Leu Lys Ser Glu Ser Glu Asp Leu Gln Gln Val Ile
    530                 535                 540
```

```
Ala Ser Val Leu Arg Asn Leu Ser Trp Arg Ala Asp Val Asn Ser Lys
545                 550                 555                 560

Lys Thr Leu Arg Glu Val Gly Ser Val Lys Ala Leu Met Glu Cys Ala
            565                 570                 575

Leu Glu Val Lys Lys Glu Ser Thr Leu Lys Ser Val Leu Ser Ala Leu
        580                 585                 590

Trp Asn Leu Ser Ala His Cys Thr Glu Asn Lys Ala Asp Ile Cys Ala
    595                 600                 605

Val Asp Gly Ala Leu Ala Phe Leu Val Gly Thr Leu Thr Tyr Arg Ser
610                 615                 620

Gln Thr Asn Thr Leu Ala Ile Ile Glu Ser Gly Gly Ile Leu Arg
625                 630                 635                 640

Asn Val Ser Ser Leu Ile Ala Thr Asn Glu Asp His Arg Gln Ile Leu
                645                 650                 655

Arg Glu Asn Asn Cys Leu Gln Thr Leu Leu Gln His Leu Lys Ser His
            660                 665                 670

Ser Leu Thr Ile Val Ser Asn Ala Cys Gly Thr Leu Trp Asn Leu Ser
        675                 680                 685

Ala Arg Asn Pro Lys Asp Gln Glu Ala Leu Trp Asp Met Gly Ala Val
    690                 695                 700

Ser Met Leu Lys Asn Leu Ile His Ser Lys His Lys Met Ile Ala Met
705                 710                 715                 720

Gly Ser Ala Ala Ala Leu Arg Asn Leu Met Ala Asn Arg Pro Ala Lys
                725                 730                 735

Tyr Lys Asp Ala Asn Ile Met Ser Pro Gly Ser Ser Leu Pro Ser Leu
            740                 745                 750

His Val Arg Lys Gln Lys Ala Leu Glu Ala Glu Leu Asp Ala Gln His
        755                 760                 765

Leu Ser Glu Thr Phe Asp Asn Ile Asp Asn Leu Ser Pro Lys Ala Ser
    770                 775                 780

His Arg Ser Lys Gln Arg His Lys Gln Ser Leu Tyr Gly Asp Tyr Val
785                 790                 795                 800

Phe Asp Thr Asn Arg His Asp Asp Asn Arg Ser Asp Asn Phe Asn Thr
                805                 810                 815

Gly Asn Met Thr Val Leu Ser Pro Tyr Leu Asn Thr Thr Val Leu Pro
            820                 825                 830

Ser Ser Ser Ser Ser Arg Gly Ser Leu Asp Ser Ser Arg Ser Glu Lys
        835                 840                 845

Asp Arg Ser Leu Glu Arg Glu Arg Gly Ile Gly Leu Gly Asn Tyr His
    850                 855                 860

Pro Ala Thr Glu Asn Pro Gly Thr Ser Ser Lys Arg Gly Leu Gln Ile
865                 870                 875                 880

Ser Thr Thr Ala Ala Gln Ile Ala Lys Val Met Glu Glu Val Ser Ala
                885                 890                 895

Ile His Thr Ser Gln Glu Asp Arg Ser Ser Gly Ser Thr Thr Glu Leu
            900                 905                 910

His Cys Val Thr Asp Glu Arg Asn Ala Leu Arg Arg Ser Ser Ala Ala
        915                 920                 925

His Thr His Ser Asn Thr Tyr Asn Phe Thr Lys Ser Glu Asn Ser Asn
    930                 935                 940

Arg Thr Cys Ser Met Pro Tyr Ala Lys Leu Glu Tyr Lys Arg Ser Ser
945                 950                 955                 960
```

```
Asn Asp Ser Leu Asn Ser Val Ser Ser Asp Gly Tyr Gly Lys Arg
                965                 970                 975

Gly Gln Met Lys Pro Ser Ile Glu Ser Tyr Ser Glu Asp Asp Glu Ser
            980                 985                 990

Lys Phe Cys Ser Tyr Gly Gln Tyr Pro Ala Asp Leu Ala His Lys Ile
        995                1000                1005

His Ser Ala Asn His Met Asp Asp Asn Asp Gly Glu Leu Asp Thr
    1010                1015                1020

Pro Ile Asn Tyr Ser Leu Lys Tyr Ser Asp Glu Gln Leu Asn Ser
    1025                1030                1035

Gly Arg Gln Ser Pro Ser Gln Asn Glu Arg Trp Ala Arg Pro Lys
    1040                1045                1050

His Ile Ile Glu Asp Glu Ile Lys Gln Ser Glu Gln Arg Gln Ser
    1055                1060                1065

Arg Asn Gln Ser Thr Thr Tyr Pro Val Tyr Thr Glu Ser Thr Asp
    1070                1075                1080

Asp Lys His Leu Lys Phe Gln Pro His Phe Gly Gln Gln Glu Cys
    1085                1090                1095

Val Ser Pro Tyr Arg Ser Arg Gly Ala Asn Gly Ser Glu Thr Asn
    1100                1105                1110

Arg Val Gly Ser Asn His Gly Ile Asn Gln Asn Val Ser Gln Ser
    1115                1120                1125

Leu Cys Gln Glu Asp Asp Tyr Glu Asp Asp Lys Pro Thr Asn Tyr
    1130                1135                1140

Ser Glu Arg Tyr Ser Glu Glu Glu Gln His Glu Glu Glu Arg
    1145                1150                1155

Pro Thr Asn Tyr Ser Ile Lys Tyr Asn Glu Glu Lys Arg His Val
    1160                1165                1170

Asp Gln Pro Ile Asp Tyr Ser Leu Lys Tyr Ala Thr Asp Ile Pro
    1175                1180                1185

Ser Ser Gln Lys Gln Ser Phe Ser Phe Ser Lys Ser Ser Ser Gly
    1190                1195                1200

Gln Ser Ser Lys Thr Glu His Met Ser Ser Ser Ser Glu Asn Thr
    1205                1210                1215

Ser Thr Pro Ser Ser Asn Ala Lys Arg Gln Asn Gln Leu His Pro
    1220                1225                1230

Ser Ser Ala Gln Ser Arg Ser Gly Gln Pro Gln Lys Ala Ala Thr
    1235                1240                1245

Cys Lys Val Ser Ser Ile Asn Gln Glu Thr Ile Gln Thr Tyr Cys
    1250                1255                1260

Val Glu Asp Thr Pro Ile Cys Phe Ser Arg Cys Ser Ser Leu Ser
    1265                1270                1275

Ser Leu Ser Ser Ala Glu Asp Glu Ile Gly Cys Asn Gln Thr Thr
    1280                1285                1290

Gln Glu Ala Asp Ser Ala Asn Thr Leu Gln Ile Ala Glu Ile Lys
    1295                1300                1305

Glu Lys Ile Gly Thr Arg Ser Ala Glu Asp Pro Val Ser Glu Val
    1310                1315                1320

Pro Ala Val Ser Gln His Pro Arg Thr Lys Ser Ser Arg Leu Gln
    1325                1330                1335

Gly Ser Ser Leu Ser Ser Glu Ser Ala Arg His Lys Ala Val Glu
    1340                1345                1350

Phe Ser Ser Gly Ala Lys Ser Pro Ser Lys Ser Gly Ala Gln Thr
```

-continued

```
            1355                1360                1365
Pro Lys Ser Pro Pro Glu His Tyr Val Gln Thr Pro Leu Met
        1370                1375                1380
Phe Ser Arg Cys Thr Ser Val Ser Ser Leu Asp Ser Phe Glu Ser
        1385                1390                1395
Arg Ser Ile Ala Ser Ser Val Gln Ser Glu Pro Cys Ser Gly Met
        1400                1405                1410
Val Ser Gly Ile Ile Ser Pro Ser Asp Leu Pro Asp Ser Pro Gly
        1415                1420                1425
Gln Thr Met Pro Pro Ser Arg Ser Lys Thr Pro Pro Pro Pro
        1430                1435                1440
Gln Thr Ala Gln Thr Lys Arg Glu Val Pro Lys Asn Lys Ala Pro
        1445                1450                1455
Thr Ala Glu Lys Arg Glu Ser Gly Pro Lys Gln Ala Ala Val Asn
        1460                1465                1470
Ala Ala Val Gln Arg Val Gln Val Leu Pro Asp Ala Asp Thr Leu
        1475                1480                1485
Leu His Phe Ala Thr Glu Ser Thr Pro Asp Gly Phe Ser Cys Ser
        1490                1495                1500
Ser Ser Leu Ser Ala Leu Ser Leu Asp Glu Pro Phe Ile Gln Lys
        1505                1510                1515
Asp Val Glu Leu Arg Ile Met Pro Pro Val Gln Glu Asn Asp Asn
        1520                1525                1530
Gly Asn Glu Thr Glu Ser Glu Gln Pro Lys Glu Ser Asn Glu Asn
        1535                1540                1545
Gln Glu Lys Glu Ala Glu Lys Thr Ile Asp Ser Glu Lys Asp Leu
        1550                1555                1560
Leu Asp Asp Ser Asp Asp Asp Ile Glu Ile Leu Glu Glu Cys
        1565                1570                1575
Ile Ile Ser Ala Met Pro Thr Lys Ser Ser Arg Lys Ala Lys Lys
        1580                1585                1590
Pro Ala Gln Thr Ala Ser Lys Leu Pro Pro Val Ala Arg Lys
        1595                1600                1605
Pro Ser Gln Leu Pro Val Tyr Lys Leu Leu Pro Ser Gln Asn Arg
        1610                1615                1620
Leu Gln Pro Gln Lys His Val Ser Phe Thr Pro Gly Asp Asp Met
        1625                1630                1635
Pro Arg Val Tyr Cys Val Glu Gly Thr Pro Ile Asn Phe Ser Thr
        1640                1645                1650
Ala Thr Ser Leu Ser Asp Leu Thr Ile Glu Ser Pro Pro Asn Glu
        1655                1660                1665
Leu Ala Ala Gly Glu Gly Val Arg Gly Gly Ala Gln Ser Gly Glu
        1670                1675                1680
Phe Glu Lys Arg Asp Thr Ile Pro Thr Glu Gly Arg Ser Thr Asp
        1685                1690                1695
Glu Ala Gln Gly Gly Lys Thr Ser Ser Val Thr Ile Pro Glu Leu
        1700                1705                1710
Asp Asp Asn Lys Ala Glu Glu Gly Asp Ile Leu Ala Glu Cys Ile
        1715                1720                1725
Asn Ser Ala Met Pro Lys Gly Lys Ser His Lys Pro Phe Arg Val
        1730                1735                1740
Lys Lys Ile Met Asp Gln Val Gln Gln Ala Ser Ala Ser Ser Ser
        1745                1750                1755
```

```
Ala Pro Asn Lys Asn Gln Leu Asp Gly Lys Lys Lys Pro Thr
    1760            1765            1770

Ser Pro Val Lys Pro Ile Pro Gln Asn Thr Glu Tyr Arg Thr Arg
    1775            1780            1785

Val Arg Lys Asn Ala Asp Ser Lys Asn Asn Leu Asn Ala Glu Arg
    1790            1795            1800

Val Phe Ser Asp Asn Lys Asp Ser Lys Lys Gln Asn Leu Lys Asn
    1805            1810            1815

Asn Ser Lys Val Phe Asn Asp Lys Leu Pro Asn Asn Glu Asp Arg
    1820            1825            1830

Val Arg Gly Ser Phe Ala Phe Asp Ser Pro His His Tyr Thr Pro
    1835            1840            1845

Ile Glu Gly Thr Pro Tyr Cys Phe Ser Arg Asn Asp Ser Leu Ser
    1850            1855            1860

Ser Leu Asp Phe Asp Asp Asp Val Asp Leu Ser Arg Glu Lys
    1865            1870            1875

Ala Glu Leu Arg Lys Ala Lys Glu Asn Lys Glu Ser Glu Ala Lys
    1880            1885            1890

Val Thr Ser His Thr Glu Leu Thr Ser Asn Gln Gln Ser Ala Asn
    1895            1900            1905

Lys Thr Gln Ala Ile Ala Lys Gln Pro Ile Asn Arg Gly Gln Pro
    1910            1915            1920

Lys Pro Ile Leu Gln Lys Gln Ser Thr Phe Pro Gln Ser Ser Lys
    1925            1930            1935

Asp Ile Pro Asp Arg Gly Ala Ala Thr Asp Glu Lys Leu Gln Asn
    1940            1945            1950

Phe Ala Ile Glu Asn Thr Pro Val Cys Phe Ser His Asn Ser Ser
    1955            1960            1965

Leu Ser Ser Leu Ser Asp Ile Asp Gln Glu Asn Asn Asn Lys Glu
    1970            1975            1980

Asn Glu Pro Ile Lys Glu Thr Glu Pro Pro Asp Ser Gln Gly Glu
    1985            1990            1995

Pro Ser Lys Pro Gln Ala Ser Gly Tyr Ala Pro Lys Ser Phe His
    2000            2005            2010

Val Glu Asp Thr Pro Val Cys Phe Ser Arg Asn Ser Ser Leu Ser
    2015            2020            2025

Ser Leu Ser Ile Asp Ser Glu Asp Asp Leu Leu Gln Glu Cys Ile
    2030            2035            2040

Ser Ser Ala Met Pro Lys Lys Lys Lys Pro Ser Arg Leu Lys Gly
    2045            2050            2055

Asp Asn Glu Lys His Ser Pro Arg Asn Met Gly Gly Ile Leu Gly
    2060            2065            2070

Glu Asp Leu Thr Leu Asp Leu Lys Asp Ile Gln Arg Pro Asp Ser
    2075            2080            2085

Glu His Gly Leu Ser Pro Asp Ser Glu Asn Phe Asp Trp Lys Ala
    2090            2095            2100

Ile Gln Glu Gly Ala Asn Ser Ile Val Ser Ser Leu His Gln Ala
    2105            2110            2115

Ala Ala Ala Ala Cys Leu Ser Arg Gln Ala Ser Ser Asp Ser Asp
    2120            2125            2130

Ser Ile Leu Ser Leu Lys Ser Gly Ile Ser Leu Gly Ser Pro Phe
    2135            2140            2145
```

```
His Leu Thr Pro Asp Gln Glu Glu Lys Pro Phe Thr Ser Asn Lys
2150                2155                2160

Gly Pro Arg Ile Leu Lys Pro Gly Glu Lys Ser Thr Leu Glu Thr
2165                2170                2175

Lys Lys Ile Glu Ser Glu Ser Lys Gly Ile Lys Gly Gly Lys Lys
2180                2185                2190

Val Tyr Lys Ser Leu Ile Thr Gly Lys Val Arg Ser Asn Ser Glu
2195                2200                2205

Ile Ser Gly Gln Met Lys Gln Pro Leu Gln Ala Asn Met Pro Ser
2210                2215                2220

Ile Ser Arg Gly Arg Thr Met Ile His Ile Pro Gly Val Arg Asn
2225                2230                2235

Ser Ser Ser Ser Thr Ser Pro Val Ser Lys Lys Gly Pro Pro Leu
2240                2245                2250

Lys Thr Pro Ala Ser Lys Ser Pro Ser Glu Gly Gln Thr Ala Thr
2255                2260                2265

Thr Ser Pro Arg Gly Ala Lys Pro Ser Val Lys Ser Glu Leu Ser
2270                2275                2280

Pro Val Ala Arg Gln Thr Ser Gln Ile Gly Gly Ser Ser Lys Ala
2285                2290                2295

Pro Ser Arg Ser Gly Ser Arg Asp Ser Thr Pro Ser Arg Pro Ala
2300                2305                2310

Gln Gln Pro Leu Ser Arg Pro Ile Gln Ser Pro Gly Arg Asn Ser
2315                2320                2325

Ile Ser Pro Gly Arg Asn Gly Ile Ser Pro Pro Asn Lys Leu Ser
2330                2335                2340

Gln Leu Pro Arg Thr Ser Ser Pro Ser Thr Ala Ser Thr Lys Ser
2345                2350                2355

Ser Gly Ser Gly Lys Met Ser Tyr Thr Ser Pro Gly Arg Gln Met
2360                2365                2370

Ser Gln Gln Asn Leu Thr Lys Gln Thr Gly Leu Ser Lys Asn Ala
2375                2380                2385

Ser Ser Ile Pro Arg Ser Glu Ser Ala Ser Lys Gly Leu Asn Gln
2390                2395                2400

Met Asn Asn Gly Asn Gly Ala Asn Lys Lys Val Glu Leu Ser Arg
2405                2410                2415

Met Ser Ser Thr Lys Ser Ser Gly Ser Glu Ser Asp Arg Ser Glu
2420                2425                2430

Arg Pro Val Leu Val Arg Gln Ser Thr Phe Ile Lys Glu Ala Pro
2435                2440                2445

Ser Pro Thr Leu Arg Arg Lys Leu Glu Glu Ser Ala Ser Phe Glu
2450                2455                2460

Ser Leu Ser Pro Ser Ser Arg Pro Ala Ser Pro Thr Arg Ser Gln
2465                2470                2475

Ala Gln Thr Pro Val Leu Ser Pro Ser Leu Pro Asp Met Ser Leu
2480                2485                2490

Ser Thr His Ser Ser Val Gln Ala Gly Gly Trp Arg Lys Leu Pro
2495                2500                2505

Pro Asn Leu Ser Pro Thr Ile Glu Tyr Asn Asp Gly Arg Pro Ala
2510                2515                2520

Lys Arg His Asp Ile Ala Arg Ser His Ser Glu Ser Pro Ser Arg
2525                2530                2535

Leu Pro Ile Asn Arg Ser Gly Thr Trp Lys Arg Glu His Ser Lys
```

```
                    2540                2545                2550

His Ser Ser Ser Leu Pro Arg Val Ser Thr Trp Arg Arg Thr Gly
    2555                2560                2565

Ser Ser Ser Ser Ile Leu Ser Ala Ser Ser Glu Ser Ser Glu Lys
    2570                2575                2580

Ala Lys Ser Glu Asp Glu Lys His Val Asn Ser Ile Ser Gly Thr
    2585                2590                2595

Lys Gln Ser Lys Glu Asn Gln Val Ser Ala Lys Gly Thr Trp Arg
    2600                2605                2610

Lys Ile Lys Glu Asn Glu Phe Ser Pro Thr Asn Ser Thr Ser Gln
    2615                2620                2625

Thr Val Ser Ser Gly Ala Thr Asn Gly Ala Glu Ser Lys Thr Leu
    2630                2635                2640

Ile Tyr Gln Met Ala Pro Ala Val Ser Lys Thr Glu Asp Val Trp
    2645                2650                2655

Val Arg Ile Glu Asp Cys Pro Ile Asn Asn Pro Arg Ser Gly Arg
    2660                2665                2670

Ser Pro Thr Gly Asn Thr Pro Pro Val Ile Asp Ser Val Ser Glu
    2675                2680                2685

Lys Ala Asn Pro Asn Ile Lys Asp Ser Lys Asp Asn Gln Ala Lys
    2690                2695                2700

Gln Asn Val Gly Asn Gly Ser Val Pro Met Arg Thr Val Gly Leu
    2705                2710                2715

Glu Asn Arg Leu Asn Ser Phe Ile Gln Val Asp Ala Pro Asp Gln
    2720                2725                2730

Lys Gly Thr Glu Ile Lys Pro Gly Gln Asn Asn Pro Val Pro Val
    2735                2740                2745

Ser Glu Thr Asn Glu Ser Ser Ile Val Glu Arg Thr Pro Phe Ser
    2750                2755                2760

Ser Ser Ser Ser Ser Lys His Ser Ser Pro Ser Gly Thr Val Ala
    2765                2770                2775

Ala Arg Val Thr Pro Phe Asn Tyr Asn Pro Ser Pro Arg Lys Ser
    2780                2785                2790

Ser Ala Asp Ser Thr Ser Ala Arg Pro Ser Gln Ile Pro Thr Pro
    2795                2800                2805

Val Asn Asn Asn Thr Lys Lys Arg Asp Ser Lys Thr Asp Ser Thr
    2810                2815                2820

Glu Ser Ser Gly Thr Gln Ser Pro Lys Arg His Ser Gly Ser Tyr
    2825                2830                2835

Leu Val Thr Ser Val
    2840

<210> SEQ ID NO 4
<211> LENGTH: 340
<212> TYPE: PRT
<213> ORGANISM: Homo sapiens

<400> SEQUENCE: 4

Met Ser Gly Glu Pro Glu Leu Ile Glu Leu Arg Glu Leu Ala Pro
1               5                   10                  15

Gly Arg Ala Gly Lys Gly Arg Thr Arg Leu Glu Arg Ala Asn Ala Leu
                20                  25                  30

Arg Ile Ala Arg Gly Thr Ala Cys Asn Pro Thr Arg Gln Leu Val Pro
    35                  40                  45
```

```
Gly Arg Gly His Arg Phe Gln Pro Ala Gly Pro Ala Thr His Thr Trp
    50                  55                  60
Cys Asp Leu Cys Gly Asp Phe Ile Trp Gly Val Val Arg Lys Gly Leu
65                  70                  75                  80
Gln Cys Ala His Cys Lys Phe Thr Cys His Tyr Arg Cys Arg Ala Leu
                85                  90                  95
Val Cys Leu Asp Cys Cys Gly Pro Arg Asp Leu Gly Trp Glu Pro Ala
            100                 105                 110
Val Glu Arg Asp Thr Asn Val Asp Glu Pro Val Glu Trp Glu Thr Pro
        115                 120                 125
Asp Leu Ser Gln Ala Glu Ile Glu Gln Lys Ile Lys Glu Tyr Asn Ala
    130                 135                 140
Gln Ile Asn Ser Asn Leu Phe Met Ser Leu Asn Lys Asp Gly Ser Tyr
145                 150                 155                 160
Thr Gly Phe Ile Lys Val Gln Leu Lys Leu Val Arg Pro Val Ser Val
                165                 170                 175
Pro Ser Ser Lys Lys Pro Pro Ser Leu Gln Asp Ala Arg Arg Gly Pro
            180                 185                 190
Gly Arg Gly Thr Ser Val Arg Arg Thr Ser Phe Tyr Leu Pro Lys
        195                 200                 205
Asp Ala Val Lys His Leu His Val Leu Ser Arg Thr Arg Ala Arg Glu
    210                 215                 220
Val Ile Glu Ala Leu Leu Arg Lys Phe Leu Val Asp Asp Pro Arg
225                 230                 235                 240
Lys Phe Ala Leu Phe Glu Arg Ala Glu Arg His Gly Gln Val Tyr Leu
                245                 250                 255
Arg Lys Leu Leu Asp Asp Glu Gln Pro Leu Arg Leu Arg Leu Leu Ala
            260                 265                 270
Gly Pro Ser Asp Lys Ala Leu Ser Phe Val Leu Lys Glu Asn Asp Ser
        275                 280                 285
Gly Glu Val Asn Trp Asp Ala Phe Ser Met Pro Glu Leu His Asn Phe
    290                 295                 300
Leu Arg Ile Leu Gln Arg Glu Glu Glu His Leu Arg Gln Ile Leu
305                 310                 315                 320
Gln Lys Tyr Ser Tyr Cys Arg Gln Lys Ile Gln Glu Ala Leu His Ala
                325                 330                 335
Cys Pro Leu Gly
            340

<210> SEQ ID NO 5
<211> LENGTH: 207
<212> TYPE: PRT
<213> ORGANISM: Homo sapiens

<400> SEQUENCE: 5

Met Asp Lys Asp Cys Glu Met Lys Arg Thr Thr Leu Asp Ser Pro Leu
1               5                   10                  15
Gly Lys Leu Glu Leu Ser Gly Cys Glu Gln Gly Leu His Glu Ile Lys
            20                  25                  30
Leu Leu Gly Lys Gly Thr Ser Ala Ala Asp Ala Val Glu Val Pro Ala
        35                  40                  45
Pro Ala Ala Val Leu Gly Gly Pro Glu Pro Leu Met Gln Cys Thr Ala
    50                  55                  60
Trp Leu Asn Ala Tyr Phe His Gln Pro Glu Ala Ile Glu Glu Phe Pro
65                  70                  75                  80
```

```
Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
                100                 105                 110

Ser Tyr Gln Gln Leu Ala Ala Leu Ala Gly Asn Pro Lys Ala Ala Arg
                115                 120                 125

Ala Val Gly Gly Ala Met Arg Gly Asn Pro Val Pro Ile Leu Ile Pro
                130                 135                 140

Cys His Arg Val Val Cys Ser Ser Gly Ala Val Gly Asn Tyr Ser Gly
145                 150                 155                 160

Gly Leu Ala Val Lys Glu Trp Leu Leu Ala His Glu Gly His Arg Leu
                165                 170                 175

Gly Lys Pro Gly Leu Gly Gly Ser Ser Gly Leu Ala Gly Ala Trp Leu
                180                 185                 190

Lys Gly Ala Gly Ala Thr Ser Gly Ser Pro Pro Ala Gly Arg Asn
                195                 200                 205

<210> SEQ ID NO 6
<211> LENGTH: 1430
<212> TYPE: PRT
<213> ORGANISM: Homo sapiens

<400> SEQUENCE: 6

Met Thr Val Phe Arg Gln Glu Asn Val Asp Asp Tyr Tyr Asp Thr Gly
1               5                   10                  15

Glu Glu Leu Gly Ser Gly Gln Phe Ala Val Val Lys Lys Cys Arg Glu
                20                  25                  30

Lys Ser Thr Gly Leu Gln Tyr Ala Ala Lys Phe Ile Lys Lys Arg Arg
                35                  40                  45

Thr Lys Ser Ser Arg Arg Gly Val Ser Arg Glu Asp Ile Glu Arg Glu
            50                  55                  60

Val Ser Ile Leu Lys Glu Ile Gln His Pro Asn Val Ile Thr Leu His
65              70                  75                  80

Glu Val Tyr Glu Asn Lys Thr Asp Val Ile Leu Ile Leu Glu Leu Val
                85                  90                  95

Ala Gly Gly Glu Leu Phe Asp Phe Leu Ala Glu Lys Glu Ser Leu Thr
                100                 105                 110

Glu Glu Glu Ala Thr Glu Phe Leu Lys Gln Ile Leu Asn Gly Val Tyr
                115                 120                 125

Tyr Leu His Ser Leu Gln Ile Ala His Phe Asp Leu Lys Pro Glu Asn
                130                 135                 140

Ile Met Leu Leu Asp Arg Asn Val Pro Lys Pro Arg Ile Lys Ile Ile
145                 150                 155                 160

Asp Phe Gly Leu Ala His Lys Ile Asp Phe Gly Asn Glu Phe Lys Asn
                165                 170                 175

Ile Phe Gly Thr Pro Glu Phe Val Ala Pro Glu Ile Val Asn Tyr Glu
                180                 185                 190

Pro Leu Gly Leu Glu Ala Asp Met Trp Ser Ile Gly Val Ile Thr Tyr
                195                 200                 205

Ile Leu Leu Ser Gly Ala Ser Pro Phe Leu Gly Asp Thr Lys Gln Glu
                210                 215                 220

Thr Leu Ala Asn Val Ser Ala Val Asn Tyr Glu Phe Glu Asp Glu Tyr
225                 230                 235                 240

Phe Ser Asn Thr Ser Ala Leu Ala Lys Asp Phe Ile Arg Arg Leu Leu
```

```
                    245                 250                 255
Val Lys Asp Pro Lys Arg Met Thr Ile Gln Asp Ser Leu Gln His
                260                 265                 270

Pro Trp Ile Lys Pro Lys Asp Thr Gln Gln Ala Leu Ser Arg Lys Ala
            275                 280                 285

Ser Ala Val Asn Met Glu Lys Phe Lys Phe Ala Ala Arg Lys Lys
            290                 295                 300

Trp Lys Gln Ser Val Arg Leu Ile Ser Leu Cys Gln Arg Leu Ser Arg
305                 310                 315                 320

Ser Phe Leu Ser Arg Ser Asn Met Ser Val Ala Arg Ser Asp Thr
                325                 330                 335

Leu Asp Glu Glu Asp Ser Phe Val Met Lys Ala Ile His Ala Ile
                340                 345                 350

Asn Asp Asp Asn Val Pro Gly Leu Gln His Leu Leu Gly Ser Leu Ser
                355                 360                 365

Asn Tyr Asp Val Asn Gln Pro Asn Lys His Gly Thr Pro Leu Leu
            370                 375                 380

Ile Ala Ala Gly Cys Gly Asn Ile Gln Ile Leu Gln Leu Leu Ile Lys
385                 390                 395                 400

Arg Gly Ser Arg Ile Asp Val Gln Asp Lys Gly Gly Ser Asn Ala Val
                405                 410                 415

Tyr Trp Ala Ala Arg His Gly His Val Asp Thr Leu Lys Phe Leu Ser
                420                 425                 430

Glu Asn Lys Cys Pro Leu Asp Val Lys Asp Lys Ser Gly Glu Met Ala
                435                 440                 445

Leu His Val Ala Ala Arg Tyr Gly His Ala Asp Val Ala Gln Leu Leu
            450                 455                 460

Cys Ser Phe Gly Ser Asn Pro Asn Ile Gln Asp Lys Glu Glu Thr
465                 470                 475                 480

Pro Leu His Cys Ala Ala Trp His Gly Tyr Tyr Ser Val Ala Lys Ala
                485                 490                 495

Leu Cys Glu Ala Gly Cys Asn Val Asn Ile Lys Asn Arg Glu Gly Glu
            500                 505                 510

Thr Pro Leu Leu Thr Ala Ser Ala Arg Gly Tyr His Asp Ile Val Glu
            515                 520                 525

Cys Leu Ala Glu His Gly Ala Asp Leu Asn Ala Cys Asp Lys Asp Gly
            530                 535                 540

His Ile Ala Leu His Leu Ala Val Arg Arg Cys Gln Met Glu Val Ile
545                 550                 555                 560

Lys Thr Leu Leu Ser Gln Gly Cys Phe Val Asp Tyr Gln Asp Arg His
                565                 570                 575

Gly Asn Thr Pro Leu His Val Ala Cys Lys Asp Gly Asn Met Pro Ile
            580                 585                 590

Val Val Ala Leu Cys Glu Ala Asn Cys Asn Leu Asp Ile Ser Asn Lys
            595                 600                 605

Tyr Gly Arg Thr Pro Leu His Leu Ala Ala Asn Asn Gly Ile Leu Asp
            610                 615                 620

Val Val Arg Tyr Leu Cys Leu Met Gly Ala Ser Val Glu Ala Leu Thr
625                 630                 635                 640

Thr Asp Gly Lys Thr Ala Glu Asp Leu Ala Arg Ser Glu Gln His Glu
                645                 650                 655

His Val Ala Gly Leu Leu Ala Arg Leu Arg Lys Asp Thr His Arg Gly
            660                 665                 670
```

-continued

```
Leu Phe Ile Gln Gln Leu Arg Pro Thr Gln Asn Leu Gln Pro Arg Ile
        675                 680                 685

Lys Leu Lys Leu Phe Gly His Ser Gly Ser Gly Lys Thr Thr Leu Val
    690                 695                 700

Glu Ser Leu Lys Cys Gly Leu Leu Arg Ser Phe Phe Arg Arg Arg Arg
705                 710                 715                 720

Pro Arg Leu Ser Ser Thr Asn Ser Ser Arg Phe Pro Pro Ser Pro Leu
                725                 730                 735

Ala Ser Lys Pro Thr Val Ser Val Ser Ile Asn Asn Leu Tyr Pro Gly
            740                 745                 750

Cys Glu Asn Val Ser Val Arg Ser Arg Ser Met Met Phe Glu Pro Gly
        755                 760                 765

Leu Thr Lys Gly Met Leu Glu Val Phe Val Ala Pro Thr His His Pro
    770                 775                 780

His Cys Ser Ala Asp Asp Gln Ser Thr Lys Ala Ile Asp Ile Gln Asn
785                 790                 795                 800

Ala Tyr Leu Asn Gly Val Gly Asp Phe Ser Val Trp Glu Phe Ser Gly
                805                 810                 815

Asn Pro Val Tyr Phe Cys Cys Tyr Asp Tyr Phe Ala Ala Asn Asp Pro
            820                 825                 830

Thr Ser Ile His Val Val Phe Ser Leu Glu Glu Pro Tyr Glu Ile
        835                 840                 845

Gln Leu Asn Gln Val Ile Phe Trp Leu Ser Phe Leu Lys Ser Leu Val
    850                 855                 860

Pro Val Glu Glu Pro Ile Ala Phe Gly Gly Lys Leu Lys Asn Pro Leu
865                 870                 875                 880

Gln Val Val Leu Val Ala Thr His Ala Asp Ile Met Asn Val Pro Arg
                885                 890                 895

Pro Ala Gly Gly Glu Phe Gly Tyr Asp Lys Asp Thr Ser Leu Leu Lys
            900                 905                 910

Glu Ile Arg Asn Arg Phe Gly Asn Asp Leu His Ile Ser Asn Lys Leu
        915                 920                 925

Phe Val Leu Asp Ala Gly Ala Ser Gly Ser Lys Asp Met Lys Val Leu
    930                 935                 940

Arg Asn His Leu Gln Glu Ile Arg Ser Gln Ile Val Ser Val Cys Pro
945                 950                 955                 960

Pro Met Thr His Leu Cys Glu Lys Ile Ile Ser Thr Leu Pro Ser Trp
                965                 970                 975

Arg Lys Leu Asn Gly Pro Asn Gln Leu Met Ser Leu Gln Gln Phe Val
            980                 985                 990

Tyr Asp Val Gln Asp Gln Leu Asn Pro Leu Ala Ser Glu Glu Asp Leu
        995                 1000                1005

Arg Arg Ile Ala Gln Gln Leu His Ser Thr Gly Glu Ile Asn Ile
    1010                1015                1020

Met Gln Ser Glu Thr Val Gln Asp Val Leu Leu Leu Asp Pro Arg
    1025                1030                1035

Trp Leu Cys Thr Asn Val Leu Gly Lys Leu Leu Ser Val Glu Thr
    1040                1045                1050

Pro Arg Ala Leu His His Tyr Arg Gly Arg Tyr Thr Val Glu Asp
    1055                1060                1065

Ile Gln Arg Leu Val Pro Asp Ser Asp Val Glu Glu Leu Leu Gln
    1070                1075                1080
```

```
Ile Leu Asp Ala Met Asp Ile Cys Ala Arg Asp Leu Ser Ser Gly
1085                1090                1095

Thr Met Val Asp Val Pro Ala Leu Ile Lys Thr Asp Asn Leu His
1100                1105                1110

Arg Ser Trp Ala Asp Glu Glu Asp Glu Val Met Val Tyr Gly Gly
1115                1120                1125

Val Arg Ile Val Pro Val Glu His Leu Thr Pro Phe Pro Cys Gly
1130                1135                1140

Ile Phe His Lys Val Gln Val Asn Leu Cys Arg Trp Ile His Gln
1145                1150                1155

Gln Ser Thr Glu Gly Asp Ala Asp Ile Arg Leu Trp Val Asn Gly
1160                1165                1170

Cys Lys Leu Ala Asn Arg Gly Ala Glu Leu Leu Val Leu Leu Val
1175                1180                1185

Asn His Gly Gln Gly Ile Glu Val Gln Val Arg Gly Leu Glu Thr
1190                1195                1200

Glu Lys Ile Lys Cys Cys Leu Leu Leu Asp Ser Val Cys Ser Thr
1205                1210                1215

Ile Glu Asn Val Met Ala Thr Thr Leu Pro Gly Leu Leu Thr Val
1220                1225                1230

Lys His Tyr Leu Ser Pro Gln Gln Leu Arg Glu His His Glu Pro
1235                1240                1245

Val Met Ile Tyr Gln Pro Arg Asp Phe Phe Arg Ala Gln Thr Leu
1250                1255                1260

Lys Glu Thr Ser Leu Thr Asn Thr Met Gly Gly Tyr Lys Glu Ser
1265                1270                1275

Phe Ser Ser Ile Met Cys Phe Gly Cys His Asp Val Tyr Ser Gln
1280                1285                1290

Ala Ser Leu Gly Met Asp Ile His Ala Ser Asp Leu Asn Leu Leu
1295                1300                1305

Thr Arg Arg Lys Leu Ser Arg Leu Leu Asp Pro Pro Asp Pro Leu
1310                1315                1320

Gly Lys Asp Trp Cys Leu Leu Ala Met Asn Leu Gly Leu Pro Asp
1325                1330                1335

Leu Val Ala Lys Tyr Asn Thr Ser Asn Gly Ala Pro Lys Asp Phe
1340                1345                1350

Leu Pro Ser Pro Leu His Ala Leu Leu Arg Glu Trp Thr Thr Tyr
1355                1360                1365

Pro Glu Ser Thr Val Gly Thr Leu Met Ser Lys Leu Arg Glu Leu
1370                1375                1380

Gly Arg Arg Asp Ala Ala Asp Phe Leu Leu Lys Ala Ser Ser Val
1385                1390                1395

Phe Lys Ile Asn Leu Asp Gly Asn Gly Gln Glu Ala Tyr Ala Ser
1400                1405                1410

Ser Cys Asn Ser Gly Thr Ser Tyr Asn Ser Ile Ser Ser Val Val
1415                1420                1425

Ser Arg
1430

<210> SEQ ID NO 7
<211> LENGTH: 195
<212> TYPE: PRT
<213> ORGANISM: Homo sapiens

<400> SEQUENCE: 7
```

```
Met Gly Arg Ala Arg Asp Ala Ile Leu Asp Ala Leu Glu Asn Leu Thr
1               5                   10                  15

Ala Glu Glu Leu Lys Lys Phe Lys Leu Lys Leu Leu Ser Val Pro Leu
            20                  25                  30

Arg Glu Gly Tyr Gly Arg Ile Pro Arg Gly Ala Leu Leu Ser Met Asp
            35                  40                  45

Ala Leu Asp Leu Thr Asp Lys Leu Val Ser Phe Tyr Leu Glu Thr Tyr
            50                  55                  60

Gly Ala Glu Leu Thr Ala Asn Val Leu Arg Asp Met Gly Leu Gln Glu
65                  70                  75                  80

Met Ala Gly Gln Leu Gln Ala Ala Thr His Gln Gly Ser Gly Ala Ala
                85                  90                  95

Pro Ala Gly Ile Gln Ala Pro Pro Gln Ser Ala Ala Lys Pro Gly Leu
            100                 105                 110

His Phe Ile Asp Gln His Arg Ala Ala Leu Ile Ala Arg Val Thr Asn
            115                 120                 125

Val Glu Trp Leu Leu Asp Ala Leu Tyr Gly Lys Val Leu Thr Asp Glu
            130                 135                 140

Gln Tyr Gln Ala Val Arg Ala Glu Pro Thr Asn Pro Ser Lys Met Arg
145                 150                 155                 160

Lys Leu Phe Ser Phe Thr Pro Ala Trp Asn Trp Thr Cys Lys Asp Leu
            165                 170                 175

Leu Leu Gln Ala Leu Arg Glu Ser Gln Ser Tyr Leu Val Glu Asp Leu
            180                 185                 190

Glu Arg Ser
        195
```

DNA METHYLATION MARKERS AND METHODS OF USE

RELATED APPLICATIONS

This application is a continuation of U.S. application Ser. No. 12/515,735, filed Jun. 30, 2010, which is the U.S. national phase, pursuant to 35 U.S.C. § 371, of PCT international application Ser. No. PCT/US2007/024308, filed Nov. 20, 2007, designating the United States and published in English on May 29, 2008 as publication WO 2008/063655 A2, which claims priority to U.S. provisional application Ser. No. 60/860,196, filed Nov. 20, 2006. The entire contents of the aforementioned patent applications are incorporated herein by this reference.

FIELD OF THE INVENTION

The present invention relates to the use of nucleic acid methylation and methylation profiles to detect metastatic disease. In particular, the invention relates to methods for identifying metastases by detecting nucleic acid hypermethylation of one or more genes in one or more samples and, in particular, in tumor tissue and lymph nodes. The invention further relates to DNA hypermethylation as a predictor of disease recurrence and patient prognosis, specifically in patients suffering from cancer.

BACKGROUND OF THE INVENTION

Cancer remains one of the leading causes of death in the United States. Clinically, a broad variety of medical approaches, including surgery, radiation therapy and chemotherapeutic drug therapy are currently being used in the treatment of human cancer (see the textbook CANCER: Principles & Practice of Oncology, 2d Edition, De Vita et al., eds., J. B. Lippincott Company, Philadelphia, Pa., 1985). However, it is recognized that such approaches continue to be limited by an inability to predict the likelihood of metastasis and tumor recurrence or the most efficacious treatment regime for minimizing the occurrence of these negative outcomes.

Human cancer cells typically contain somatically altered nucleic acids, characterized by mutation, amplification, or deletion of critical genes. In addition, the nucleic acids from human cancer cells often display somatic changes in DNA methylation (36, 37, 38). However, a precise role for, and the significance of, abnormal DNA methylation in human tumorigenesis has not been well established.

Loss of gene function is cancer can occur by both genetic and epigenetic mechanisms. The best-defined epigenetic alteration of cancer genes involves DNA methylation of clustered CpG dinucleotides, or CpG islands, in promoter regions associated with the transcriptional inactivation of the affected genes. CpG islands are short sequences rich in the CpG dinucleotide, and can be found in the 5' region of about half of all human genes. Methylation of cytosine within 5' CGIs is associated with loss of gene expression and has been seen in a number of physiological conditions, including X chromosome inactivation and genomic imprinting. Aberrant methylation of CpG islands has been detected in genetic diseases such as the fragile-X syndrome, in aging cells and in neoplasia. About half of the tumor suppressor genes which have been shown to be mutated in the germline of patients with familial cancer syndromes have also been shown to be aberrantly methylated in some proportion of sporadic cancers, including Rb, VHL, p16, hMLH1, and BRCA1 (reviewed in Baylin, et al, Adv. Cancer Res. 72:141-196 1998). Methylation of tumor suppressor genes in cancer is usually associated with (1) lack of gene transcription and (2) absence of coding region mutation. Thus CpG island methylation can serve as an alternative mechanism of gene inactivation in cancer.

Cancer treatments, in general, have a higher rate of success if the cancer is diagnosed early, and treatment is started earlier in the disease process. A relationship between improved prognosis and stage of disease at diagnosis can be seen across a majority of cancers. Identification of the earliest changes in cells associated with cancer is thus a major focus in molecular cancer research. Diagnostic approaches based on identification of these changes in specific genes may allow implementation of early detection strategies and novel therapeutic approaches. Targeting these early changes will lead to more effective cancer treatment.

Despite advances in targeted therapy, surgery with curative intent remains the best therapeutic option for lung cancer patients with the earliest stages of disease. Ensuring in these patients that no occult metastatic cells have disseminated outside the area of curative resection is critical, because early spread of tumor cells is a leading cause of relapse (1-3). Despite the curative aim of early surgery, approximately 30%-40% of lung cancer patients with discrete lesions and histologically proven cancer negative lymph nodes (stage 1:T1-2N0) still die of recurrent disease (4-6). Further, many of these recurrences are systemic, underscoring the probability that these patients had metastatic disease that was undetectable, and beyond the margins of surgical resection.

Accordingly, there is a need in the art for improved methods of detection of proliferative disease, and in particular, for improved methods of detection of metastatic cancer that is undetectable by current methodologies.

SUMMARY

The invention features methods for identifying metastases by detecting nucleic acid hypermethylation of one or more genes in one or more samples, and in particular in tumor tissue and lymph nodes.

In one aspect, the invention features methods for identifying metastases in a subject comprising detecting nucleic acid hypermethylation of one or more genes in one or more samples, wherein detecting nucleic acid hypermethylation identifies metastases.

In one embodiment, the sample comprises cells or tissues selected from the group consisting of tumor, lymph nodes, bone marrow and blood. In a particular embodiment, the sample is from a tumor. In another particular embodiment, the sample is from a lymph node. In a more particular embodiment, the lymph node is a N1 lymph node or a mediastinal lymph node.

In another aspect the invention features methods for identifying metastases in a subject comprising detecting nucleic acid hypermethylation of one or more genes in tumor tissue or lymph node, wherein the genes are selected from the group consisting of genes involved in tumor suppression, DNA repair, apoptosis, anti-proliferation, ras signaling, adhesion, differentiation, development, and cell cycle regulation, wherein detecting nucleic acid hypermethylation identifies metastases.

In certain preferred embodiments of the above aspects, the metastases are micrometastases. In other preferred embodiments of the above aspects, the one or more genes comprise one or more CpG islands. In a further embodiment, the one or more genes is selected from the group consisting of H-cadherin, p16, APC, RASSF1A, MGMT, DAPK, and ASC.

H-cadherin, in certain exemplary embodiments is encoded by NCBI accession No. AAB18912 and is shown in (SEQ ID NO:1) below:

```
  1 mqprtplvlc vllsqvlllt saedldctpg fqqkvfhinq
    paefiedqsi lnltfsdckg 61 ndklryevss pyfkvnsdgg lvalrnitav gktlfvhart
    phaedmaelv ivggkdiqgs 121 lqdifkfart spvprqkrsi vvspilipen qrqpfprdvg
    kvvdsdrper skfrltgkgv 181 dqepkgifri nentgsvsvt rtldreviav yqlfvettdv
    ngktlegpvp levividqnd 241 nrpifregpy ighvmegspt gttvmrmtaf daddpatdna
    llrynirqqt pdkpspnmfy 301 idpekgdivt vvspalldre tlenpkyeli ieaqdmagld
    vgltgtatat imiddkndhs 361 pkftkkefqa tveegavgvi vnltvedkdd pttgawraay
    tiingnpgqs feihtnpqtn 421 egmlsvvkpl dyeisafhtl likvenedpl vpdvsygpss
    tatvhitvld vnegpvfypd 481 pmmvtrqedl svgsvlltvn atdpdslqhq tirysvykdp
    agwlninpin gtvdttavld 541 respfvdnsv ytalflaids gnppatgtgt llitledvnd
    napfiyptva evcddaknls 601 vvilgasdkd lhpntdpfkf eihkqavpdk vwkiskinnt
    halvsllqnl nkanynlpim 661 vtdsgkppmt nitdlrvqvc scrnskvdcn aagalrfslp
    svlllslfsl acl
``` p-16, in certain exemplary embodiments is encoded by NCBI accession No. CAB58124 and is shown in (SEQ ID NO:2) below:

```
  1 gshsmryfft svsrpgrgep rfiavgyvdd tqfvrfdsda
    asqrmeprap wieqegpeyw 61 dgetrkvkah sqtdrvdlgt lrgyynqsea gshtiqmmyg
    cdvgpdgrll rgyqqdaydg 121 kdyialnedl rswtaadmaa qitqrkweaa rvaeqlrayl
    egtcvewlrr ylengketlq 181 rt
```

APC, in certain exemplary embodiments is encoded by NCBI accession No. NP_000029 and is shown in (SEQ ID NO:3) below:

```
  1 maaasydqll kqvealkmen snlrqeledn snhltklete
    asnmkevlkq lqgsiedeam 61 assgqidlle rlkelnldss nfpgvklrsk mslrsygsre
    gsvssrsgec spvpmgsfpr 121 rgfvngsres tgyleeleke rsllladldk eekekdwyya
    qlqnltkrid slpltenfsl 181 qtdmtrrqle yearqirvam eeqlgtcqdm ekraqrriar
    iqqiekdilr irqllqsqat 241 eaerssqnkh etgshdaerq negqgvgein matsgngqgs
    ttrmdhetas vlsssssthsa 301 prrltshlgt kvemvyslls mlgthdkddm srtllamsss
    qdscismrqs gclplliqll 361 hgndkdsvll gnsrgskear arasaalhni ihsqpddkrg
    rreirvlhll eqiraycetc 421 wewqeahepg mdqdknpmpa pvehqicpav cvlmklsfde
    ehrhamnelg glqaiaellq 481 vdcemygltn dhysitlrry agmaltnltf gdvankatlc
    smkgcmralv aqlksesedl 541 qqviasvlrn lswradvnsk ktlrevgsvk almecalevk
    kestlksvls alwnlsahct 601 enkadicavd galaflvgtl tyrsqtntla iiesgggilr
    nvssliatne dhrqilrenn 661 clqtlllqhlk shsltivsna cgtlwnlsar npkdqealwd
    mgavsmlknl ihskhkmiam 721 gsaaalrnlm anrpakykda nimspgsslp slhvrkqkal
    eaeldaqhls etfdnidnls 781 pkashrskqr hkqslygdyv fdtnrhddnr sdnfntgnmt
    vlspylnttv lpssssssrgs 841 ldssrsekdr slerergigl gnyhpatenp gtsskrglqi
    sttaaqiakv meevsaihts 901 qedrssgstt elhcvtdern alrrssaaht hsntynftks
    ensnrtcsmp yakleykrss 961 ndslnsvsss dgygkrgqmk psiesysedd eskfcsygqy
    padlahkihs anhmddndge 1021 ldtpinyslk ysdeqlnsgr qspsqnerwa rpkhiiedei
     kqseqrqsrn qsttypvyte 1081 stddkhlkfq phfgqqecvs pyrsrgangs etnrvgsnhg
     inqnvsqslc qeddyeddkp 1141 tnyserysee eqheeeerpt nysikyneek rhvdqpidys
     lkyatdipss qkqsfsfsks 1201 ssgqsskteh mssssentst pssnakrqnq lhpssaqsrs
     gqpqkaatck vssinqetiq 1261 tycvedtpic fsrcsslssl ssaedeigcn qttqeadsan
     tlqiaeikek igtrsaedpv 1321 sevpavsqhp rtkssrlqgs slssesarhk avefssgaks
     psksgaqtpk sppehyvqet 1381 plmfsrctsv ssldsfesrs iassvqsepc sgmvsgiisp
     sdlpdspgqt mppsrsktpp 1441 pppqtaqtkr evpknkapta ekresgpkqa avnaavqrvq
     vlpdadtllh fatestpdgf 1501 scssslsals ldepfiqkdv elrimppvqe ndngnetese
     qpkesnenqe keaektidse 1561 kdllddsddd dieileeecii samptkssrk akkpaqtask
     lpppvarkps qlpvykllps 1621 qnrlqpqkhv sftpgddmpr vycvegtpin fstatslsdl
     tiesppnela agegvrggaq 1681 sgefekrdti ptegrstdea qggktssvti pelddnkaee
     gdilaecins ampkgkshkp 1741 frvkkimdqv qqasasssap nknqldgkkk kptspvkpip
     qnteyrtrvr knadsknnln 1801 aervfsdnkd skkqnlknns kvfndklpnn edrvrgsfaf
     dsphhytpie gtpycfsrnd
```

```
1861  slssldfddd dvdlsrekae lrkakenkes eakvtshtel
      tsnqqsankt qaiakqpinr 1921  gqpkpilqkq stfpqsskdi pdrgaatdek lqnfaientp
      vcfshnssls slsdidqenn 1981  nkenepiket eppdsqgeps kpqasgyapk sfhvedtpvc
      fsrnsslssl sidseddllq 2041  ecissampkk kkpsrlkgdn ekhsprnmgg ilgedltldl
      kdiqrpdseh glspdsenfd 2101  wkaiqegans ivsslhqaaa aaclsrqass dsdsilslks
      gislgspfhl tpdqeekpft 2161  snkgprilkp gekstletkk ieseskgikg gkkvykslit
      gkvrsnseis gqmkqplqan 2221  mpsisrgrtm ihipgvrnss sstspvskkg pplktpasks
      psegqtatts prgakpsvks 2281  elspvarqts qiggsskaps rsgsrdstps rpaqqplsrp
      iqspgrnsis pgrngisppn 2341  klsqlprtss pstastkssg sgkmsytspg rqmsqqnltk
      qtglsknass iprsesaskg 2401  lnqmnngnga nkkvelsrms stkssgsesd rserpvlvrq
      stfikeapsp tlrrkleesa 2461  sfeslspssr pasptrsqaq tpvlspslpd mslsthssvq
      aggwrklppn lsptieyndg 2521  rpakrhdiar shsespsrlp inrsgtwkre hskhssslpr
      vstwrrtgss ssilsasses 2581  sekaksedek hvnsisgtkq skenqvsakg twrkikenef
      sptnstsqtv ssgatngaes 2641  ktliyqmapa vsktedvwvr iedcpinnpr sgrsptgntp
      pvidsvseka npnikdskdn 2701  qakqnvgngs vpmrtvglen rlnsfiqvda pdqkgteikp
      gqnnpvpvse tnessivert 2761  pfssssskh sspsgtvaar vtpfnynpsp rkssadstsa
      rpsqiptpvn nntkkrdskt 2821  dstessgtqs pkrhsgsylv tsv
```

RASSF1A, in certain exemplary embodiments is encoded by NCBI accession No. NP_009113 and is shown in (SEQ ID NO:4) below:

```
  1  msgepeliel relapagrag kgrtrleran alriargtac
     nptrqlvpgr ghrfqpagpa 61  thtwcdlcgd fiwgvvrkgl qcahckftch yrcralvcld
     ccgprdlgwe paverdtnvd 121  epvewetpdl sqaeieqkik eynaqinsnl fmslnkdgsy
     tgfikvqlkl vrpvsvpssk 181  kppslqdarr gpgrgtsvrr rtsfylpkda vkhlhvlsrt
     rarevieall rkflvvddpr 241  kfalferaer hgqvylrkll ddeqplrlrl lagpsdkals
     fvlkendsge vnwdafsmpe 301  lhnflrilqr eeeehlrqil qkysycrqki qealhacplg
```

MGMT, in certain exemplary embodiments is encoded by NCBI accession No. AAH00824 and is shown in (SEQ ID NO:5) below:

```
  1  mdkdcemkrt tldsplgkle lsgceqglhe ikllgkgtsa
     adavevpapa avlggpeplm 61  qctawlnayf hqpeaieefp vpalhhpvfq qesftrqvlw
     kllkvvkfge visyqqlaal 121  agnpkaarav ggamrgnpvp ilipchrvvc ssgavgnysg
     glavkewlla heghrlgkpg 181  lggssglaga wlkgagatsg sppagrn
```

DAPK, in certain exemplary embodiments is encoded by NCBI accession No. NP_004929 and is shown in (SEQ ID NO:6) below:

```
  1  mtvfrqenvd dyydtgeelg sgqfavvkkc rekstglqya
     akfikkrrtk ssrrgvsred 61  ierevsilke iqhpnvitlh evyenktdvi lilelvagge
     lfdflaekes lteeeatefl 121  kqilngvyyl hslqiahfdl kpenimlldr nvpkprikii
     dfglahkidf gnefknifgt 181  pefvapeivn yeplgleadm wsigvityil lsgaspflgd
     tkqetlanvs avnyefedey 241  fsntsalakd firrllvkdp kkrmtiqdsl qhpwikpkdt
     qqalsrkasa vnmekfkkfa 301  arkkwkqsvr lislcqrlsr sflsrsnmsv arsddtldee
     dsfvmkaiih ainddnvpgl 361  qhllgslsny dvnqpnkhgt pplliaagcg niqilqllik
     rgsridvqdk ggsnavywaa 421  rhghvdtlkf lsenkcpldv kdksgemalh vaaryghadv
     aqllcsfgsn pniqdkeeet 481  plhcaawhgy ysvakalcea gcnvniknre getplltasa
     rgyhdivecl aehgadlnac 541  dkdghialhl avrrcqmevi ktllsqgcfv dyqdrhgntp
     lhvackdgnm pivvalcean 601  cnldisnkyg rtplhlaann gildvvrylc lmgasvealt
     tdgktaedla rseqhehvag 661  llarlrkdth rglfiqqlrp tqnlqprikl klfghsgsgk
     ttlveslkcg llrsffrrrr 721  prlsstnssr fppsplaskp tvsvsinnly pgcenvsvrs
     rsmmfepglt kgmlevfvap 781  thhphcsadd qstkaidiqn aylngvgdfs vwefsgnpvy
     fccydyfaan dptsihvvvf 841  sleepyeiql nqvifwlsfl kslvpveepi afggklknpl
     qvvlvathad imnvprpagg 901  efgydkdtsl lkeirnrfgn dlhisnklfv ldagasgskd
     mkvlrnhlqe irsqivsvcp 961  pmthlcekii stlpswrkln gpnqlmslqq fvydvqdqln
     plaseedlrr iaqqlhstge 1021 inimqsetvq dvllldprwl ctnvlgklls vetpralhhy
     rgrytvediq rlvpdsdvee 1081 llqildamdi cardlssgtm vdvpaliktd nlhrswadee
     devmvyggvr ivpvehltpf 1141 pcgifhkvqv nlcrwihqqs tegdadirlw vngcklanrg
     aellvllvnh gqgievqvrg 1201 letekikccl lldsvcstie nvmattlpgl ltvkhylspq
     qlrehhepvm iyqprdffra
```

```
1261  qtlketsltn tmggykesfs simcfgchdv ysqaslgmdi
      hasdlnlltr rklsrlldpp 1321  dplgkdwcll amnlglpdlv akyntsngap kdflpsplha
      llrewttype stvgtlmskl 1381  relgrrdaad fllkassvfk inldgngqea yasscnsgts
      ynsissvvsr
```

ASC, in certain exemplary embodiments is encoded by NCBI accession No. NP_037390 and is shown in (SEQ ID NO:7) below:

```
  1  mgrardaild alenltaeel kkfklkllsv plregygrip
     rgallsmdal dltdklvsfy 61  letygaelta nvlrdmglqe magqlqaath qgsgaapagi
     qappqsaakp glhfidqhra 121  aliarvtnve wlldalygkv ltdeqyqavr aeptnpskmr
     klfsftpawn wtckdlllqa 181  lresqsylve dlers
```

In other embodiments of the above aspects, hypermethylation of at least one of the genes is detected. In still other embodiments of the above aspects, hypermethylation of at least two of the genes is detected.

In other aspects, the invention features methods for identifying micrometastases in a subject comprising detecting nucleic acid hypermethylation of at least one or more genes in a sample comprising tumor and lymph nodes, wherein the sample genes are selected from the group consisting of H-cadherin, p16, APC, RASSF1A, MGMT, DAPK, and ASC, and wherein detecting nucleic acid methylation identifies micrometastases.

In a preferred embodiment, hypermethylation of at least two of the genes is detected. In another embodiment, at least two of the genes are selected from p-16 and H-cadherin, H-cadherin and APC, APC and p16, or RASSf1A and p16.

In another further embodiment, the detection of metastases is used to detect or diagnose a proliferative disease.

In certain embodiments, the detection or diagnosis is performed after surgery or therapy to treat a proliferative disease. In other certain embodiments, the detection is used to predict the recurrence of a proliferative disease. In other certain embodiments, the detection is used to stage a proliferative disease. In still other certain embodiments, the detection is further used to determine a course of treatment for a subject.

In other aspects, the invention features a method for detecting or diagnosing a proliferative disease in a subject comprising detecting nucleic acid hypermethylation of one or more genes in one or more samples, wherein detecting nucleic acid hypermethylation is used to detect or diagnose a proliferative disease.

In still other aspects, the invention features a method for predicting the recurrence of a proliferative disease in a subject comprising detecting nucleic acid hypermethylation of one or more genes wherein detecting nucleic acid hypermethylation of one or more genes is a predictor of the recurrence of a proliferative disease.

In one embodiment, hypermethylation of one or more genes is detected in tumor or lymph nodes.

In a related embodiment, detection of hypermethylation of one or more genes in lymph nodes is predictive of aggressive disease recurrence.

In another aspect, the invention features a method for staging or re-staging a proliferative disease in a subject comprising detecting nucleic acid hypermethylation of one or more genes wherein detecting nucleic acid hypermethylation is used for staging or re-staging a proliferative disease.

In a related embodiment, the stage of proliferative disease is predictive of disease recurrence. In a further embodiment, the stage of proliferative disease determines course of treatment.

In another aspect, the invention features a method for determining the prognosis of a subject suffering from a proliferative disease comprising detecting nucleic acid hypermethylation of one or more genes wherein the detection of nucleic acid hypermethylation is used for determining the prognosis of a subject suffering from a proliferative disease.

In a related embodiment, the prognosis determines course of treatment.

In an embodiment of any of the above-mentioned aspects, the subject is a human.

In another embodiment of any of the above-mentioned aspects, the method is performed prior to therapeutic intervention for the disease.

In another embodiment of any of the above-mentioned aspects, the method is performed after therapeutic intervention for the disease. In a related embodiment, the therapeutic intervention is selected from treatment with an agent or surgery. In another related embodiment, hypermethylation is detected in CpG islands of the one or more genes. In a further related embodiment, hypermethylation is detected in CpG islands.

In another aspect, the invention features methods for detecting or diagnosing a proliferative disease in a subject comprising extracting nucleic acid from one or more cell or tissue samples, detecting nucleic acid hypermethylation of one or more genes in the sample; and identifying the nucleic acid hypermethylation state of one or more genes, wherein nucleic acid hypermethylation of genes indicates a proliferative disease.

In a further aspect, the invention features methods for predicting the recurrence of a proliferative disease in a subject comprising extracting nucleic acid from one or more cell or tissue samples, detecting nucleic acid hypermethylation of one or more genes in the sample; and identifying the nucleic acid hypermethylation state of one or more genes, wherein nucleic acid hypermethylation of genes is indicative of the recurrence of a proliferative disease.

In a further aspect, the invention features methods for staging or re-staging a proliferative disease in a subject comprising extracting nucleic acid from one or more cell or tissue samples, detecting nucleic acid hypermethylation of one or more genes in the sample; and identifying the nucleic acid hypermethylation state of one or more genes, wherein nucleic acid hypermethylation of genes is used for staging or re-staging of a proliferative disease.

In one embodiment of the above-mentioned aspects, the tissue samples are selected from tumor, lymph node, bone marrow or blood or a combination thereof.

In another embodiment of the above-mentioned aspects, the method determines the course of disease treatment.

In still another embodiment of the above-mentioned aspects, the method is performed prior to therapeutic intervention for the disease.

In still another embodiment of the above-mentioned aspects, the method is performed after therapeutic intervention for the disease.

In a further embodiment, the therapeutic intervention is selected from treatment with an agent or surgery.

In another aspect, the invention features methods of treating a subject having or at risk for having a proliferative disease comprising identifying nucleic acid hypermethylation of one or more genes, where nucleic acid hypermethylation indicates having or a risk for having a proliferative disease, and administering to the subject a therapeutically effective amount of a demethylating agent, thereby treating a subject having or at risk for having a proliferative disease.

In one particular embodiment, the method is used in combination with one or more chemotherapeutic agents.

In another particular embodiment of the above-mentioned aspects, the method further comprises comparing the nucleic acid hypermethylation of one or more genes in the sample with comparable samples obtained from a normal subject.

In a further embodiment of the above-mentioned aspects, detecting nucleic acid hypermethylation of one or more genes indicates the presence of metastases.

In a particular embodiment, the metastases are micrometastases.

In another particular embodiment of any one of the above-mentioned aspects, the proliferative disease is a neoplasia. In a preferred embodiment, the neoplasia is cancer. In another preferred embodiment, the cancer is a solid tumor. In a further embodiment, the cancer is selected from the group consisting of lung cancer, pancreatic cancer, esophageal cancer, head and neck cancer, stomach cancer, liver cancer, prostate cancer, gastrointestinal cancer, ovarian cancer, and uterine cancer.

In another particular embodiment of the above-mentioned aspects, the cells or tissues are selected from the group consisting of tumor, lymph nodes, bone marrow or blood. In a related embodiment, the cells or tissues are from a tumor or the lymph nodes. In a further embodiment, the lymph node is a N1 lymph node or a mediastinal lymph node.

In another aspect, the invention features a method of identifying an agent that de-methylates hypermethylated nucleic acid comprising identifying one or more cell or tissue samples with hypermethylated nucleic acid, extracting the hypermethylated nucleic acid, contacting the nucleic acid with one or more nucleic acid de-methylating candidate agents and a control agent, identifying the nucleic acid hypermethylation state, wherein nucleic acid de-methylation of genes in the sample by the candidate agent compared to the control indicates a demethylating agent, and thereby identifying an agent that de-methylates hypermethylated nucleic acid.

In one embodiment of any of the above-mentioned aspects, the one or more genes are selected from the group consisting of genes involved in tumor suppression, DNA repair, anti-proliferation, apotosis, ras signaling, adhesion, differentiation, development, and cell cycle regulation.

In another embodiment of any of the above-mentioned aspects, the one or more genes are selected from a panel consisting of (1) genes involved in tumor suppression and cell adhesion, (2) genes involved in cell cycle regulation and adhesion, (3) genes involved in tumor suppression and cell cycle regulation, and (4) genes involved in ras signaling and cell cycle control.

In still another embodiment of any of the above-mentioned aspects, the one or more genes comprise one or more CpG islands.

In a related embodiment, the genes are selected from the group consisting of p-16, H-cadherin, APC, RASSF1A, MGMT, DAPK, and ASC.

In another related embodiment, the hypermethylation of at least one of the genes is detected. In a further related embodiment, the hypermethylation of at least two of the genes is detected. In still another related embodiment, the two genes are selected from p-16 and H-cadherin, H-cadherin and APC, APC and p16, or RASSf1A and p16.

In another embodiment of any of the above-mentioned aspects, the detection of nucleic acid methylation is by a quantitative method.

In another embodiment of any of the above-mentioned aspects, the detection of nucleic acid methylation is carried out by polymerase chain reaction (PCR) analysis. In a related embodiment, the PCR is methylation specific PCR (MSP).

In a particular embodiment, the method of detecting nucleic acid methylation is performed as a high-throughput method.

In another particular embodiment, the method is used in combination with the detection of other epigenetic markers. In a particular related embodiment, the other epigenetic markers are plasma or tumor epigenetic markers.

In an embodiment of the above-described aspects, hypermethylation is detected in CpG islands of the one or more genes. In a further embodiment of the above-described aspects, hypermethylation is detected in CpG islands of the promoter region.

In other aspects, the invention features kits for identifying the nucleic acid hypermethylation state of one or more genes comprising gene specific primers for use in polymerase chain reaction (PCR), and instructions for use.

In still other aspects, the invention features kits for detecting metastases by detecting nucleic acid hypermethylation of one or more genes, the kit comprising gene specific primers for use in polymerase chain reaction (PCR), and instructions for use.

In one embodiment, the metastases are micrometastases.

In another embodiment, the PCR is methylation specific PCR (MSP).

In still another embodiment, the one or more genes are selected from the group consisting of genes involved in tumor suppression, DNA repair, anti-proliferation, apotosis, ras signaling, adhesion, differentiation, development, and cell cycle regulation.

In another embodiment, the one or more genes are selected from a panel consisting of (1) genes involved in tumor suppression and cell adhesion, (2) genes involved in cell cycle regulation and adhesion, (3) genes involved in tumor suppression and cell cycle regulation, and (4) genes involved in ras signaling and cell cycle control.

In a related embodiment, the one or more genes comprise one or more CpG islands. In a further related embodiment, the CpG islands are in the promoter region. In another related embodiment, the genes are selected from the group consisting of p-16, H-cadherin, APC, RASSF1A, MGMT, DAPK, and ASC In another embodiment, the hypermethylation of at least one of the genes is detected. In still another embodiment, the hypermethylation of at least two of the genes is detected. In still another further embodiment, the two genes are selected from p-16 and H-cadherin, H-cadherin and APC, APC and p16, or RASSf1A and p16.

Other aspects of the invention are described infra.

DEFINITIONS

Figure 1:
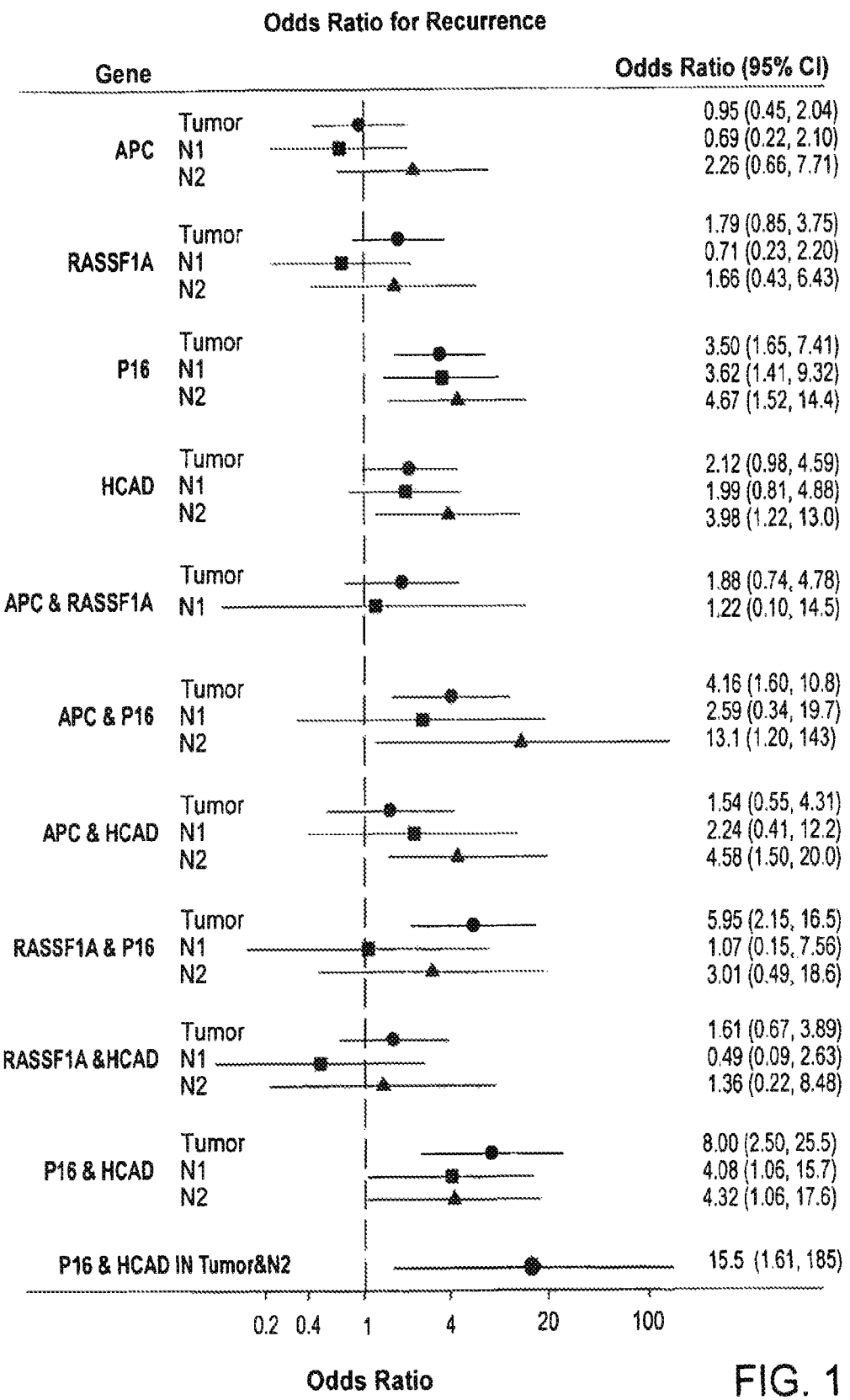
FIG. 1 shows the results of multivariate logistic regression analysis performed using the four genes that exhibited the largest univariate distribution differences in methylation: p16, H-cadherin, APC, and RASSF1A.
Figure 2A:
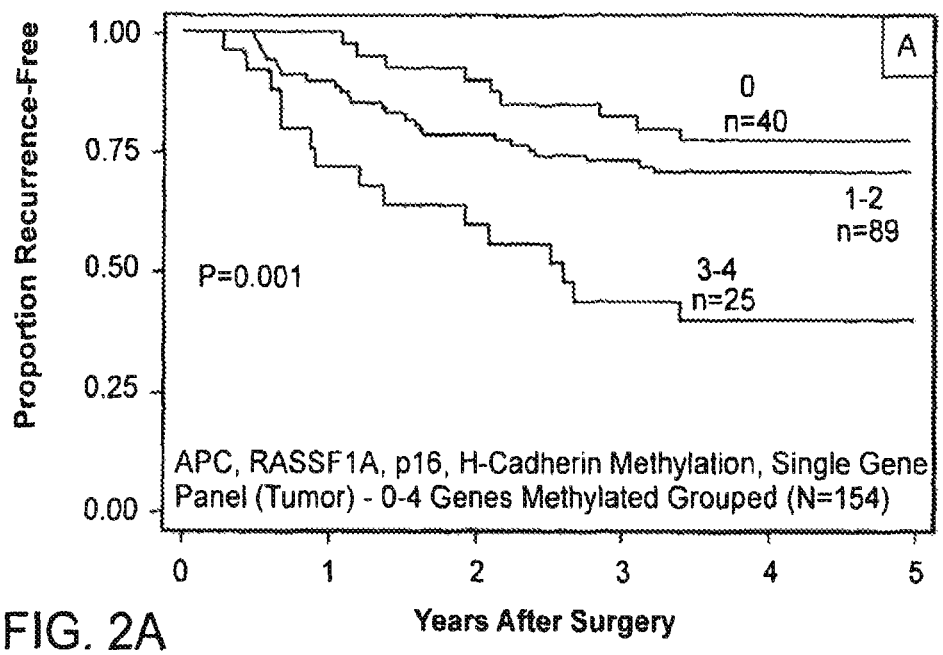
FIG. 2 (A-L) are graphs showing Kaplan-Meier estimates of recurrence-free survival of pathologic Stage 1 lung cancer patients at the Johns Hopkins Hospital, according to number of methylated genes in a 4-gene panel at time of surgical resection.
Figure 2B:
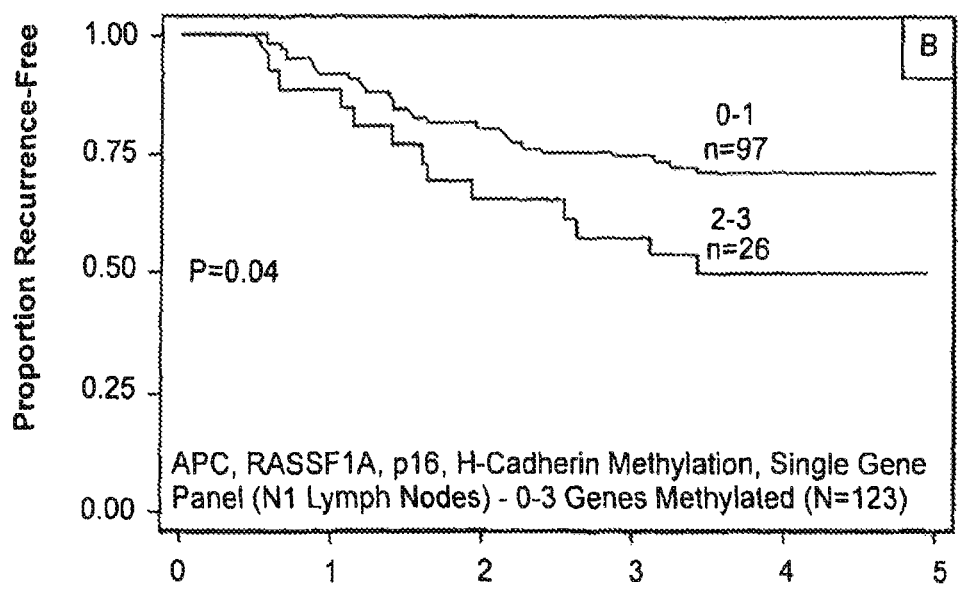
Figure 2C:
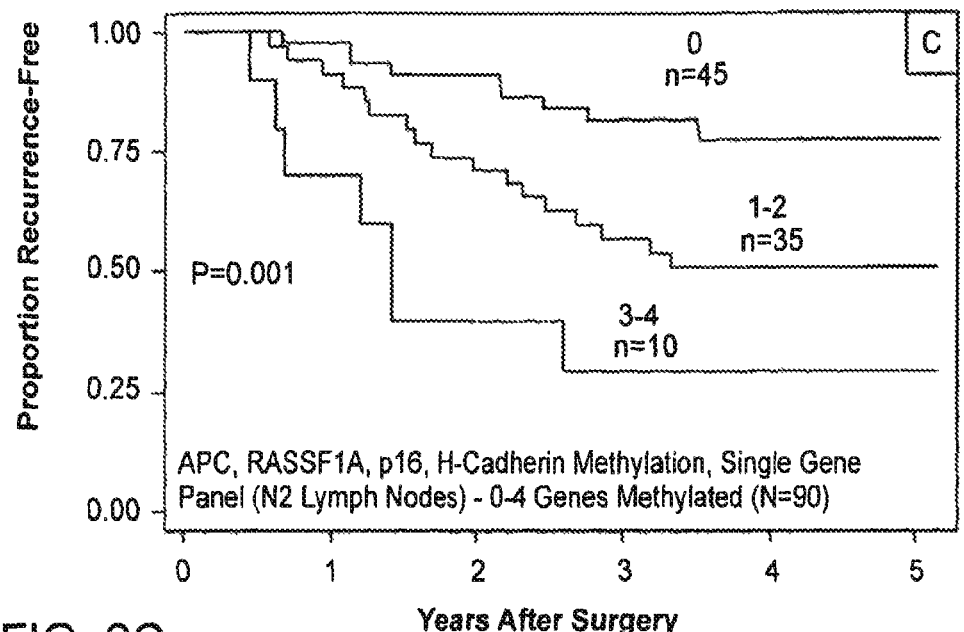
Figure 2D:
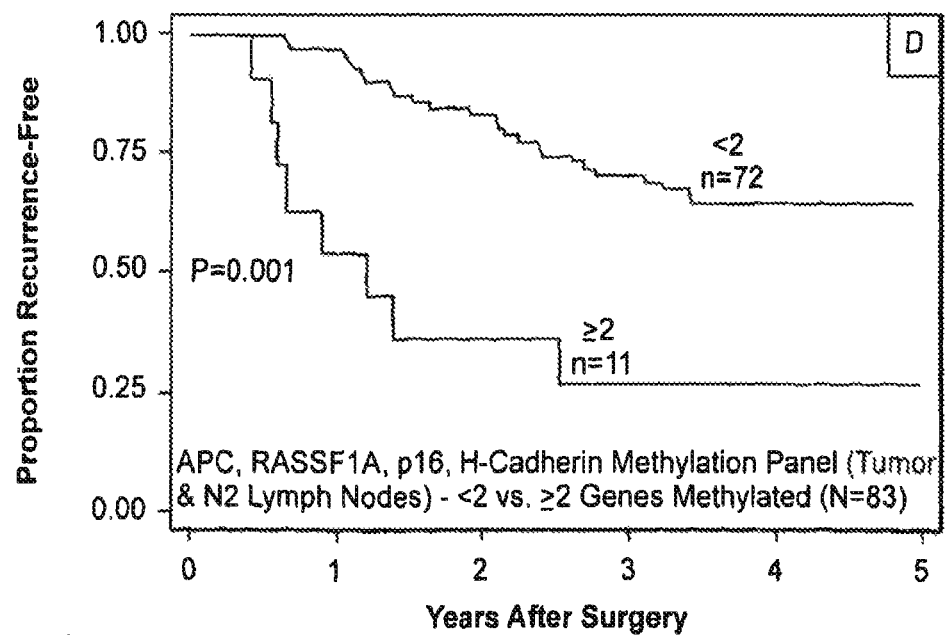
Figure 2E:
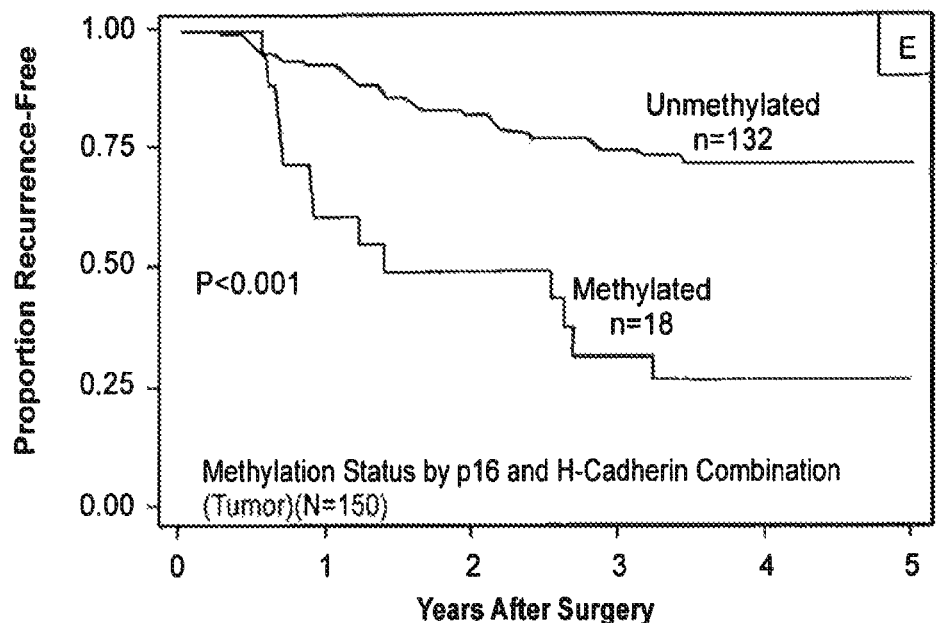
Figure 2F:
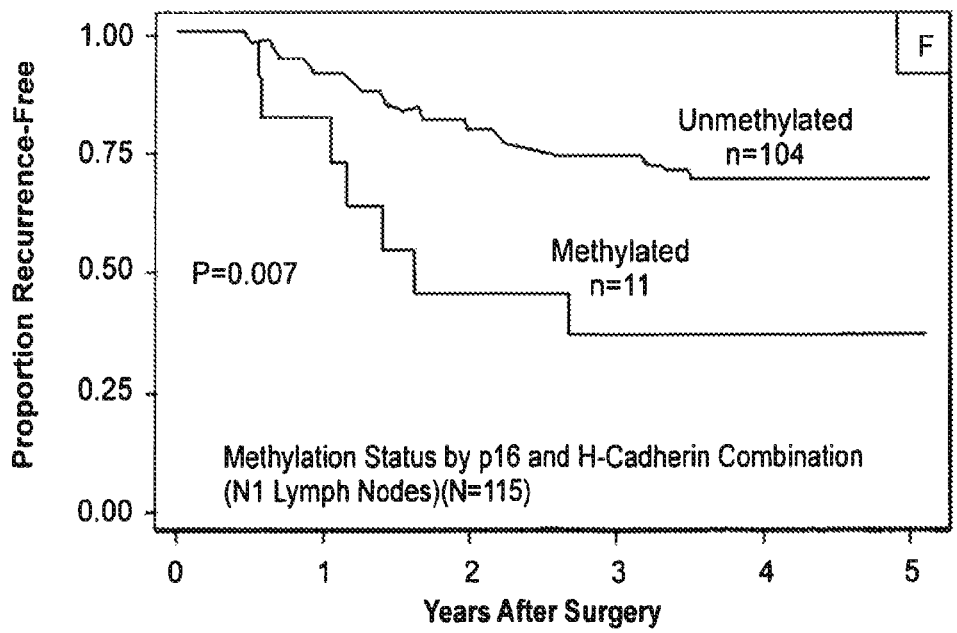
Figure 2G:
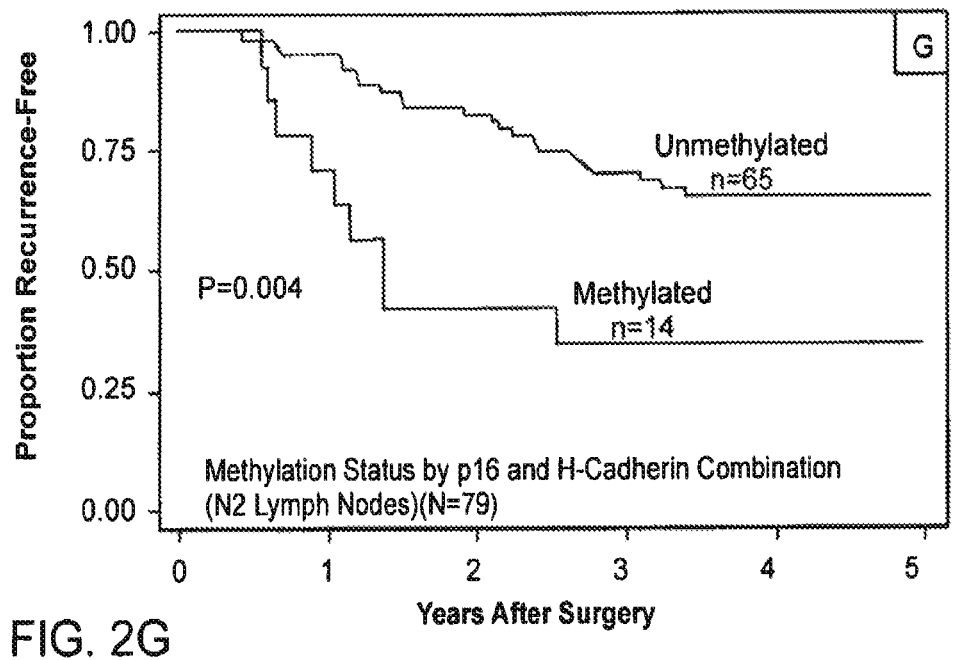
Figure 2H:
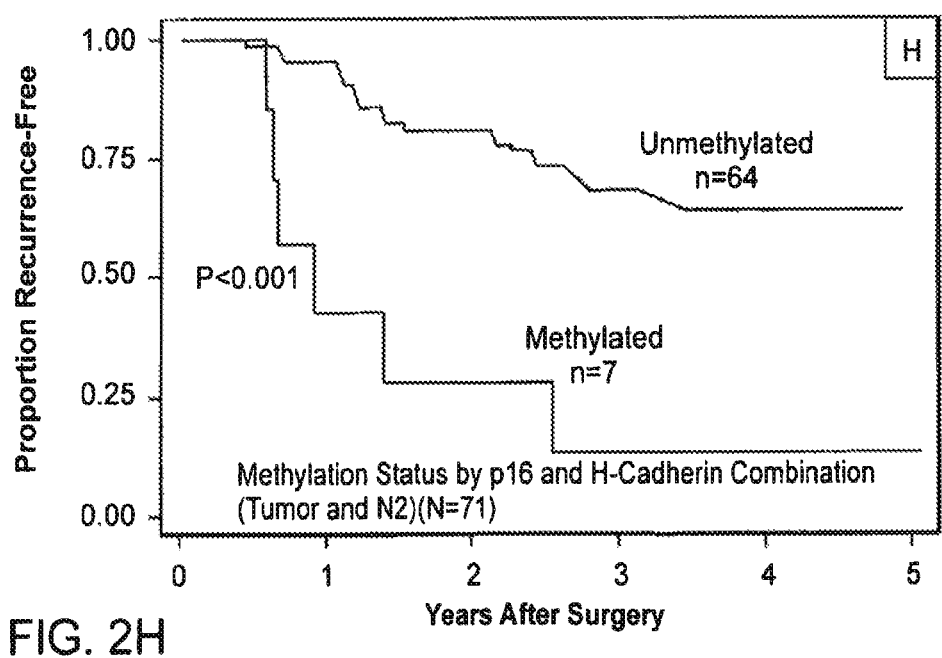
Figure 2I:
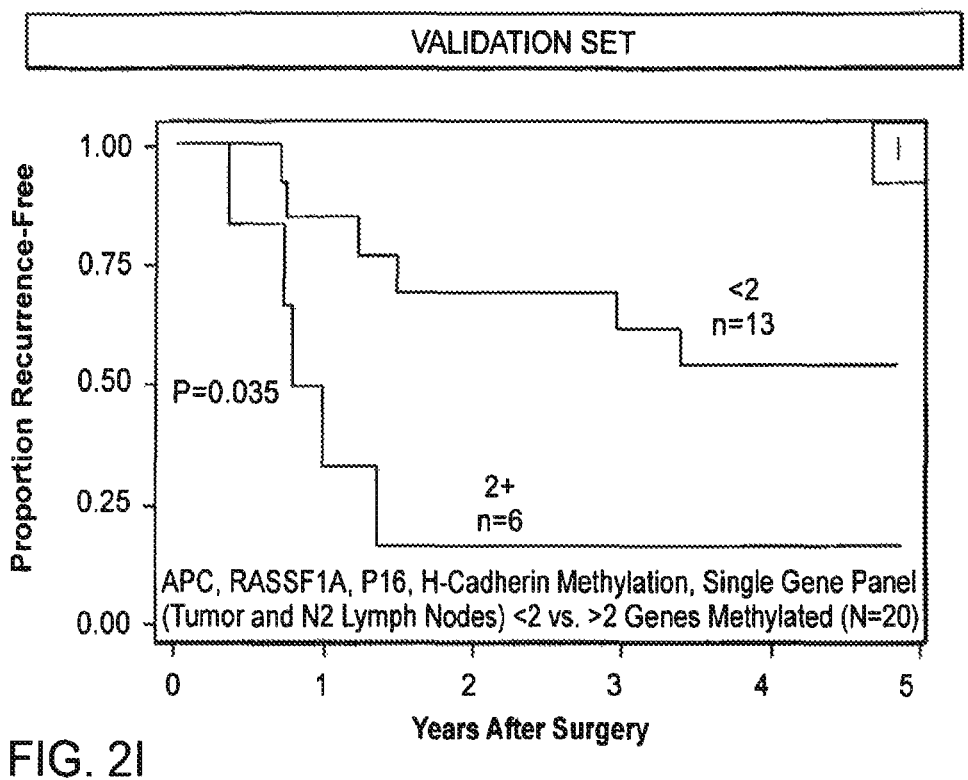
Figure 2J:
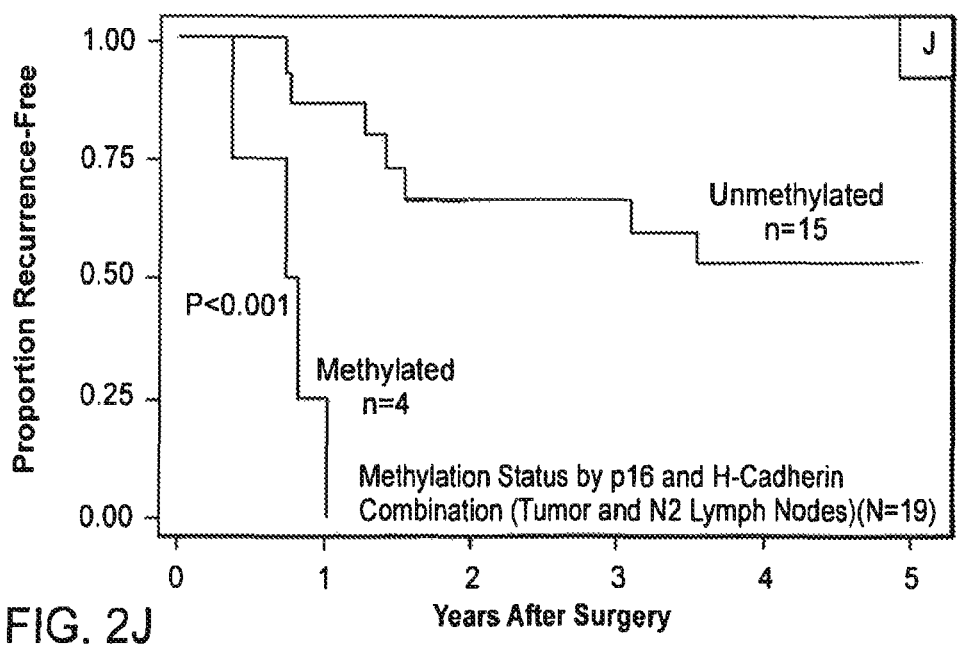
Figure 2K:
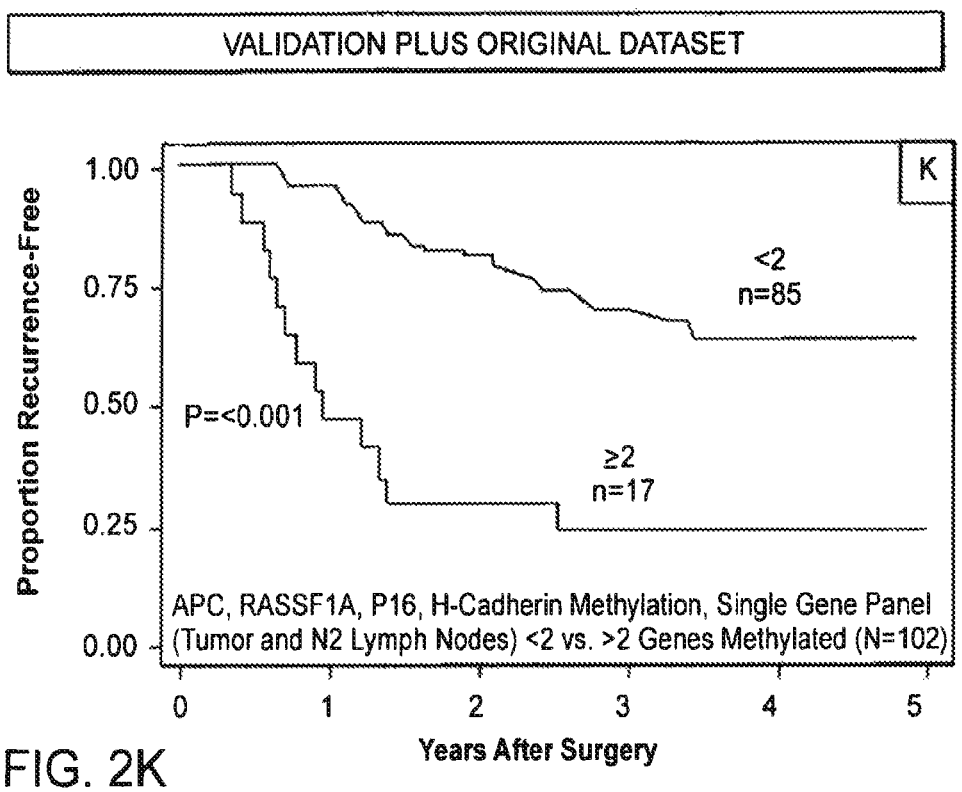
Figure 2L:
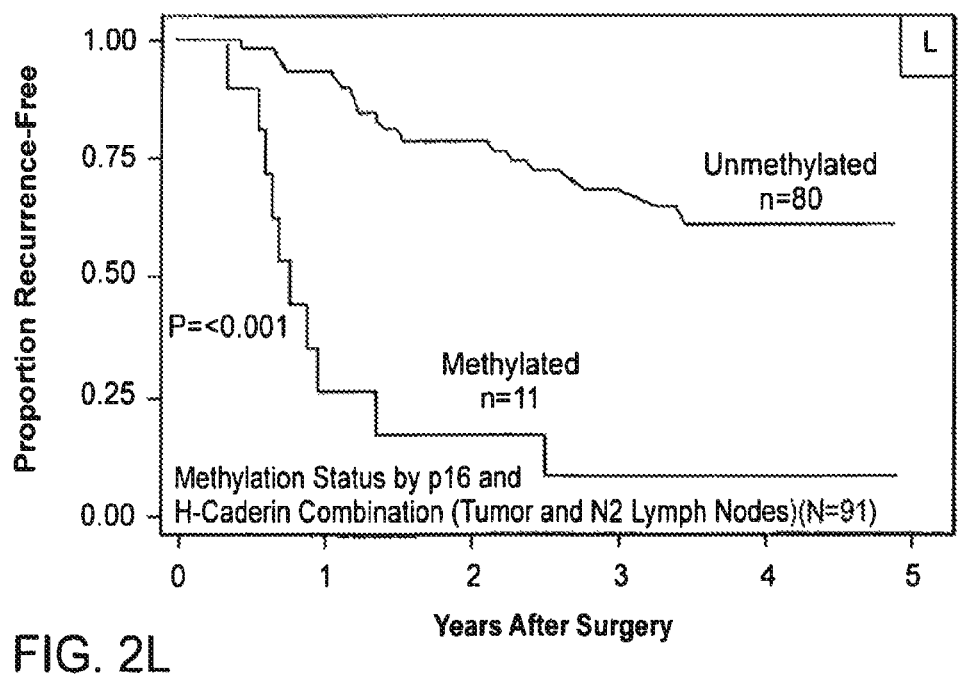

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "control" is meant a standard or reference condition.

The phrase "in combination with" is intended to refer to all forms of administration that provide a de-methylating agent, or the methods of the instant invention (e.g. methods of detection of hypermethylation) together with a second agent, such as a chemotherapeutic agent, or a de-methylating agent, where the two are administered concurrently or sequentially in any order.

The term "agent" as used herein is meant to refer to a polypeptide, polynucleotide, or fragment, or analog thereof, small molecule, or other biologically active molecule.

The term "CpG island" refers to a sequence of nucleic acid with an increased density relative to other nucleic acid regions of the dinucleotide CpG.

The term "epigenetic marker" or "epigenetic change" as used herein is meant to refer to a change in the DNA sequences or gene expression by a process or processes that do not change the DNA coding sequence itself. In an exemplary embodiment, methylation is an epigenetic marker.

The term "hypermethylation" as used herein refers to the presence of methylated alleles in one or more nucleic acids. In preferred embodiments, hypermethylation is detected using methylation specific polymerase chain reaction (MSP).

The term "metastases" is meant to refer to the spread of a malignant tumor from its sight of origin. Cancer cells may metastasize through the bloodstream, through the lymphatic system, across body cavities, or any combination thereof. A metastatic tumor can arise from a multitude of primary tumor types, including but not limited to lung, breast, thyroid, head and neck, brain, lymphoid, gastrointestinal (mouth, esophagus, stomach, small intestine, colon, rectum), genito-urinary tract (uterus, ovary, cervix, bladder, testicle, penis, prostate), kidney, pancreas, liver, bone, muscle or skin.

The term "micrometastases" is meant to refer to a metastasis that cannot be detected by routine histological evaluation, for example by Hematoxylin and Eosin (H & E) staining and microscopic assessment.

The term "neoplasm" or "neoplasia" as used herein refers to inappropriately high levels of cell division, inappropriately low levels of apoptosis, or both. A neoplasm creates an unstructured mass (a tumor), which can be either benign or malignant. For example, cancer is a neoplasia. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). Lymphoproliferative disorders are also considered to be proliferative diseases.

The phrase "nucleic acid" as used herein refers to an oligonucleotide, nucleotide, polynucleotide, or to a fragment of any of these, to DNA or RNA of genomic or synthetic origin which may be single-stranded or double-stranded and may represent a sense or antisense strand, peptide nucleic acid (PNA), or to any DNA-like or RNA-like material, natural or synthetic in origin. As will be understood by those of skill in the art, when the nucleic acid is RNA, the deoxynucleotides A, G, C, and T are replaced by ribonucleotides A, G, C, and U, respectively.

The term "proliferative disorder" as used herein refers to an abnormal growth of cells. A cell proliferative disorder as described herein may be a neoplasm.

The term "promoter" or "promoter region" refers to a minimal sequence sufficient to direct transcription or to render promoter-dependent gene expression that is controllable for cell-type specific, tissue-specific, or is inducible by external signals or agents. Promoters may be located in the 5' or 3' regions of the gene. Promoter regions, in whole or in part, of a number of nucleic acids can be examined for sites of CpG-island methylation.

The term "sample" as used herein refers to any biological or chemical mixture for use in the method of the invention. The sample can be a biological sample. The biological samples are generally derived from a patient, preferably as a bodily fluid (such as tumor tissue, lymph node, sputum, blood, bone marrow, cerebrospinal fluid, phlegm, saliva, or urine) or cell lysate. The cell lysate can be prepared from a tissue sample (e.g. a tissue sample obtained by biopsy), for example, a tissue sample (e.g. a tissue sample obtained by biopsy), blood, cerebrospinal fluid, phlegm, saliva, urine, or the sample can be cell lysate.

The term "stage" or "staging" as used herein is meant to refer to the extent or progression of proliferative disease, e.g. cancer, in a subject. Staging can be "clinical" and is according to the "stage classification" corresponding to the TNM classification ("Rinsho, Byori, Genpatsusei Kangan Toriatsukaikiyaku (Clinical and Pathological Codes for Handling Primary Liver Cancer)": 22p. Nihon Kangangaku Kenkyukai (Liver Cancer Study Group of Japan) edition (3rd revised edition), Kanehara Shuppan, 1992). Staging in certain embodiments can refer to "molecular staging" as defined by nucleic acid hypermethylation of one or more genes in one or more samples. In preferred embodiments of the invention, the "molecular stage" stage of a cancer is determined by detection of nucleic acid hypermethylation of one or more genes in a sample from the lymph nodes.

The term "subject" as used herein is meant to include vertebrates, preferably a mammal. Mammals include, but are not limited to, humans.

The term "tumor" as used herein is intended to include an abnormal mass or growth of cells or tissue. A tumor can be benign or malignant.

DETAILED DESCRIPTION OF THE INVENTION

The invention is based upon the discovery that the hypermethylation of certain genes can serve as prognostic and diagnostic markers for cellular proliferative disorders. This is the first time that promoter hypermethylation of certain genes, such as p16, H-cadherin, RASSf1A and APC, in the lymph nodes has been associated with the ability to predict recurrence and aggressiveness of certain cancers, such as lung cancer.

I. Detection of Methylation

DNA methylases transfer methyl groups from the universal methyl donor S-adenosyl methionine to specific sites on the DNA. Several biological functions have been attributed to the methylated bases in DNA. The most established biological function for methylated DNA is the protection of DNA from digestion by cognate restriction enzymes. The restriction modification phenomenon has, so far, been observed only in bacteria. Mammalian cells, however, possess a different methylase that exclusively methylates cytosine residues that are 5' neighbors of guanine (CpG). This modification of cytosine residues has important regulatory effects on gene expression, especially when involving CpG rich areas, known as CpG islands, located in the promoter regions of many genes.

Methylation has been shown by several lines of evidence to play a role in gene activity, cell differentiation, tumorigenesis, X-chromosome inactivation, genomic imprinting and other major biological processes (Razin, A., H., and Riggs, R. D. eds. in DNA Methylation Biochemistry and Biological Significance, Springer-Verlag, New York, 1984). In eukaryotic cells, methylation of cytosine residues that are immediately 5' to a guanosine, occurs predominantly in CG poor regions (Bird, A., Nature, 321:209, 1986). In contrast, CpG islands remain unmethylated in normal cells, except during X-chromosome inactivation and parental specific imprinting (Li, et al., Nature, 366:362, 1993) where methylation of 5' regulatory regions can lead to transcriptional repression. De novo methylation of the Rb gene has been demonstrated in a small fraction of retinoblastomas (Sakai, et al., Am. J. Hum. Genet., 48:880, 1991), and recently, a more detailed analysis of the VHL gene showed aberrant methylation in a subset of sporadic renal cell carcinomas (Herman, et al., Proc. Natl. Acad. Sci., U.S.A., 91:9700, 1994). Expression of a tumor suppressor gene can also be abolished by de novo DNA methylation of a normally unmethylated CpG island (Issa, et al., Nature Genet., 7:536, 1994; Herman, et al., supra; Merlo, et al., Nature Med., 1:686, 1995; Herman, et al., Cancer Res., 56:722, 1996; Graff, et al., Cancer Res., 55:5195, 1995; Herman, et al., Cancer Res., 55:4525, 1995).

In higher order eukaryotes DNA is methylated only at cytosines located 5' to guanosine in the CpG dinucleotide. This modification has important regulatory effects on gene expression, especially when involving CpG rich areas, known as CpG islands, located in the promoter regions of many genes. While almost all gene-associated islands are protected from methylation on autosomal chromosomes, extensive methylation of CpG islands has been associated with transcriptional inactivation of selected imprinted genes and genes on the inactive X-chromosome of females. Aberrant methylation of normally unmethylated CpG islands has been described as a frequent event in immortalized and transformed cells, and has been associated with transcriptional inactivation of defined tumor suppressor genes in human cancers.

Any method that is sufficient to detect hypermethylation, e.g. a method that can detect methylation of nucleotides at levels as low as 0.1%, is a suitable for use in the methods of the invention. A number of different methods can be used to detect hypermethylation.

The ability to monitor the real-time progress of the PCR changes the way one approaches PCR-based quantification of DNA and RNA. Reactions are characterized by the point in time during cycling when amplification of a PCR product is first detected rather than the amount of PCR product accumulated after a fixed number of cycles. The higher the starting copy number of the nucleic acid target, the sooner a significant increase in fluorescence is observed. An amplification plot is the plot of fluorescence signal versus cycle number. In the initial cycles of PCR, there is little change in fluorescence signal. This defines the baseline for the amplification plot. An increase in fluorescence above the baseline indicates the detection of accumulated PCR product. A fixed fluorescence threshold can be set above the baseline. The parameter $C_T$ (threshold cycle) is defined as the fractional cycle number at which the fluorescence passes the fixed threshold. For example, the PCR cycle number at which fluorescence reaches a threshold value of 10 times the standard deviation of baseline emission may be used as $C_T$ and it is inversely proportional to the starting amount of target cDNA. A plot of the log of initial target copy number for a set of standards versus $C_T$ is a straight line. Quantification of the amount of target in unknown samples is accomplished by measuring $C_T$ and using the standard curve to determine starting copy number.

The entire process of calculating $C_{TS}$, preparing a standard curve, and determining starting copy number for unknowns can be performed by software, for example that of the 7700 system or 7900 system of Applied Biosystems. Real-time PCR requires an instrumentation platform that consists of a thermal cycler, computer, optics for fluorescence excitation and emission collection, and data acquisition and analysis software. These machines, available from several manufacturers, differ in sample capacity (some are 96-well standard format, others process fewer samples or require specialized glass capillary tubes), method of excitation (some use lasers, others broad spectrum light sources with tunable filters), and overall sensitivity. There are also platform-specific differences in how the software processes data. Real-time PCR machines are available at core facilities or labs that have the need for high throughput quantitative analysis.

Briefly, in the Q-PCR method the number of target gene copies can be extrapolated from a standard curve equation using the absolute quantitation method. For each gene, cDNA from a positive control is first generated from RNA by the reverse transcription reaction. Using about 1 μl of this cDNA, the gene under investigation is amplified using the primers by means of a standard PCR reaction. The amount of amplicon obtained is then quantified by spectrophotometry and the number of copies calculated on the basis of the molecular weight of each individual gene amplicon. Serial dilutions of this amplicon are tested with the Q-PCR assay to generate the gene specific standard curve. Optimal standard curves are based on PCR amplification efficiency from 90 to 100% (100% meaning that the amount of template is doubled after each cycle), as demonstrated by the slope of the standard curve equation. Linear regression analysis of all standard curves should show a high correlation ($R^2$ coefficient .gtoreq.0.98). Genomic DNA can be similarly quantified.

When measuring transcripts of a target gene, the starting material, transcripts of a housekeeping gene are quantified as an endogenous control. Beta-actin is one of the most used nonspecific housekeeping genes. For each experimental sample, the value of both the target and the housekeeping gene are extrapolated from the respective standard curve. The target value is then divided by the endogenous reference value to obtain a normalized target value independent of the amount of starting material.

The above-described quantitative real-time PCR methodology has been adapted to perform quantitative methylation-specific PCR (QM-MSP) by utilizing the external primers pairs in round one (multiplex) PCR and internal primer pairs in round two (real time MSP) PCR. Thus each set of genes has one pair of external primers and two sets of three internal primers/probe (internal sets are specific for unmethylated or methylated DNA). The external primer pairs can co-amplify a cocktail of genes, each pair selectively hybridizing to a member of the panel of genes being investigated using the invention method. The method of methylation-specific PCR (QM-MSP) has been described in US Patent Application 20050239101, incorporated by reference in its entirety herein.

Hypermethylation can be detected using two-stage, or "nested" PCR, for example as described in U.S. Pat. No. 7,214,485, incorporated by reference in its entirety herein. For example, two-stage, or "nested" polymerase chain reaction method is disclosed for detecting methylated DNA sequences at sufficiently high levels of sensitivity to permit cancer screening in biological fluid samples, such as sputum, obtained non-invasively.

A method for assessment of the methylation status of any group of CpG sites within a CpG island, independent of the use of methylation-sensitive restriction enzymes, is described in U.S. Pat. No. 6,017,704 incorporated by reference in its entirety herein and described briefly as follows. This method employs primers that specific for the bisulfite reaction such that the PCR reaction itself is used to distinguish between the chemically modified methylated and unmethylated DNA, which adds an improved sensitivity of methylation detection. Unlike previous genomic sequencing methods for methylation identification which utilizes amplification primers which are specifically designed to avoid the CpG sequences, MSP primers themselves are specifically designed to recognize CpG sites to take advantage of the differences in methylation to amplify specific products to be identified by the invention assay. The methods of MSP include modification of DNA by sodium bisulfite or a comparable agent that converts all unmethylated but not methylated cytosines to uracil, and subsequent amplification with primers specific for methylated versus unmethylated DNA. This method of "methylation specific PCR" or MSP, requires only small amounts of DNA, is sensitive to 0.1% of methylated alleles of a given CpG island locus, and can be performed on DNA extracted from paraffin-embedded samples, for example. In addition, MSP eliminates the false positive results inherent to previous PCR-based approaches which relied on differential restriction enzyme cleavage to distinguish methylated from unmethylated DNA.

MSP provides significant advantages over previous PCR and other methods used for assaying methylation. MSP is markedly more sensitive than Southern analyses, facilitating detection of low numbers of methylated alleles and the study of DNA from small samples. MSP allows the study of paraffin-embedded materials, which could not previously be analyzed by Southern analysis. MSP also allows examination of all CpG sites, not just those within sequences recognized by methylation-sensitive restriction enzymes. This markedly increases the number of such sites which can be assessed and will allow rapid, fine mapping of methylation patterns throughout CpG rich regions. MSP also eliminates the frequent false positive results due to partial digestion of methylation-sensitive enzymes inherent in previous PCR methods for detecting methylation. Furthermore, with MSP, simultaneous detection of unmethylated and methylated products in a single sample confirms the integrity of DNA as a template for PCR and allows a semi-quantitative assessment of allele types which correlates with results of Southern analysis. Finally, the ability to validate the amplified product by differential restriction patterns is an additional advantage.

MSP can provide similar information as genomic sequencing, but can be performed with some advantages as follows. MSP is simpler and requires less time than genomic sequencing, with a typical PCR and gel analysis taking 4-6 hours. In contrast, genomic sequencing, amplification, cloning, and subsequent sequencing may take days. MSP also avoids the use of expensive sequencing reagents and the use of radioactivity. Both of these factors make MSP better suited for the analysis of large numbers of samples. The use of PCR as the step to distinguish methylated from unmethylated DNA in MSP allows for significant increase in the sensitivity of methylation detection. For example, if cloning is not used prior to genomic sequencing of the DNA, less than 10% methylated DNA in a background of unmethylated DNA cannot be seen (Myohanen, et al., supra). The use of PCR and cloning does allow sensitive detection of methylation patterns in very small amounts of DNA by genomic sequencing (Frommer, et al., Proc. Natl. Acad. Sci. USA, 89:1827, 1992; Clark, et al., Nucleic Acids Research, 22:2990, 1994). However, this means in practice that it would require sequencing analysis of 10 clones to detect 10% methylation, 100 clones to detect 1% methylation, and to reach the level of sensitivity we have demonstrated with MSP (1:1000), one would have to sequence 1000 individual clones.

"Multiplex methylation-specific PCR" is a unique version of methylation-specific PCR. Methylation-specific PCR is described in U.S. Pat. Nos. 5,786,146; 6,200,756; 6,017,704 and 6,265,171, each of which is incorporated herein by reference in its entirety. Multiplex methylation-specific PCR utilizes MSP primers for a multiplicity of markers, for example three or more different markers, in a two-stage nested PCR amplification reaction. The primers used in the first PCR reaction are selected to amplify a larger portion of the target sequence than the primers of the second PCR reaction. The primers used in the first PCR reaction are referred to herein as "external primers" or DNA primers" and the primers used in the second PCR reaction are referred to herein as "MSP primers." Two sets of primers (i.e., methylated and unmethylated for each of the markers targeted in the reaction) are used as the MSP primers. In addition in multiplex methylation-specific PCR, as described herein, a small amount (i.e., 1 μl) of a 1:10 to about $10^6$ dilution of the reaction product of the first "external" PCR reaction is used in the second "internal" MSP PCR reaction.

The term "primer" as used herein refers to a sequence comprising two or more deoxyribonucleotides or ribonucleotides, preferably more than three, and most preferably more than 8, which sequence is capable of initiating synthesis of a primer extension product, which is substantially complementary to a polymorphic locus strand. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxy ribonucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12-20 or more nucleotides, although it may contain fewer nucleotides.

Primers of the invention are designed to be "substantially" complementary to each strand of the oligonucleotide to be amplified and include the appropriate G or C nucleotides as discussed above. This means that the primers must be sufficiently complementary to hybridize with their respective strands under conditions that allow the agent for polymerization to perform. In other words, the primers should have sufficient complementarity with a 5' and 3' oligonucleotide to hybridize therewith and permit amplification of CpG containing nucleic acid sequence.

Primers of the invention are employed in the amplification process, which is an enzymatic chain reaction that produces exponentially increasing quantities of target locus relative to the number of reaction steps involved (e.g., polymerase chain reaction or PCR). Typically, one primer is complementary to the negative (−) strand of the locus (antisense primer) and the other is complementary to the positive (+) strand (sense primer). Annealing the primers to denatured nucleic acid followed by extension with an enzyme, such as the large fragment of DNA Polymerase I (Klenow) and nucleotides, results in newly synthesized + and − strands containing the target locus sequence. Because these newly synthesized sequences are also templates, repeated cycles of denaturing, primer annealing, and extension results in exponential production of the region (i.e., the target locus sequence) defined by the primer. The product of the chain reaction is a discrete nucleic acid duplex with termini corresponding to the ends of the specific primers employed.

The oligonucleotide primers used in invention methods may be prepared using any suitable method, such as conventional phosphotriester and phosphodiester methods or automated embodiments thereof. In one such automated embodiment, diethylphos-phoramidites are used as starting materials and may be synthesized as described by Beaucage, et al. (Tetrahedron Letters, 22:1859-1862, 1981). One method for synthesizing oligonucleotides on a modified solid support is described in U.S. Pat. No. 4,458,066.

The primers used in the invention for amplification of the CpG-containing nucleic acid in the specimen, after bisulfite modification, specifically distinguish between untreated or unmodified DNA, methylated, and non-methylated DNA. MSP primers for the non-methylated DNA preferably have a T in the 3' CG pair to distinguish it from the C retained in methylated DNA, and the complement is designed for the antisense primer. MSP primers usually contain relatively few Cs or Gs in the sequence since the Cs will be absent in the sense primer and the Gs absent in the antisense primer (C becomes modified to U (uracil) which is amplified as T (thymidine) in the amplification product).

The primers of the invention embrace oligonucleotides of sufficient length and appropriate sequence so as to provide specific initiation of polymerization on a significant number of nucleic acids in the polymorphic locus. Where the nucleic acid sequence of interest contains two strands, it is necessary to separate the strands of the nucleic acid before it can be used as a template for the amplification process. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80.degree. to 105.degree C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (CSH-Quantitative Biology, 43:63, 1978) and techniques for using RecA are reviewed in C. Radding (Ann. Rev. Genetics, 16:405-437, 1982).

As described herein, any nucleic acid specimen, in purified or nonpurified form, can be utilized as the starting nucleic acid or acids, provided it contains, or is suspected of containing, the specific nucleic acid sequence containing the target locus (e.g., CpG).

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7-9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated lona-chain nucleic acid strands. A large molar excess is preferred to improve the efficiency of the process.

The deoxyribonucleoside triphosphates dATP, dCTP, dGTP, and dTTP are added to the synthesis mixture, either separately or together with the primers, in adequate amounts and the resulting solution is heated to about 90 C-100 C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40 C. Most conveniently the reaction occurs at room temperature.

In certain preferred embodiments, the agent for polymerization may be any compound or system which will function to accomplish the synthesis of primer extension products, including enzymes. Suitable enzymes for this purpose include, for example, E. coli DNA polymerase I, Klenow fragment of E. coli DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each locus nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2.times.SSC/0.1% SDS at about room temperature (hybridization conditions); 0.2.times.SSC/0.1% SDS at about room temperature (low stringency conditions); 0.2.times.SSC/0.1% SDS at about 42.degree. C. (moderate stringency conditions); and 0.1.times.SSC at about 68.degree. C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Preferably, the method of amplifying is by PCR, as described herein and as is commonly used by those of ordinary skill in the art. Alternative methods of amplification have been described and can also be employed as long as the methylated and non-methylated loci amplified by PCR using the primers of the invention is similarly amplified by the alternative means.

The amplified products are preferably identified as methylated or non-methylated by sequencing. Sequences amplified by the methods of the invention can be further evaluated, detected, cloned, sequenced, and the like, either in solution or after binding to a solid support, by any method usually applied to the detection of a specific DNA sequence such as PCR, oligomer restriction (39), allele-specific oligonucleotide (ASO) probe analysis (40), oligonucleotide ligation assays (OLAs) (41), and the like. Molecular techniques for DNA analysis have been reviewed (42).

Optionally, the methylation pattern of the nucleic acid can be confirmed by restriction enzyme digestion and Southern blot analysis. Examples of methylation sensitive restriction endonucleases which can be used to detect 5'CpG methylation include SmaI, SacII, EagI, MspI, HpaII, BstUI and BssHII, for example.

The invention provides a method for detecting a cell having a hypermethylated CpG island or a cell proliferative disorder associated with hypermethylated CpG in a tissue or biological fluid of a subject, comprising contacting a target cellular component suspected of expressing a gene having a methylated CpG or having a CpG-associated disorder, with an agent which binds to the component. The target cell component can be nucleic acid, such as DNA or RNA, or protein. When the component is nucleic acid, the reagent is a nucleic acid probe or PCR primer. When the cell component is protein, the reagent is an antibody probe. The probes can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the antibody, or will be able to ascertain such, using routine experimentation.

Actively transcribed genes generally contain fewer methylated CGs than the average number in DNA. Hypermethylation can also be detected by restriction endonuclease treatment and Southern blot analysis. Therefore, in certain preferred embodiments, when the cellular component detected is DNA, restriction endonuclease analysis is preferable to detect hypermethylation of the promoter for example. Any restriction endonuclease that includes CG as part of its recognition site and that is inhibited when the C is methylated can be utilized. In certain preferred examples, the methylation sensitive restriction endonuclease is BssHII, MspI, or HpaII, used alone or in combination. Other methylation sensitive restriction endonucleases will be known to those of skill in the art.

For purposes of the invention, an antibody or nucleic acid probe specific for a gene or gene product may be used to detect the presence of methylation either by detecting the level of polypeptide (using antibody) or methylation of the polynucleotide (using nucleic acid probe) in biological fluids or tissues. For antibody-based detection, the level of the polypeptide is compared with the level of polypeptide found in a corresponding "normal" tissue. Oligonucleotide primers based on any coding sequence region of the promoter in gene selected from genes involved in tumor suppression, nucleic acid repair, apoptosis, anti-proliferation, ras signaling, adhesion, differentiation, development, and cell cycle regulation. In particular, oligonucleotide primers are based on coding sequence region of the promoter in the gene selected from the following are useful for amplifying DNA, for example by PCR:

H-cadherin, in certain exemplary embodiments is encoded by NCBI accession No. AAB18912, comprising (SEQ ID NO:1) below:

```
  1 mqprtplvlc vllsqvlllt saedldctpg fqqkvfhinq
    paefiedqsi lnltfsdckg 61 ndklryevss pyfkvnsdgg lvalrnitav gktlfvhart
    phaedmaelv ivggkdiqgs 121 lqdifkfart spvprqkrsi vvspilipen qrqpfprdvg
    kvvdsdrper skfrltgkgv 181 dqepkgifri nentgsvsvt rtldreviav yqlfvettdv
    ngktlegpvp levividqnd 241 nrpifregpy ighvmegspt gttvmrmtaf daddpatdna
    llrynirqqt pdkpspnmfy 301 idpekgdivt vvspalldre tlenpkyeli ieaqdmagld
    vgltgtatat imiddkndhs 361 pkftkkefqa tveegavgvi vnltvedkdd pttgawraay
    tiingnpgqs feihtnpqtn 421 egmlsvvkpl dyeisafhtl likvenedpl vpdvsygpss
    tatvhitvld vnegpvfypd 481 pmmvtrqedl svgsvlltvn atdpdslqhq tirysvykdp
    agwlninpin gtvdttavld 541 respfvdnsv ytalflaids gnppatgtgt llitledvnd
    napfiyptva evcddaknls 601 vvilgasdkd lhpntdpkfk eihkqavpdk vwkiskinnt
    halvsllqnl nkanynlpim 661 vtdsgkppmt nitdlrvqvc scrnskvdcn aagalrfslp
    svlllslfsl acl
``` p-16, in certain exemplary embodiments is encoded by NCBI accession No. CAB58124 comprising (SEQ ID NO:2) below:

```
  1 gshsmryfft svsrpgrgep rfiavgyvdd tqfvrfdsda
    asqrmeprap wieqegpeyw 61 dgetrkvkah sqtdrvdlgt lrgyynqsea gshtiqmmyg
    cdvgpdgrll rgyqqdaydg 121 kdyialnedl rswtaadmaa qitqrkweaa rvaeqlrayl
    egtcvewlrr ylengketlq 181 rt
```

APC, in certain exemplary embodiments is encoded by NCBI accession No. NP_000029 comprising (SEQ ID NO:3) below:

```
   1 maaasydqll kqvealkmen snlrqeledn snhltklete
     asnmkevlkq lqgsiedeam 61 assgqidlle rlkelnldss nfpgvklrsk mslrsygsre
     gsvssrsgec spvpmgsfpr 121 rgfvngsres tgyleeleke rsllladldk eekekdwyya
     qlqnltkrid slpltenfsl 181 qtdmtrrqle yearqirvam eeqlgtcqdm ekraqrriar
     iqqiekdilr irqllqsqat 241 eaerssqnkh etgshdaerq negqgvgein matsgngqgs
     ttrmdhetas vlssssthsa 301 prrltshlgt kvemvyslls mlgthdkddm srtllamsss
     qdscismrqs gclplliqll 361 hgndkdsvll gnsrgskear arasaalhni ihsqpddkrg
     rreirvlhll eqiraycetc 421 wewqeahepg mdqdknpmpa pvehqicpav cvlmklsfde
     ehrhamnelg glqaiaellq 481 vdcemygltn dhysitlrry agmaltnltf gdvankatlc
     smkgcmralv aqlksesedl 541 qqviasvlrn lswradvnsk ktlrevgsvk almecalevk
     kestlksvls alwnlsahct 601 enkadicavd galaflvgtl tyrsqtntla iiesgggilr
     nvssliatne dhrqilrenn 661 clqtllqhlk shsltivsna cgtlwnlsar npkdqealwd
     mgavsmlknl ihskhkmiam 721 gsaaalrnlm anrpakykda nimspgsslp slhvrkqkal
     eaeldaqhls etfdnidnls 781 pkashrskqr hkqslygdyv fdtnrhddnr sdnfntgnmt
     vlspylnttv lpsssssrgs 841 ldssrsekdr slerergigl gnyhpatenp gtsskrglqi
     sttaaqiakv meevsaihts 901 qedrssgstt elhcvtdern alrrssaaht hsntynftks
     ensnrtcsmp yakleykrss 961 ndslnsvsss dgygkrgqmk psiesysedd eskfcsygqy
     padlahkihs anhmddndge 1021 ldtpinyslk ysdeqlnsgr qspsqnerwa rpkhiiedei
     kqseqrqsrn qsttypvyte 1081 stddkhlkfq phfgqqecvs pyrsrgangs etnrvgsnhg
     inqnvsqslc qeddyeddkp 1141 tnyserysee eqheeeerpt nysikyneek rhvdqpidys
     lkyatdipss qkqsfsfsks 1201 ssgqsskteh mssssentst pssnakrqnq lhpssaqsrs
     gqpqkaatck vssinqetiq 1261 tycvedtpic fsrcsslssl ssaedeigcn qttqeadsan
     tlqiaeikek igtrsaedpv 1321 sevpavsqhp rtkssrlqgs slssesarhk avefssgaks
     psksgaqtpk sppehyvqet 1381 plmfsrctsv ssldsfesrs iassvqsepc sgmvsgiisp
     sdlpdspgqt mppsrsktpp 1441 pppqtaqtkr evpknkapta ekresgpkqa avnaavqrvq
     vlpdadtllh fatestpdgf
```

```
1501  scssslsals  ldepfiqkdv  elrimppvqe  ndngnetese
      qpkesnenqe  keaektidse 1561  kdllddsddd  dieileecii  samptkssrk  akkpaqtask
      lpppvarkps  qlpvykllps 1621  qnrlqpqkhv  sftpgddmpr  vycvegtpin  fstatslsdl
      tiesppnela  agegvrggaq 1681  sgefekrdti  ptegrstdea  qggktssvti  pelddnkaee
      gdilaecins  ampkgkshkp 1741  frvkkimdqv  qqasasssap  nknqldgkkk  kptspvkpip
      qnteyrtrvr  knadsknnln 1801  aervfsdnkd  skkqnlknns  kvfndklpnn  edrvrgsfaf
      dsphhytpie  gtpycfsrnd 1861  slssldfddd  dvdlsrekae  lrkakenkes  eakvtshtel
      tsnqqsankt  qaiakqpinr 1921  gqpkpilqkq  stfpqsskdi  pdrgaatdek  lqnfaientp
      vcfshnssls  slsdidqenn 1981  nkenepiket  eppdsqgeps  kpqasgyapk  sfhvedtpvc
      fsrnsslssl  sidseddllq 2041  ecissampkk  kkpsrlkgdn  ekhsprnmgg  ilgedltldl
      kdiqrpdseh  glspdsenfd 2101  wkaiqegans  ivsslhqaaa  aaclsrqass  dsdsilslks
      gislgspfhl  tpdqeekpft 2161  snkgprilkp  gekstletkk  ieseskgikg  gkkvykslit
      gkvrsnseis  gqmkqplqan 2221  mpsisrgrtm  ihipgvrnss  sstspvskkg  pplktpasks
      psegqtatts  prgakpsvks 2281  elspvarqts  qiggsskaps  rsgsrdstps  rpaqqplsrp
      iqspgrnsis  pgrngisppn 2341  klsqlprtss  pstastkssg  sgkmsytspg  rqmsqqnltk
      qtglsknass  iprsesaskg 2401  lnqmnngnga  nkkvelsrms  stkssgsesd  rserpvlvrq
      stfikeapsp  tlrrkleesa 2461  sfeslspssr  pasptrsqaq  tpvlspslpd  mslsthssvq
      aggwrklppn  lsptieyndg 2521  rpakrhdiar  shsespsrlp  inrsgtwkre  hskhssslpr
      vstwrrtgss  ssilsasses 2581  sekaksedek  hvnsisgtkq  skenqvsakg  twrkikenef
      sptnstsqtv  ssgatngaes 2641  ktliyqmapa  vsktedvwvr  iedcpinnpr  sgrsptgntp
      pvidsvseka  npnikdskdn 2701  qakqnvgngs  vpmrtvglen  rlnsfiqvda  pdqkgteikp
      gqnnpvpvse  tnessivert 2761  pfssssskkh  sspsgtvaar  vtpfnynpsp  rkssadstsa
      rpsqiptpvn  nntkkrdskt 2821  dstessgtqs  pkrhsgsylv  tsv
```

RASSF1A, in certain exemplary embodiments is encoded by NCBI accession No. NP_009113 comprising (SEQ ID NO:4) below:

```
  1  msgepeliel  relapagrag  kgrtrleran  alriargtac
     nptrqlvpgr  ghrfqpagpa 61  thtwcdlcgd  fiwgvvrkgl  qcahckftch  yrcralvcld
     ccgprdlgwe  paverdtnvd
```

```
121  epvewetpdl  sqaeieqkik  eynaqinsnl  fmslnkdgsy
     tgfikvqlkl  vrpvsvpssk 181  kppslqdarr  gpgrgtsvrr  rtsfylpkda  vkhlhvlsrt
     rarevieall  rkflvvddpr 241  kfalferaer  hgqvylrkll  ddeqplrlrl  lagpsdkals
     fvlkendsge  vnwdafsmpe 301  lhnflrilqr  eeeehlrqil  qkysycrqki  qealhacplg
```

MGMT, in certain exemplary embodiments is encoded by NCBI accession No. AAH00824 comprising (SEQ ID NO:5) below:

```
  1  mdkdcemkrt  tldsplgkle  lsgceqglhe  ikllgkgtsa
     adavevpapa  avlggpeplm 61  qctawlnayf  hqpeaieefp  vpalhhpvfq  qesftrqvlw
     kllkvvkfge  visyqqlaal 121  agnpkaarav  ggamrgnpvp  ilipchrvvc  ssgavgnysg
     glavkewlla  heghrlgkpg 181  lggssglaga  wlkgagatsg  sppagrn
```

DAPK, in certain exemplary embodiments is encoded by NCBI accession No. NP_004929 comprising (SEQ ID NO:6) below:

```
  1  mtvfrqenvd  dyydtgeelg  sgqfavvkkc  rekstglqya
     akfikkrrtk  ssrrgvsred 61  ierevsilke  iqhpnvitlh  evyenktdvi  lilelvagge
     lfdflaekes  lteeeatefl 121  kqilngvyyl  hslqiahfdl  kpenimlldr  nvpkprikii
     dfglahkidf  gnefknifgt 181  pefvapeivn  yeplgleadm  wsigvityil  lsgaspflgd
     tkqetlanvs  avnyefedey 241  fsntsalakd  firrllvkdp  kkrmtiqdsl  qhpwikpkdt
     qqalsrkasa  vnmekfkkfa 301  arkkwkqsvr  lislcqrlsr  sflsrsnmsv  arsddtldee
     dsfvmkaiih  ainddnvpgl 361  qhllgslsny  dvnqpnkhgt  pplliaagcg  niqilqllik
     rgsridvqdk  ggsnavywaa 421  rhghvdtlkf  lsenkcpldv  kdksgemalh  vaaryghadv
     aqllcsfgsn  pniqdkeeet 481  plhcaawhgy  ysvakalcea  gcnvniknre  getplltasa
     rgyhdivecl  aehgadlnac 541  dkdghialhl  avrrcqmevi  ktllsqgcfv  dyqdrhgntp
     lhvackdgnm  pivvalcean 601  cnldisnkyg  rtplhlaann  gildvvrylc  lmgasvealt
     tdgktaedla  rseqhehvag 661  llarlrkdth  rglfiqqlrp  tqnlqprikl  klfghsgsgk
     ttlveslkcg  llrsffrrrr 721  prlsstnssr  fppsplaskp  tvsvsinnly  pgcenvsvrs
     rsmmfepglt  kgmlevfvap 781  thhphcsadd  qstkaidiqn  aylngvgdfs  vwefsgnpvy
     fccydyfaan  dptsihvvvf 841  sleepyeiql  nqvifwlsfl  kslvpveepi  afggklknpl
     qvvlvathad  imnvprpagg 901  efgydkdtsl  lkeirnrfgn  dlhisnklfv  ldagasgskd
     mkvlrnhlqe  irsqivsvcp
```

```
 961 pmthlcekii stlpswrkln gpnqlmslqq fvydvqdqln
     plaseedlrr iaqqlhstge 1021 inimqsetvq dvllldprwl ctnvlgklls vetpralhhy
     rgrytvediq rlvpdsdvee 1081 llqildamdi cardlssgtm vdvpaliktd nlhrswadee
     devmvyggvr ivpvehltpf 1141 pcgifhkvqv nlcrwihqqs tegdadirlw vngcklanrg
     aellvllvnh gqgievqvrg 1201 letekikccl lldsvcstie nvmattlpgl ltvkhylspq
     qlrehhepvm iyqprdffra 1261 qtlketsltn tmggykesfs simcfgchdv ysqaslgmdi
     hasdlnlltr rklsrlldpp 1321 dplgkdwcll amnlglpdlv akyntsngap kdflpsplha
     llrewttype stvgtlmskl 1381 relgrrdaad fllkassvfk inldgngqea yasscnsgts
     ynsissvvsr
```

ASC, in certain exemplary embodiments is encoded by NCBI accession No. NP_037390 comprising (SEQ ID NO:7) below:

```
  1 mgrardaild alenltaeel kkfklkllsv plregygrip
    rgallsmdal dltdklvsfy 61 letygaelta nvlrdmglqe magqlqaath qgsgaapagi
    qappqsaakp glhfidqhra 121 aliarvtnve wlldalygkv ltdeqyqavr aeptnpskmr
    klfsftpawn wtckdlllqa 181 lresqsylve dlers
```

These genes are merely listed as examples and are not meant to be limiting.

In certain preferred embodiments of the invention the genes can be detected in panels consisting of the following:
(1) genes involved in tumor suppression and cell adhesion
(2) genes involved in cell cycle regulation and adhesion
(3) genes involved in tumor suppression and cell cycle regulation
(4) genes involved in ras signaling and cell cycle control.

Any specimen containing a detectable amount of polynucleotide or antigen can be used. Preferably the subject is human.

The present invention provides the finding that gene hypermethylation of not only the primary malignancy, but also lymph nodes, may be used to restage and assess prognosis of patients with stage I tumors, in particular examples patients with stage I non small cell lung carcinoma (NSCLC). These markers are shown to also be potential targets for reversal of gene silencing and may be important in adjuvant approaches to reduce disease recurrence.

Using the methods of the invention, expression of any gene, such as genes involved in tumor suppression, nucleic acid repair, apoptosis, anti-proliferation, ras signaling, adhesion, differentiation, development, and cell cycle regulation, can be identified in a cell and the appropriate course of treatment can be employed (e.g., sense gene therapy or drug therapy). The expression pattern of the gene may vary with the stage of malignancy of a cell, therefore, a sample such as NSCLC or breast tissue can be screened with a panel of gene or gene product specific reagents (i.e., nucleic acid probes or antibodies) to detect gene expression and then diagnose the stage of malignancy of the cell.

Any of the methods as described herein can be used in high throughput analysis of DNA methylation. For example, U.S. Pat. No. 7,144,701, incorporated by reference in its entirety herein, describes differential methylation hybridization (DMH) for a high-throughput analysis of DNA methylation.

II. Methods of Detection and Diagnosis

The methods of the invention as described herein are used in certain exemplary embodiments to identify metastases by detecting hypermethylation of one or more genes in one or more samples. In this way, the detection of nucleic acid hypermethylation identifies metastases.

In mammals, conditions associated with aberrant methylation of genes that can be detected or monitored include, but are not limited to, metastases associated with carcinomas and sarcomas of all kinds, including one or more specific types of cancer, e.g., a lung cancer, breast cancer, an alimentary or gastrointestinal tract cancer such as colon, esophageal and pancreatic cancer, a liver cancer, a skin cancer, an ovarian cancer, an endometrial cancer, a prostate cancer, a lymphoma, hematopoietic tumors, such as a leukemia, a kidney cancer, a bronchial cancer, a muscle cancer, a bone cancer, a bladder cancer or a brain cancer, such as astrocytoma, anaplastic astrocytoma, glioblastoma, medulloblastoma, and neuroblastoma and their metastases. Suitable pre-malignant lesions to be detected or monitored using the invention include, but are not limited to, lobular carcinoma in situ and ductal carcinoma in situ.

The invention methods can be used to assay the DNA of any mammalian subject, including, but not limited to, humans, pet (e.g., dogs, cats, ferrets) and farm animals (meat and dairy).

The invention features in certain aspects a method for identifying metastases in a subject comprising detecting nucleic acid hypermethylation of one or more genes in one or more samples, wherein detecting nucleic acid hypermethylation identifies metastases. The term "hypermethylation" as used herein refers to the presence of methylated alleles in one or more nucleic acids. In preferred embodiments, hypermethylation is detected using methylation specific polymerase chain reaction (MSP).

The samples, in certain embodiments, can be from tumor tissue, lymph nodes, bone marrow or blood. Thus, the invention can be used to identify metastases in a subject comprising detecting nucleic acid hypermethylation of one or more genes in tumor tissues or in lymph nodes, wherein detecting nucleic acid hypermethylation identifies metastases. Hypermethylation can be detected in tumor tissue alone, e.g. primary tumor tissue, or tumor tissue and lymph nodes. In certain preferred embodiments, detection of hypermethylation in the lymph nodes indicates an early recurring disease. In other certain preferred embodiments, detection of hypermethylation in the lymph nodes indicates a more aggressive disease. Often, an early recurring disease is a more aggressive disease although the two are not mutually exclusive.

In other aspects, the invention features a method for identifying micrometastases in a subject comprising detecting nucleic acid hypermethylation of one or more genes in tumor tissue or lymph node, wherein the genes are selected from the group consisting of: genes involved in tumor suppression, DNA repair, apoptosis, anti-proliferation, ras signaling, adhesion, differentiation, development, and cell cycle regulation, in one or more cells or tissues, wherein detecting nucleic acid hypermethylation identifies micrometastases.

In other examples, the invention as described herein features a method for identifying micrometastases in a subject comprising detecting nucleic acid hypermethylation of at least one or more genes in a sample comprising tumor and lymph nodes, where the sample genes are selected from genes involved in tumor suppression, nucleic acid repair, apoptosis, anti-proliferation, ras signaling, adhesion, differentiation, development, and cell cycle regulation, in one or more cells or tissues, and where detecting nucleic acid methylation identifies micrometastases.

In practice, the method for detecting or diagnosing a proliferative disease in a subject comprises, in certain embodiments, extracting nucleic acid from one or more cell or tissue samples, detecting nucleic acid hypermethylation of one or more genes in the sample; and identifying the nucleic acid hypermethylation state of one or more genes, wherein nucleic acid hypermethylation of genes indicates a proliferative disease. In preferred examples, the proliferative disease is cancer.

As described herein, in certain preferred examples, the one or more genes comprise one or more CpG islands in the promoter regions. Accordingly, any gene that contains one or more CpG island in the promoter region is suitable for use in the methods of the invention; however in certain preferred examples, the one or more genes may be selected from any of p-16, H-cadherin, APC, RASSF1A, MGMT, DAPK, or ASC, and as described in SEQ ID NOs 1-7.

In certain embodiments, hypermethylation of at least one of the genes is detected. In other certain embodiments, hypermethylation of at least two of the genes is detected. In other certain embodiments, hypermethylation of at least three of the genes is detected.

The detection of metastases as described in these methods can be used to detect or diagnose a proliferative disease.

The detection of metastases as described in these methods can be used after surgery or therapy to treat a proliferative disease.

The detection of metastases as described in these methods can be used to predict the recurrence of a proliferative disease.

The detection of metastases as described in these methods can be used to stage a proliferative disease.

The detection of metastases as described in these methods can be used to determine a course of treatment for a subject.

These embodiments are discussed in further detail herein.

Methods of Treatment

The invention as described herein can be used to treat a subject having or at risk for having a proliferative disease, such as cancer. Accordingly, the method comprises identifying nucleic acid hypermethylation of one or more genes, where nucleic acid hypermethylation indicates having or a risk for having a proliferative disease, and administering to the subject a therapeutically effective amount of a demethylating agent, thereby treating a subject having or at risk for having a proliferative disease.

The method can be used in combination with one or more chemotherapeutic agents. Anti-cancer drugs that may be used in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine, mechlorethamine oxide hydrochloride rethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, improsulfan, benzodepa, carboquone, triethylenemelamine, triethylenephosphoramide, triethylenethiophosphoramide, trimethylolomelamine, chlornaphazine, novembichin, phenesterine, trofosfamide, estermustine, chlorozotocin, gemzar, nimustine, ranimustine, dacarbazine, mannomustine, mitobronitol, aclacinomycins, actinomycin F(1), azaserine, bleomycin, carubicin, carzinophilin, chromomycin, daunorubicin, daunomycin, 6-diazo-5-oxo-1-norleucine, doxorubicin, olivomycin, plicamycin, porfiromycin, puromycin, tubercidin, zorubicin, denopterin, pteropterin, 6-mercaptopurine, ancitabine, 6-azauridine, carmofur, cytarabine, dideoxyuridine, enocitabine, pulmozyme, aceglatone, aldophosphamide glycoside, bestrabucil, defofamide, demecolcine, elfornithine, elliptinium acetate, etoglucid, flutamide, hydroxyurea, lentinan, phenamet, podophyllinic acid, 2-ethylhydrazide, razoxane, spirogermanium, tamoxifen, taxotere, tenuazonic acid, triaziquone, 2,2',2"-trichlorotriethylamine, urethan, vinblastine, vincristine, vindesine and related agents. 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cisporphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; taxel; taxel analogues; taxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

Additional cancer therapeutics include monoclonal antibodies such as rituximab, trastuzumab and cetuximab.

Demethylating Agents

In certain embodiments, the invention features methods of identifying an agent that de-methylates hypermethylated nucleic acids comprising identifying one or more cell or tissue samples with hypermethylated nucleic acid, extracting the hypermethylated nucleic acid, contacting the nucleic acid with one or more nucleic acid de-methylating candidate agents and a control agent, and identifying the nucleic acid hypermethylation state, wherein nucleic acid de-methylation of genes in the sample by the candidate agent compared to the control indicates a demethylating agent, thereby identifying an agent that de-methylates hypermethylated nucleic acid.

III. Methods of Predicting Disease Recurrence

In other certain aspects, the invention features methods for predicting the recurrence of proliferative diseases, e.g. cancer.

Accordingly, the invention features methods for predicting the recurrence of a proliferative disease in a subject comprising detecting nucleic acid hypermethylation of one or more genes wherein detecting nucleic acid hypermethylation of one or more genes is a predictor of the recurrence of a proliferative disease.

In certain preferred embodiments, the method comprises extracting nucleic acid from one or more cell or tissue samples, detecting nucleic acid hypermethylation of one or more genes in the sample, and identifying the nucleic acid hypermethylation state of one or more genes, wherein nucleic acid hypermethylation of genes is indicative of the recurrence of a proliferative disease.

In certain cases, the rate of recurrence of a proliferative disease can be correlated with the detection of hypermethylation in a cell or tissue sample. In certain embodiments, the cell or tissue sample is tumor tissue or lymph node. In exemplary embodiments, the rate of recurrence of a proliferative disease is more rapid when gene hypermethylation is detected in lymph node. For example, when gene hypermethylation (e.g. p16 or H-cadherin) is detected the primary tumor, the odds of recurrence may be less than when the same genes are hypermethylated in N1 lymph nodes. Moreover, if the same genes (e.g. p16 or H-cadherin) were examined for hypermethylation in the mediastinal lymph nodes, the odds of recurrence may be the greatest compared to the former tissues (primary tumor and N1 lymph nodes).

The discovery and clinical validation of markers for cancer of all types which can predict prognosis, likelihood of invasive or metastatic spread is one of the major challenges facing in the field of oncology today. Adjuvant and neoadjuvant therapy (e.g. chemotherapy) are promising treatment modalities, however although adjuvant chemotherapy has been demonstrated to improve survival, for example in node negative breast cancer patients (43), problems remain, for example in the uncertainty as to how to best identify patients whose risk of disease recurrence exceeds their risk of significant therapeutic toxicity. Thus, a need remains for methods for that enable clinical decisions on adjuvant and neoadjuvant therapy, tumor surveillance and the likelihood of disease progression based on validated tumor markers correlated with metastasis and recurrence.

In other certain aspects, the invention features a method for determining the prognosis of a subject suffering from a proliferative disease comprising: detecting nucleic acid hypermethylation of one or more genes wherein the detection of nucleic acid hypermethylation is used for determining the prognosis of a subject suffering from a proliferative disease.

The prognosis can be used by the clinician to determine the course of treatment, and to monitor the course of treatment. As is understood by the skilled practicioner, prognosis is a prediction and can change during the course of treatment.

IV. Methods of Staging

The methods of the invention as described herein are used in exemplary embodiments to stage or re-stage a proliferative disease, e.g. a neoplasia or cancer.

Staging can refer to "clinical" staging or "molecular" staging. Clinical staging describes the extent or severity of an individual's cancer based on the extent of the original (primary) tumor and the extent of spread in the body. Typically, clinical staging is used in determining a subject's course of treatment and to estimate the subject's prognosis.

The TNM system is one of the most commonly used staging systems. The formal TNM staging system, promulgated by the American Joint Committee on Cancer (AJCC), is based almost exclusively on the anatomical extent of disease, which is assessed using a combination of tumor size or depth (T), lymph node spread (N), and presence or absence of metastases (M). Since its inception in 1958, the TNM system has provided a standardized, anatomical basis for staging with several important functions. It provides a basis for prediction of survival, choice of initial treatment, stratification of patients in clinical trials, accurate communication among healthcare providers, and uniform reporting of outcomes. For most tumor types, disease burden and spread have been considered the most reliable predictors of survival and determinants of the type and intensity of therapy to be used. Less often, tumor grade, histological subtype or patient age has been added to tnm staging when the ajcc became convinced that such information would significantly improve the prediction of survival or response to therapy. In the TMJ system, a number is added to each letter to indicate the size or extent of the tumor and the extent of spread. In a primary tumor (T), the designation tx indicates that the primary tumor cannot be evaluated, T0 indicates no evidence of primary tumor, tis indicates carcinoma in situ (early cancer that has not spread to neighboring tissue) and T1, T2, T3, T4 indicates size and/or extent of the primary tumor. In the regional lymph nodes (N), NX indicates the regional lymph nodes cannot be evaluated, N0 indicates there is no regional lymph node involvement (no cancer found in the lymph nodes) and N1, N2, N3 indicates the involvement of regional lymph nodes (number and/or extent of spread). For distant metastasis (M), the designation MX indicates that distant metastasis cannot be evaluated, m0 indicates no distant metastasis (cancer has not spread to other parts of the body), M1 indicates distant metastasis (cancer has spread to distant parts of the body). Criteria for stages differ for different types of cancer. More information on clinical staging can be found on the world wide web, for example at (www)cancer.gov/cancertopics/factsheet/detection/staging.

The instant invention provides the incorporation of biomarkers into TNM staging. The instant invention provides a method of molecular staging and re-staging by determining the nucleic acid hypermethylation of one or more certain genes. The invention provides methods of molecular restaging that can be used to re-stage any cancer with metastatic capability. In preferred embodiments, hypermethylated nucleic acids are detected in the lymph nodes. By molecular staging and re-staging through the detection of hypermethylated nucleic acids in the lymph nodes, the invention provides methods of detection of early recurrence of proliferative disease, e.g. cancer, that are unable to be detected by methods of clinical staging.

For example, in certain embodiments, molecular re-staging can detect hypermethylation in lymph nodes that are have a clinical designation of N=x, meaning that there is no clinical detection of cancer in the lymph nodes.

Accordingly, molecular re-staging as described herein can predict early recurrence of cancer, and thereby detect aggressive cancers at an earlier stage in their progression.

In preferred aspects, the invention features a method for staging or re-staging a proliferative disease in a subject comprising detecting nucleic acid hypermethylation of one or more genes wherein detecting nucleic acid hypermethylation is used for staging a proliferative disease. In certain examples, the stage of proliferative disease is predictive of disease recurrence.

Determining the stage of a proliferative disease can be used by the clinician to determine the course of treatment. The terms "treat," treating," "treatment," and the like are meant to refer to reducing or ameliorating a disorder and/or symptoms associated therewith. It will be appreciated that, although not precluded, treating a disorder or condition does not require that the disorder, condition or symptoms associated therewith be completely eliminated. In certain cases, an early recurring cancer may be treated with more aggressive therapy. The term "aggressive treatment regimen" is intended to mean reducing or ameliorating a disorder and/or symptoms associated therewith with a method of treatment (e.g. combination of chemotherapeutic agents) more intensive or comprehensive than usual, for instance in dosage or extent. It will be appreciated that, although not precluded, aggressively treating a disorder or condition does not require that the disorder, condition or symptoms associated therewith be completely eliminated.

The invention also features a method for staging or re-staging a proliferative disease in a subject comprising extracting nucleic acid from one or more cell or tissue samples, detecting nucleic acid hypermethylation of one or more genes in the sample; and identifying the nucleic acid hypermethylation state of one or more genes, wherein nucleic acid hypermethylation of genes is used for staging or re-staging of a proliferative disease.

Any tissue sample is suitable for use in the methods of staging or re-staging. In preferred examples, the tissue samples are selected from tumor, lymph node, bone marrow or blood or a combination thereof. In certain preferred examples, the samples are from the lymph nodes.

The molecular grading methods as described herein cab be performed prior to or after therapeutic intervention for the proliferative disease, e.g. cancer. The therapeutic intervention can be selected from treatment with an agent or can be a surgical procedure. In this way, the methods for staging or re-staging a proliferative disease in a subject comprising detecting nucleic acid hypermethylation of one or more genes as described herein can be used as adjuvant or neoadjuvant therapy.

V. Samples

Samples for use in the methods of the invention include cells or tissues obtained from any solid tumor, samples taken from lymph nodes, from bone marrow or from blood. Additionally, the sample may be a sample that is taken from plasma, serum, sputum, or other fluid. Tumor DNA can be found in various body fluids and these fluids can potentially serve as diagnostic material.

Any nucleic acid specimen, in purified or nonpurified form, can be utilized as the starting nucleic acid or acids, provided it contains, or is suspected of containing, the specific nucleic acid sequence containing the target locus (e.g., CpG). Thus, the process may employ, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the target locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

The nucleic acid-containing sample or specimen used for detection of methylated CpG may be from any solid tumor or any source including brain, colon, urogenital, hematopoietic, thymus, testis, ovarian, uterine, prostate, breast, colon, lung and renal tissue and may be extracted by a variety of techniques such as that described by Maniatis, et al. (Molecular Cloning: A Laboratory Manual, Cold Spring Harbor, N.Y., pp 280, 281, 1982).

If the extracted sample is impure (e.g., plasma, serum, stool, ejaculate, sputum, saliva, ductal cells, nipple aspiration fluid, ductal lavage fluid, cerebrospinal fluid or blood or a sample embedded in parrafin), it may be treated before amplification with an amount of a reagent effective to open the cells, fluids, tissues, or animal cell membranes of the sample, and to expose and/or separate the strand(s) of the nucleic acid(s). This lysing and nucleic acid denaturing step to expose and separate the strands will allow amplification to occur much more readily Preferably, the method of amplifying is by PCR, as described herein and as is commonly used by those of ordinary skill in the art. However, alternative methods of amplification have been described and can also be employed. PCR techniques and many variations of PCR are known. Basic PCR techniques are described by Saiki et al. (1988 Science 239:487-491) and by U.S. Pat. Nos. 4,683,195, 4,683,202 and 4,800,159, each of which is incorporated herein by reference.

The conditions generally required for PCR include temperature, salt, cation, pH and related conditions needed for efficient copying of the master-cut fragment. PCR conditions include repeated cycles of heat denaturation (i.e. heating to at least about 95.degree. C.) and incubation at a temperature permitting primer: adaptor hybridization and copying of the master-cut DNA fragment by the amplification enzyme. Heat stable amplification enzymes like the pwo, *Thermus aquaticus* or *Thermococcus litoralis* DNA polymerases which eliminate the need to add enzyme after each denaturation cycle, are commercially available. The salt, cation, pH and related factors needed for enzymatic amplification activity are available from commercial manufacturers of amplification enzymes.

As provided herein an amplification enzyme is any enzyme which can be used for in vitro nucleic acid amplification, e.g. by the above-described procedures. Such amplification enzymes include pwo, *Escherichia coli* DNA polymerase I, Klenow fragment of *E. coli* polymerase I, T4

DNA polymerase, T7 DNA polymerase, *Thermus aquaticus* (Taq) DNA polymerase, *Thermococcus litoralis* DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, *E. coli* DNA ligase or Q.beta. replicase. Preferred amplification enzymes are the pwo and Taq polymerases. The pwo enzyme is especially preferred because of its fidelity in replicating DNA.

Once amplified, the nucleic acid can be attached to a solid support, such as a membrane, and can be hybridized with any probe of interest, to detect any nucleic acid sequence. Several membranes are known to one of skill in the art for the adhesion of nucleic acid sequences. Specific non-limiting examples of these membranes include nitrocellulose (NITROPURE®) or other membranes used in for detection of gene expression such as polyvinylchloride, diazotized paper and other commercially available membranes such as GENESCREEN®, ZETAPROBE® (Biorad), and NYTRAN® Methods for attaching nucleic acids to these membranes are well known to one of skill in the art. Alternatively, screening can be done in a liquid phase.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2.times.SSC/0.1% SDS at about room temperature (hybridization conditions); 0.2.times.SSC/0.1% SDS at about room temperature (low stringency conditions); 0.2.times.SSC/0.1% SDS at about 42.degree. C. (moderate stringency conditions); and 0.1.times.SSC at about 68.degree. C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically. In general, conditions of high stringency are used for the hybridization of the probe of interest.

The probe of interest can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the probe, or will be able to ascertain such, using routine experimentation.

VI. Kits

The methods of the invention are ideally suited for the preparation of kits.

The invention features kits for identifying the nucleic acid hypermethylation state of one or more genes comprising gene specific primers for use in polymerase chain reaction (PCR), and instructions for use.

The invention also features kits for detecting metastases by detecting nucleic acid hypermethylation of one or more genes, the kit comprising gene specific primers for use in polymerase chain reaction (PCR), and instructions for use. In preferred embodiments, the metastases are micrometastases.

As described above, the PCR, in particularly preferred examples, is methylation specific PCR (MSP).

In certain embodiments, any gene comprising one or more CpG islands in the promoter region can be detected using the kits of the invention. In certain preferred examples, the one or more genes are selected from the group consisting of genes involved in tumor suppression, nucleic acid repair, anti-proliferation, apoptosis, ras signaling, adhesion, differentiation, development, and cell cycle regulation.

In certain preferred embodiments of the invention the genes can be detected in a panel consisting of the following:
(1) genes involved in tumor suppression and cell adhesion
(2) genes involved in cell cycle regulation and adhesion
(3) genes involved in tumor suppression and cell cycle regulation
(4) genes involved in ras signaling and cell cycle control In certain examples, the genes are selected from the group consisting of: p-16, H-cadherin, APC, RASSF1A, MGMT, DAPK, and ASC The kits can be used to detect hypermethylation of at least one of the genes as described herein. In some examples, can be used to detect hypermethylation of at least two of the genes as described herein. In other examples, the kits can be used to detect hypermethylation of at least three of the genes as described herein.

The two genes can be selected from the following: p-16 and H-cadherin, H-cadherin and APC, APC and p16, or RASSf1A and p16.

Carrier means are suited for containing one or more container means such as vials, tubes, and the like, each of the container means comprising one of the separate elements to be used in the method. In view of the description provided herein of invention methods, those of skill in the art can readily determine the apportionment of the necessary reagents among the container means. For example, one of the container means can comprise a container containing gene specific primers for use in polymerase chain reaction methods of the invention. In addition, one or more container means can also be included which comprise a methylation sensitive restriction endonuclease.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

EXAMPLES

In the examples provided herein, gene hypermethylation versus traditional histopathology was tested to predict disease recurrence in solid tumors. The examples presented herein show that gene hypermethylation of not only the primary malignancy, but also lymph nodes, may be used to restage and assess prognosis of patients with stage I tumors, in particular examples patients with stage I NSCLC. These markers are shown to also be potential targets for reversal of gene silencing and may be important in adjuvant approaches to reduce disease recurrence.

Example 1: Patient Characteristics

Cases and controls were similar with respect to clinical and demographic variables, as shown in Table 1, below. By the American Society of Anesthesia Physical Status Classification, both cases and controls were equally fit for surgery. The most frequent site of recurrence was the ipsilateral chest (45%) followed by metastases to bone (14%), brain (12%) and mediastinum (12%). Although 15% of controls underwent sublobar resections, all pulmonary resections in controls were curative of cancer for the study period.

TABLE 1

Characteristics of the patients (N = 187).

| Characteristic | Recurrent Group (N = 51) | Control Group (N = 116) | Validation Group (N = 20) |
|---|---|---|---|
| Age - yr | | | |
| Median | 64 | 67 | 66 |
| Interquartile range | 58-71 | 60-72 | 57-72 |
| Sex - no. (%) | | | |
| Male | 24 (47.1) | 54 (46.6) | 8 (40.0) |
| Female | 27 (52.9) | 62 (53.4) | 12 (60.0) |
| Race - no. (%) | | | |
| Caucasian | 43 (84.3) | 96 (82.7) | 15 (75.0) |
| African-American | 6 (11.8) | 19 (16.4) | 5 (25.0) |
| Other | 2 (3.9) | 1 (0.9) | 0 (0.0) |
| Stage - no. (%) | | | |
| 1A (T1N0) | 26 (51.0) | 75 (64.7) | 9 (45.0) |
| 1B (T2N0) | 25 (49.0) | 41 (35.3) | 11 (56.0) |
| Tumor Size - no. (%) | | | |
| <3 cm | 25 (49.0) | 72 (62.1) | 13 (65.0) |
| >3 cm | 26 (51.0) | 44 (37.9) | 7 (35.0) |
| Surgical Procedure - no. (%) | | | |
| Lobectomy | 46 (90.2) | 95 (81.9) | 20 (100) |
| Pnuemonoctomy/Bilobectomy | 4 (7.8) | 4 (3.4) | 0 0.0 |
| Sublobar Resections | 1 (2.0) | 17 (14.7) | 0 0.0 |
| Histology - no. (%) | | | |
| Adenocarcinoma* | 30 (58.8) | 62 (53.5) | 15 (75.0) |
| Squamous cell | 15 (29.4) | 42 (36.2) | 4 (20.0) |
| Other | 6 (11.8) | 12 (10.3) | 1 (5.0) |
| Grade - no. (%) | | | |
| Well Differentiated | 5 (9.8) | 10 (8.6) | 2 (10.0) |
| Moderately Differentiated | 22 (43.1) | 30 (25.9) | 11 (55.0) |
| Poorly Differentiated | 20 (39.3) | 45 (38.8) | 7 (35.0) |
| Unknown | 4 (7.8) | 31 (26.7) | 0 (0.0) |
| ASA Physical Status | 3 | 3 | 3 |
| Smoking - no. (%) | | | |
| Ever | 43 (84.3) | 102 (87.9) | 29 (100) |
| Never | 8 (15.7) | 12 (10.4) | 0 (0.0) |
| Unknown | 0 (0.0) | 2 (1.7) | 0 (0.0) |

*Includes bronchioloalveolar carcinoma and adeno-squamous histologies
†Other includes large cell, basaloid, and mucoepidermoid.
ASA—American Society Anestesia Physical Status Classification
Cases were matched with controls. on age, sex, stage, and date of surgery Example 2: Risk of Recurrence—Gene Methylation Risk of Recurrence Using Clinical Predictors The clinicopathologic covariates of pathologic stage, age, sex, tumor histology, smoking, and race did not predict risk of disease recurrence in NSCLC patients with histological negative lymph nodes, as shown in Table 2, below. Pathologic tumor stage showed the strongest risk for predicting disease recurrence independent of other covariates, with patients with stage 1B disease (T2 malignancies ≥3 cm and/or visceral pleural invasion) having a 1.71 (95% CI, 0.86-3.41) fold risk for disease recurrence compared to patients with smaller sized tumors and no pleural invasion (stage 1A).

TABLE 2

Supplemental Table 2. Crude and Adjusted Odds Ratios (ORs) and 95% Confidence Limits for Risk of Recurrence for Selected Demographic Characteristics.

| Characteristic | Crude OR | 95% CL | Adjusted OR* | 95% CL |
|---|---|---|---|---|
| Stage | | | | |
| 1A | 1.00 | — | 1.00 | — |
| 1B | 1.76 | 0.90-3.43 | 1.71 | 0.86-3.41 |
| Age, continuous | 0.98 | 0.94-1.01 | 0.97 | 0.94-1.01 |
| Sex | | | | |
| Female | 1.00 | — | 1.00 | — |
| Male | 1.02 | 0.53-1.97 | 0.98 | 0.49-1.96 |
| Race | | | | |
| Caucasian | 1.00 | — | 1.00 | — |
| African American | 0.89 | 0.36-2.19 | 0.84 | 0.33-2.12 |
| Histology | | | | |
| Adenocarcinoma | 1.00 | — | 1.00 | — |
| Squamous cell | 0.79 | 0.37-1.68 | 0.81 | 0.37-1.79 |
| Other** | 1.07 | 0.36-3.18 | 0.89 | 0.28-2.76 |
| Smoking status | | | | |
| Never | 1.00 | — | 1.00 | — |
| Ever | 0.63 | 0.24-1.66 | 0.72 | 0.26-1.99 |

*Multivariable logistic regression model adjusted for stage (1A/1B), age (continuous), sex, race (C/AA), histology (adenocarcinoma, squamous cell, other), smoking status (ever/never)

Gene Methylation Predicts Risk of Recurrence in Tumor and Lymph Nodes

Methylation profiles using 7 genes were obtained on 727 of 731 paraffin blocks corresponding to 167 patients. The prevalence for methylation of four genes, p16, H-cadherin, RASSF1A and APC, especially in tumors and/or N2 lymph nodes, differed between cases and controls, as shown in Table 3.

TABLE 3

Table 2. Prevalence of Individual Gene Hypermethylation in Tumor, N1, and N2 Lymph Nodes in Recurrent Cases and Controls. (N = 167)

| Characteristics | Tumor Samples | | | N1 Lymph Node Samples | | | N2 Lymph Node Samples | | |
|---|---|---|---|---|---|---|---|---|---|
| | Control (n = 104) % | Case (n = 50) % | p-value* | Control (n = 82) % | Case (n = 41) % | p-value* | Control (n = 56) % | Case (n = 34) % | p-value* |
| MGMT Methylated | 36.1 | 34.7 | 0.87 | 29.5 | 37.5 | 0.38 | 35.8 | 44.1 | 0.44 |
| ASC Methylated | 34.9 | 38.8 | 0.65 | 27.2 | 29.3 | 0.81 | 42.9 | 44.1 | 0.91 |
| DAPK Methylated | 35.3 | 36.0 | 0.93 | 41.5 | 42.5 | 0.91 | 30.8 | 39.4 | 0.41 |
| APC Methylated | 34.0 | 36.0 | 0.81 | 18.7 | 13.5 | 0.48 | 13.0 | 29.4 | 0.06 |
| RASSF1A Methylated | 35.0 | 50.0 | 0.10 | 16.5 | 12.8 | 0.61 | 9.6 | 20.6 | 0.15 |
| P16 Methylated | 26.0 | 52.0 | <0.01 | 13.7 | 35.0 | <0.01 | 16.7 | 48.5 | <0.01 |
| H-Cadherin Methylated | 22.8 | 38.8 | 0.04 | 19.5 | 32.5 | 0.12 | 25.0 | 46.9 | 0.04 |

*Chi-squared test for homogeneity.

FIG. 1 shows multivariate logistic regression analysis that was performed using the four genes that exhibited the largest univariate distribution differences in methylation: p16, H-cadherin, APC, and RASSF1A. The prognostic value of each molecular variable was assessed in a model that adjusted for stage (1A/1B), age (continuous), sex, race (Caucasian/African American), histology (adenocarcinoma, squamous cell, other), smoking status (ever/never) and then graphed as a Forest Plot. On the whole, regardless of the genes considered, hypermethylation of the mediastinal lymph node tissue had the highest prognostic value for estimating lung cancer recurrence versus no methylation. As single gene epigenetic markers, methylation of both p16 and H-cadherin had robust odds ratios for recurrence for primary tumor, regional, and mediastinal lymph nodes. Methylation of either RASSF1A or APC in primary tumor or N2 nodes was also associated with a modest elevation in odds of recurrence but this was not statistically significant. If a patient with pathologic stage 1 disease (T1-2N0) had concomitant methylation of p16 as well as H-cadherin in both tumor and mediastinal lymph nodes, the estimated odds of lung cancer recurrence was over 15 as compared to those patients without concomitant methylation in these tissues. In particular, when either p16 or H-cadherin was methylated in the primary tumor, the adjusted odds of recurrence was 3.50 (95% CI, 1.65-7.41) and 2.12 (95% CI, 0.98-4.59), respectively (FIG. 1). When these same genes were methylated in N1 lymph nodes, the odds of recurrence was 3.62 (95% CI, 1.41-9.32) and 1.99 (95% CI, 0.81-4.88), respectively. If methylation of p16 or H-cadherin was observed in mediastinal lymph nodes, the odds of recurrence was increased to 4.67 (95% CI, 1.52-14.4) and 3.98 (95% CI, 1.22-13.0) fold, respectively, as shown in FIG. 1. Methylation of either RASSF1A or APC in primary NSCLC or N2 nodes was also associated with a modest elevation in risk for recurrence but this was not statistically significant (FIG. 1).

Two gene combinations of methylation, for p16 and H-cadherin, H-cadherin and APC, APC and p16, as well as RASSF1A and p16, all were associated with increased risks of recurrence, especially in either primary tumors or N2 nodes (FIG. 1). Concomitant methylation of the best gene combination, p16 and H-cadherin, was significantly associated with recurrent cancer in all three tissue types—primary tumor, N1, as well as N2 lymph nodes. If a patient exhibited methylation of p16 and H-cadherin in the primary tumor, the odds of recurrence was eight times higher than if there was no methylation. Even more striking, positive p16 and H-cadherin methylation in both paired primary tumors and mediastinal lymph nodes denotes an estimated odds of recurrent cancer of 15.5 (95% CI, 1.61-185) (FIG. 1), with a positive predictive value of 86%.

The above findings were re-tested for methylation of the 4-gene panel by assaying the methylation status of these genes in a validation set. 162 separate samples were obtained, representing an independent set of 20 stage 1 patients (11 cases and 9 controls) resected at a later date at the Johns Hopkins Hospital ("the institution"), as shown in Table 1, above.

FIG. 2 shows Kaplan-Meier Estimates of Recurrence-Free Survival of Pathologic Stage 1 Lung Cancer Patients (n=167) at the Johns Hopkins Hospital, according to the number of methylated genes in a 4-gene panel at the time of surgical resection. The Kaplan-Meier estimates for time to recurrence indicate that for both tumor as well as for regional (N1) and mediastinal (N2) lymph nodes, as the number of methylated genes in the panel increases, there is a significant reduction in the recurrence-free survival (Panels A-C, E-G). Furthermore, if concomitant methylation of both tumor and mediastinal lymph nodes versus little or no methylation is considered (Panels D and H), the Kaplan-Meier estimates reflect the recurrence-free survivals of patients with a clinically useful risk classification system as determined by our epigenetic marker panel. Patients without methylation of the gene combination p16 and H-cadherin in both primary tumor and mediastinal lymph nodes have a significantly improved 5 year recurrence-free period than those with these genes methylated (64% vs. 14%, p<0.001, respectively, Panel H). An independent cohort of 20 patients validated the above findings as those with concomitant methylation of both tumor and mediastinal lymph nodes in two or more genes had a shorter time to recurrence than those with two or more genes unmethylated in these tissues (Panel I). Similarly, concomitant methylation of p16 and H-cadherin in tumors and N2 nodes resulted in a worse 5 year disease-free recurrence than if no methylation of this gene combination occurred (Panel J). In the combined original and validation datasets (n=187), patients with 2 or more genes in tumor and N2 nodes methylated also have a worse 5 year recurrence rate than those with these genes unmethylated in both tissues (Panel K). For both the original and validation patients with p16 and H-cadherin measured, both genes methylated in the tumor and N2 nodes resulted in a significantly shorter time to recurrence than if p16 and H-cadherin were unmethylated (Panel L). As was the case with the original cohort, univariate and multivariate analysis showed that methylation of the panel of genes in both tumor and lymph nodes was more predictive of disease recurrence than any clinical or pathological variable (FIG. 2: Panels I and J). In particular, positive p16 and H-cadherin methylation in both paired primary tumors and mediastinal lymph nodes occurred in 4 cases and no controls yielding an infinite odds of recurrent disease reflected in FIG. 2, Panel J. This finding strongly supports the original finding of an elevated odds ratio for recurrence when p16 and H-cadherin methylation is found in these tissues (FIG. 1). Moreover, the estimated odds of recurrent cancer for the original and validation datasets combined, for this gene combination when found in both tumor and N2 nodes, increased to 25.25 (95% CI, 2.53-252.35). This is shown in Table 4, below.

TABLE 4

Table 3. Multivariate Odds Ratios (OR) and 95% Confidence Limits (95% CL) for Estimation of Risk of Recurrance by Methylation Status for Selected Gene Markers

|  | Gene Marker | Original (n = 167) OR | 95% CL | Original and Validation (n = 187) OR* | 95% CL |
|---|---|---|---|---|---|
| Single Genes | Unmethylated APC | 1.00 | referent | 1.00 | referent |
|  | Tumor | 0.95 | 0.45-2.04 | 1.31 | 0.67-2.58 |
|  | N1 | 0.69 | 0.22-2.10 | 0.78 | 0.32-1.91 |
|  | N2 | 2.26 | 0.66-7.71 | 1.87 | 0.65-5.56 |
|  | Tumor and N2 | 2.37 | 0.52-10.83 | 2.00 | 0.55-7.33 |
|  | RASSF1A |  |  |  |  |
|  | Tumor | 1.79 | 0.85-3.75 | 1.86 | 0.94-3.68 |
|  | N1 | 0.71 | 0.23-2.20 | 0.82 | 0.31-2.15 |
|  | N2 | 1.66 | 0.43-6.43 | 2.13 | 0.65-6.95 |
|  | Tumor and N2 | 0.66 | 0.11-3.88 | 0.97 | 0.23-3.98 |
|  | P16 |  |  |  |  |
|  | Tumor | 3.50 | 1.55-7.41 | 3.55 | 1.77-7.13 |
|  | N1 | 3.62 | 1.41-9.32 | 4.14 | 1.81-9.49 |
|  | N2 | 4.67 | 1.53-14.42 | 5.09 | 1.95-13.18 |
|  | Tumor and N2 | 5.23 | 1.33-20.46 | 8.41 | 2.42-29.20 |
|  | HCAD |  |  |  |  |
|  | Tumor | 2.12 | 0.98-4.59 | 2.33 | 1.16-4.69 |
|  | N1 | 1.99 | 0.81-4.88 | 2.67 | 1.25-5.93 |
|  | N2 | 3.98 | 1.22-13.01 | 4.04 | 1.53-13.63 |
|  | Tumor and N2 | 6.89 | 1.36-34.87 | 7.55 | 1.99-28.60 |
| Gene Combinations | APC & RASSF1A |  |  |  |  |
|  | Tumor | 1.88 | 0.74-4.78 | 2.25 | 1.02-5.00 |
|  | N1 | 1.22 | 0.15-14.53 | 2.34 | 0.46-11.75 |
|  | N2 | — | — | 3.49 | 0.30-40.75 |
|  | Tumor and N2** | — | — | 2.37 | 0.17-33.12 |
|  | APC & P16 |  |  |  |  |
|  | Tumor | 4.16 | 1.60-10.81 | 4.48 | 1.91-10.51 |
|  | N1 | 2.59 | 0.34-19.74 | 2.43 | 0.59-9.94 |
|  | N2 | 13.10 | 1.20-142.73 | 7.45 | 1.35-41.20 |
|  | Tumor and N2 | 5.27 | 0.38-73.57 | 7.70 | 0.70-84.88 |
|  | APC & HCAD |  |  |  |  |
|  | Tumor | 1.54 | 0.55-4.31 | 2.14 | 0.94-4.91 |
|  | N1 | 2.24 | 0.41-12.22 | 3.30 | 0.88-12.40 |
|  | N2 | 4.58 | 1.50-20.01 | 3.13 | 0.89-11.01 |
|  | Tumor and N2 | 11.79 | 0.85-163.24 | 9.48 | 0.87-103.18 |
|  | RASSF1A & P16 |  |  |  |  |
|  | Tumor | 5.95 | 2.15-16.56 | 5.26 | 2.13-13.00 |
|  | N1 | 1.07 | 0.15-7.56 | 1.92 | 0.39-9.45 |
|  | N2 | 3.01 | 0.49-18.64 | 4.60 | 0.85-25.03 |
|  | Tumor and N2 | 2.91 | 0.24-35.35 | 3.67 | 0.32-41.69 |
|  | RASSF1A & HCAD |  |  |  |  |
|  | Tumor | 1.61 | 0.69-3.89 | 1.71 | 0.78-3.74 |
|  | N1 | 0.49 | 0.09-2.63 | 0.88 | 0.25-3.04 |
|  | N2 | 1.36 | 0.22-8.48 | 1.91 | 0.40-9.21 |
|  | Tumor and N2 | 2.49 | 0.18-34.29 | 3.51 | 0.32-38.57 |
|  | P16 & HCAD |  |  |  |  |
|  | Tumor | 8.00 | 2.50-25.51 | 6.71 | 2.50-18.00 |
|  | N1 | 4.08 | 1.06-15.70 | 6.13 | 1.99-18.89 |
|  | N2 | 4.32 | 1.06-17.65 | 4.66 | 1.53-14.16 |
|  | Tumor and N2 | 15.50 | 1.61-185.02 | 25.25 | 2.53-252.35 |

*Multivariate logistic regression model adjusted for stage (1A/15) age (continuous), sex, race (C/AA), histology (adenecarcinoma, squamous cell, other), smoking status (ever/never).
**No methylation in controls.

Example 3: Tumor Biology and Translational Implications

An observation is that, among those 51 patients in the cohort who recurred, the presence of methylation in more than two genes in paired primary tumors and mediastinal lymph nodes identifies those who recur early versus those cases without markers that recur late (9 months (range 5-30) vs. 25 months (range 6-40); p≤0.04). Thus, those who lack these epigenetic marks recur late and appear to behave similarly to control patients who do not have recurrences within the 40 month time frame studied, as is reflected in the various risk for recurrence curves shown in FIG. 2.

Second, estimates of time to recurrence indicate that for both cases and controls, as the number of methylated genes in the 4-gene panel increases in primary tumor, regional and mediastinal lymph nodes, there is a significant reduction in recurrence-free survival (FIG. 2: Panels A-C, E-G). Moreover, if concomitant methylation of both tumor and mediastinal lymph nodes is considered (Panels D and H), the prognostic value of the epigenetic markers is further increased. In Panels D and H, the recurrence estimates of the stage 1 subjects with ≥2 genes methylated reflect the historic cancer-specific survivals of patients who would be pathologically staged as stage 3 or higher (5). In the original cohort, those patients with the combination of p16 and H-cadherin methylation in tumor and mediastinal lymph nodes have a significantly reduced 5-year recurrence-free survival compared to those without methylation (64% vs. 14%, p<0.001, respectively). This finding also emerged in the small validation study of 20 patients as shown in FIG. 2, panel J. Moreover, patients in the validation set with ≥2 genes methylated in tumor and mediastinal lymph nodes have significantly reduced 5-year recurrence-free survivals compared to those without methylation (FIG. 2, panel I). Thus, when the original and validation datasets are combined, the methylation status for these parameters is now even more strongly prognostic of disease-free survival (FIG. 2, panels K and L).

In the entire study population including the original and validation patients, 91 individuals, 50 controls and 41 cases, had p16 and H-cadherin methylation measured in both primary tumor and N2 lymph nodes. Of those patients who were positive for both markers in both sites, 10 of 11 were cases. All 10 had disease recurrence within 30 months, 9 within 17 months, and 8 within a year. Thus, the methylation status of p16 and H-cadherin in tumor and N2 nodal DNA, appears to identify a subset, 25%, of stage 1 patients with a likelihood of rapid disease recurrence with a positive predictive value of 91% and a specificity of 98%.

The results presented herein demonstrate two related features for the detection of promoter region methylation in cancer. First, the detection of promoter methylation within the resected primary tumor for key genes can be associated with a more aggressive, recurrent phenotype as has been shown in other settings (28,29). The loss of function in key regulatory genes for cell cycle control (p16), invasion and metastasis (H-Cadherin, APC), as well as Ras signaling (RASSF1a) might be expected to result in a more aggressive primary tumor. In addition, the ability to detect methylation within local or regional nodes provides a second layer of information to this subset identification, and demonstrates an additional approach for detecting micrometastatic disease.

The data presented herein demonstrate that this approach may be used to identify aggressive stage 1 lung cancer patients who were not staged optimally by routine pathological analysis. The current staging system for NSCLC is imprecise, and in stage 1 (T1-2N0) disease, in particular, the clinicopathologic criteria understages patients. The results presented herein show that gene promoter methylation detection within NSCLC primary tumors can be used to identify cells with high potential for metastatic spread, and also to detect histologically occult micrometastases in lymph nodes used to stage NSCLC. Although it is possible that the methylation detected could represent free tumor DNA that has drained from the primary tumor via lymphatics, this is unlikely, particularly for N2 nodes, since these are located distant from the lung in a separate body compartment, the mediastinum. While the detection of methylation of these genes in tumor or N1 nodes was often associated with increased risk of recurrence, in the N2 lymph nodes, especially, the markers were very strongly prognostic, strengthening the contention that the DNA methylation is detecting micrometastatic disease. This molecular distribution of markers in patients with rapid recurrence mirrors the biological basis of current histological staging systems that identify intact tumor cells that have traversed the mediastinal pleura to the N2 nodes and are associated with increased risk of recurrence.

The methods described herein present a molecular tool that parallels the use of histologic examination in accepted clinical pathology practice, but is more sensitive. This differs from previous studies that have relied solely on molecular characteristics of the primary malignancy (30-33). This ability to utilize the predictive power inherent in identifying micrometastases to lymph nodes may allow a more robust and reliable molecular staging built upon tumor characteristics and the detection of micrometastatic disease. Furthermore, recent promising results from examining methylation changes in sputum for predicting risk of lung cancer (34), or its recurrence (18), means the detection of these changes could provide valuable pre-surgical information as to disease stage and the metastatic potential of a patient's tumor.

Methods

The invention was carried out using methods that include the following.

Patients

Evidence for recurrent disease was evaluated on 715 pathologically proven stage 1 (T1-2N0) patients diagnosed with non-small cell lung carcinoma (NSCLC) (International Classification of Diseases-ninth revision-Clinical Modification [ICD-9-CM] code 162.3-162.9) who underwent lobectomy or greater resections at the Johns Hopkins Hospital between Jan. 1, 1986 and Jul. 31, 2002. Only patients followed for recurrent disease at the institution were eligible for the analysis. The study cohort consisted of 71 patients (cases) who despite receiving surgery with curative intent for pathological stage 1 (T1-2N0) primary NSCLC, recurred at the institution within 40 months of surgery and died of their cancer. It was estimated that by 40 months approximately 80% of patients with resected stage 1 lung cancer would recur. Using patient age, stage, date of surgery (within 5 years), and sex, the cases were matched to 158 stage 1 patients (controls) from the remainder of the study population. These 71 cases and 158 controls formed the basic case-control population. From the above patients, samples were gathered for methylation analysis for 51 cases and 116 matched controls. Neither cases nor controls received adjuvant chemotherapy since surgery was performed between 1986-2002 when guidelines did not recommend adjuvant therapy for stage 1B patients (20, 21). All patients were staged according to the new TNM classification criteria (5), which include histological status of mediastinal lymph nodes sampled from levels 2, 4, 7, 8, 9, and 10 on the right, and 5, 6, 7, 8, 9 on the left side. Regional lymph nodes, confined to the pleural space, were resected en bloc with the tumor. Patients were excluded as cases if they had surgery involving less than a lobectomy because there is strong evidence that patients with such resections are at significantly increased risk of local recurrence (22). Patients were also excluded as cases if they had any macroscopic or microscopically positive surgical margins, or underwent incomplete resection. In accord with this nested design, seven individuals with recurrences after 40 months postoperatively were considered as controls. The 20 patients in the validation set, consisting of 11 cases and 9 matched controls, had 162 paraffin blocks evaluated. All cases in the independent validation cohort, except for two, underwent resection at our institution after August 2002. The study was approved by the Institutional Review Board of the Johns Hopkins Medical Institutions.

Preparation of Tumor and Lymph Nodes

All specimens were labeled only with study-specific coded identifiers to blind laboratory investigators as to case or control status as well as to whether DNA samples came from tumor or lymph nodes. DNA was extracted from three sequential 10 μm sections from unstained, paraffin embedded slides of resected tumors and lymph nodes (both N1 and N2). For each sample, adjacent sections were H&E stained for histological confirmation of either the presence of malignancy for tumor samples, or the lack of neoplastic cells for all lymph nodes. Tumor grading was at the time of surgery. Unstained tissue sections were deparaffinized and DNA was extracted as described previously 23. DNA was quantified spectrophotometrically, and 1 μg was denatured with sodium hydroxide and modified with sodium bisulfite. Samples were then purified with the Wizard DNA purification resin (Promega, Madison, Wis.), treated again with sodium hydroxide, precipitated with ethanol, and resuspended in water.

Methylation Specific PCR (MSP)

DNA methylation, for all lung cancer and lymph node DNA, was determined by MSP performed by 3 individuals blinded to the results of other investigators. Each individual extracted DNA and performed all steps of the MSP reaction separately. There were 889 total samples of tumor and lymph nodes examined. A multiplex-nested MSP assay as previously described was used for all samples 24. The nested approach amplifies bisulfite-modified DNA initially with flanking PCR primers without preferentially amplifying methylated or unmethylated DNA. The resulting fragment is then used as the template for MSP. Primer sequences and conditions of p16, MGMT, DAPK, RASSF1A, H-cadherin, ASC and APC have all been previously described 16, 18, 24-26 including conditions optimized to achieve specific detection of methylation in tumor but not in normal lymphocytes, and are shown in Table 5, below (16, 18, 24-26).

TABLE 5

Supplemental Table 1: METHYLATED SPECIFIC PCR CONDITIONS USED

FRANK PCR for APC, MGMT, ASC, P16, DARK, H-CADHERIN, RASSF1A:
Using 1:500 diluted Flank PCR product as the PCR templates:

| | |
|---|---|
| 95° C. 5 Min | 1 cycle |
| 95° C. 30 Sec | |
| 55° C. 30 Sec | |

TABLE 5-continued

Supplemental Table 1: METHYLATED SPECIFIC PCR CONDITIONS USED

| | |
|---|---|
| 72° C. 40 Sec | 36 cycles |
| 72° C. 5 Min | 1 cycle |
| INSIDE PCR for APC, MGMT, DAPK, RASSF1A | |
| 95° C. 5 Min | 1 cycle |
| 95° C. 30 Sec | |
| 60° C. 30 Sec | |
| 72° C. 30 Sec | 25 cycles |
| 72° C. 5 Min | 1 cycle |
| INSIDE FOR P16: | |
| 95° C. 5 Min | 1 cycle |
| 95° C. 30 Sec | |
| 64° C. 30 Sec | |
| 72° C. 30 Sec | 20 cycles |
| 72° C. 5 Min | 1 cycle |
| INSIDE FOR ASC: | |
| 95° C. 5 Min | 1 cycle |
| 95° C. 30 Sec | |
| 66° C. 30 Sec | |
| 72° C. 30 Sec | 20 cycles |
| 72° C. 5 Min | 1 cycle |
| INSIDE for H-CADHERIN: | |
| 95° C. 5 Min | 1 cycle |
| 95° C. 30 Sec | |
| 64° C. 30 Sec | |
| 72° C. 30 Sec | 30 cycles |
| 72° C. 5 Min | 1 cycle |

Figure 3:
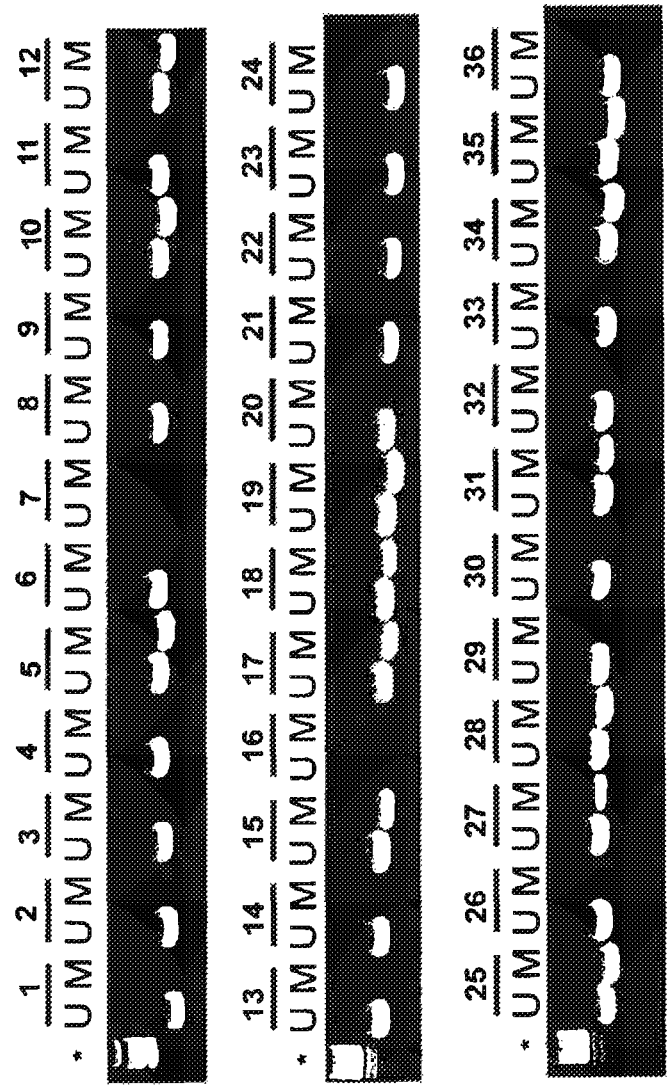
FIG. 3 shows Methylation Specific PCR for the H-cadherin gene. For each sample, the presence of a visible PCR product in Lanes marked U indicates the presence of an unmethylated promoter region amplified and serves as a control for sample preparation; the presence of product in Lanes M indicates a methylated gene promoter and was scored as positive for methylation. * represents the molecular weight marker.

FIG. 3 shows methylation specific PCR for the H-cadherin gene in 36 samples of tumors and lymph nodes, numbered at top of each panel. * represents the molecular weight marker. For each sample, the presence of a visible PCR product in Lanes U indicates the presence of an unmethylated promoter region amplified and serves as a control for sample preparation; the presence of product in Lanes M indicates a methylated gene promoter and was scored as positive for methylation. Samples 7 and 16 did not amplify for this gene. Samples 1, 2, 3, 4, 8, 9, 11, 13, 14, 20, 21, 22, 23, 26, 30, 32, 33, 36 are scored as unmethylated. Samples 5, 10, 12, 15, 17, 18, 19, 25, 27, 28, 31, 34, and 35 are methylated and samples 24 and 29 had very minimal M amplification that was scored as negative. Placental DNA treated in vitro with SssI methyltransferase (New England Biolabs, Beverly, Mass.) was used as a positive control. DNA from normal lymphocytes and water (bisulfite-modified and unmodified water) were used as negative controls. PCR products were visualized using 2% agarose or 6% nondenaturing polyacrylamide gels, and visually scored as methylated or unmethylated according to the presence or absence of a PCR product (FIG. 3), blinded to both the clinical outcomes and sources of DNA. (9, 25, 27).

Statistical Methods

Histopathological results and reports of events (death, or recurrent disease) were verified during follow-up by reexamining original hospital paper and electronic records. The primary endpoint was recurrent disease (including local, regional, and distant recurrences), measured from the date of surgery to cancer-related death or censor. Control subjects who were alive and had no evidence of disease at the end of study were censored for recurrence and death. All deaths were cancer-related and no subjects were lost to follow-up. The association between prognostic factors and recurrence (case vs. control) was assessed using univariable and multivariable logistic regression. Results of all models are reported as relative risks with 95% confidence intervals (Stata Statistical Software, College Station, Tex.). Associations were considered to be significant when P was <0.05 (two-sided).

It was hypothesized that 40 percent or more of the cases would have positive microscopic disease in their lymph nodes. For controls, this number was expected to be less than or equal to 20 percent, yielding a risk ratio of 2. Under these assumptions, the study would have 80 percent power to detect the effect as statistically significant (two-sided 0.05 alpha level test) with 167 subjects and 2:1 matching.

The present invention has been described in detail, including the preferred embodiments thereof. However, it will be appreciated that those skilled in the art, upon consideration of the present disclosure, may make modifications and/or improvements of this invention and still be within the scope and spirit of this invention as set forth in the following claims.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

REFERENCES

1. Hellman S. Stopping metastases at their source. N Engl J Med 1997; 337:996-7.
2. Riethmuller G, Johnson J P. Monoclonal antibodies in the detection and therapy of micrometastatic epithelial cancers. Curr Opin Immunol 1992; 4:647-55.
3. Zhu J J, Maruyama T, Jacoby L B, et al. Clonal analysis of a case of multiple meningiomas using multiple molecular genetic approaches: pathology case report. Neurosurgery 1999; 45:409-16.
4. Martini N, Bains M S, Burt M E, et al. Incidence of local recurrence and second primary tumors in resected stage I lung cancer. J Thorac Cardiovasc Surg 1995; 109:120-9.
5. Mountain C F. Revisions in the International System for Staging Lung Cancer. Chest 1997; 111:1710-7.
6. Hoffman P C, Mauer A M, Vokes E E. Lung cancer. Lancet 2000; 355:479-85.
7. Herman J G, Baylin S B. Gene silencing in cancer in association with promoter hypermethylation. N Engl J Med 2003; 349:2042-54.
8. Baylin S B, Ohm J E. Epigenetic gene silencing in cancer—a mechanism for early oncogenic pathway addiction? Nat Rev Cancer 2006; 6:107-16.
9. Herman J G, Graff J R, Myohanen S, Nelkin B D, Baylin S B. Methylation-specific PCR: a novel PCR assay for methylation status of CpG islands. Proc Natl Acad Sci USA 1996; 93:9821-6.
10. Esteller M, Corn P G, Baylin S B, Herman J G. A gene hypermethylation profile of human cancer. Cancer Res 2001; 61:3225-9.
11. Pellise M, Castells A, Gines A, et al. Detection of lymph node micrometastases by gene promoter hypermethylation in samples obtained by endosonography-guided fine-needle aspiration biopsy. Clin Cancer Res 2004; 10:4444-9.
12. Sanchez-Cespedes M, Esteller M, Hibi K, et al. Molecular detection of neoplastic cells in lymph nodes of metastatic colorectal cancer patients predicts recurrence. Clin Cancer Res 1999; 5:2450-4.
13. Kollermann J, Muller M, Goessl C, et al. Methylation-specific PCR for DNA-based detection of occult tumor cells in lymph nodes of prostate cancer patients. Eur Urol 2003; 44:533-8.
14. Harden S V, Tokumaru Y, Westra W H, et al. Gene promoter hypermethylation in tumors and lymph nodes of stage I lung cancer patients. Clin Cancer Res 2003; 9:1370-5.
15. Belinsky S A, Nikula K J, Palmisano W A, et al. Aberrant methylation of p16(INK4a) is an early event in lung cancer and a potential biomarker for early diagnosis. Proc Natl Acad Sci USA 1998; 95:11891-6.
16. Toyooka K O, Toyooka S, Virmani A K, et al. Loss of expression and aberrant methylation of the CDH13 (H-cadherin) gene in breast and lung carcinomas. Cancer Res 2001; 61:4556-60.
17. Toyooka S, Toyooka K O, Maruyama R, et al. DNA methylation profiles of lung tumors. Mol Cancer Ther 2001; 1:61-7.
18. Machida E O, Brock M V, Hooker C M, et al. Hypermethylation of ASC/TMS1 is a sputum marker for late-stage lung cancer. Cancer Res 2006; 66:6210-8.
19. Brock M V, Kim M P, Hooker C M, et al. Pulmonary resection in octogenarians with stage I nonsmall cell lung cancer: a 22-year experience. Ann Thorac Surg 2004; 77:271-7.
20. Ettinger D S, Cox J D, Ginsberg R J, et al. NCCN Non-Small-Cell Lung Cancer Practice Guidelines. The National Comprehensive Cancer Network. Oncology (Williston Park) 1996; 10:81-111.
21. Johnson B E. NCCN: Small cell lung cancer. Cancer Control 2001; 8:32-43.
22. Ginsberg R J, Rubinstein L V. Randomized trial of lobectomy versus limited resection for T1 N0 non-small cell lung cancer. Lung Cancer Study Group. Ann Thorac Surg 1995; 60:615-22; discussion 622-3.
23. House M G, Guo M, Efron D T, et al. Tumor suppressor gene hypermethylation as a predictor of gastric stromal tumor behavior. J Gastrointest Surg 2003; 7:1004-14; discussion 1014.
24. van Engeland M, Weijenberg M P, Roemen G M, et al. Effects of dietary folate and alcohol intake on promoter methylation in sporadic colorectal cancer: the Netherlands cohort study on diet and cancer. Cancer Res 2003; 63:3133-7.
25. Guo M, Ren J, House M G, Qi Y, Brock M V, Herman J G. Accumulation of promoter methylation suggests epigenetic progression in squamous cell carcinoma of the esophagus. Clin Cancer Res 2006; 12:4515-22.
26. van Engeland M, Roemen G M, Brink M, et al. K-ras mutations and RASSF1A promoter methylation in colorectal cancer. Oncogene 2002; 21:3792-5.
27. Esteller M, Garcia-Foncillas J, Andion E, et al. Inactivation of the DNA-repair gene MGMT and the clinical response of gliomas to alkylating agents. N Engl J Med 2000; 343:1350-4.
28. Brock M V, Gou M, Akiyama Y, et al. Prognostic importance of promoter hypermethylation of multiple genes in esophageal adenocarcinoma. Clin Cancer Res 2003; 9:2912-9.
29. Tang X, Khuri F R, Lee J J, et al. Hypermethylation of the death-associated protein (DAP) kinase promoter and aggressiveness in stage I non-small-cell lung cancer. J Natl Cancer Inst 2000; 92:1511-6.
30. Potti A, Mukherjee S, Petersen R, et al. A genomic strategy to refine prognosis in early-stage non-small-cell lung cancer. N Engl J Med 2006; 355:570-80.

31. Brundage M D, Davies D, Mackillop W J. Prognostic factors in non-small cell lung cancer: a decade of progress. Chest 2002; 122:1037-57.
32. Chen H Y, Yu S L, Chen C H, et al. A five-gene signature and clinical outcome in non-small-cell lung cancer. N Engl J Med 2007; 356:11-20.
33. Gu J, Berman D, Lu C, et al. Aberrant promoter methylation profile and association with survival in patients with non-small cell lung cancer. Clin Cancer Res 2006; 12:7329-38.
34. Belinsky S A, Liechty K C, Gentry F D, et al. Promoter hypermethylation of multiple genes in sputum precedes lung cancer incidence in a high-risk cohort. Cancer Res 2006; 66:3338-44.
35. Gore S D, Baylin S, Sugar E, et al. Combined DNA methyltransferase and histone deacetylase inhibition in the treatment of myeloid neoplasms. Cancer Res 2006; 66:6361-9.
36. Fearon, et al., Cell, 61:759, 1990.
37. Jones, et al., Cancer Res., 46:461, 1986.
38. Baylin, et al., Cancer Cells, 3:383, 1991.
39. Saiki, et al., Bio/Technology, 3:1008-1012, 1985.
40. Conner, et al., Proc. Natl. Acad. Sci. USA, 80:278, 1983.
41. Landegren, et al., Science, 241:1077, 1988.
42. Landegren, et al., Science, 242:229-237, 1988.
43. Mansour et al., 1989, N. Engl. J. Med. 320: 485-490.

What is claimed is:

1. A method for treating non-small cell lung cancer metastases in a human subject consisting of:
   a) obtaining a biological sample from a human subject, wherein the biological sample is a lung tumor tissue sample, a regional lymph node or a mediastinal lymph node;
   b) isolating genomic DNA from the biological sample;
   c) contacting the isolated genomic DNA with bisulfite to transform unmethylated cytosines in the genomic DNA to uracil;
   d) PCR amplifying the transformed genomic DNA of the p16 gene encoding SEQ ID NO: 2 and the H-cadherin gene encoding SEQ ID NO: 1 using primers consisting of: (i) a pair of methylation primers specific for p16 and a pair of methylation primers specific for H-cadherin genes and (ii) a pair of unmethylated primers specific for p16 and a pair of unmethylated primers specific for H-cadherin genes;
   e) detecting methylation of genomic p16 and H-cadherin DNA;
   f) diagnosing non-small cell lung cancer metastases in the human subject; and
   g) administering a therapeutically effective amount of a demethylating agent to the human_subject diagnosed as having non-small cell lung cancer metastases, thereby treating the non-small cell lung cancer metastases.

2. The method of claim 1, wherein the non-small cell lung cancer metastases are micrometastases.

3. A method for treating a recurrence of a non-small cell lung cancer (NSCLC) in a human subject consisting of:
   a) obtaining a biological sample from a human subject to be treated, wherein the biological sample is a lung tumor tissue sample, a regional lymph node or a mediastinal lymph node;
   b) isolating genomic DNA from the biological sample;
   c) contacting the isolated genomic DNA with bisulfite to transform unmethylated cytosines in the genomic DNA to uracil;
   d) PCR amplifying the transformed genomic DNA of the p16 gene encoding SEQ ID NO: 2 and the H-cadherin gene encoding SEQ ID NO: 1 using primers consisting of: (i) a pair of methylation primers specific for p16 and a pair of methylation primers specific for H-cadherin genes and (ii) a pair of unmethylated primers specific for p16 and a pair of unmethylated primers specific for H-cadherin genes;
   e) detecting methylation of genomic p16 and H-cadherin DNA;
   f) diagnosing non-small cell lung cancer metastases in the human subject; and
   g) administering a therapeutically effective amount of a demethylating agent to the human_subject diagnosed as having non-small cell lung cancer metastases, thereby treating the recurrence of NSCLC in the human subject.

4. A method for treating recurrence of non-small cell lung cancer (NSCLC) metastases in a human subject consisting of:

a) obtaining a biological sample from a human subject to be treated, wherein the biological sample is a lung tumor tissue sample, a regional lymph node or a mediastinal lymph node;
b) providing a kit having bisulfite and methylation specific PCR primers for detecting a hypermethylation state of a p16 gene encoding SEQ ID NO: 2 and the H-cadherin gene encoding SEQ ID NO: 1;
c) contacting the biological sample with the bisulfite from the kit to transform unmethylated cytosines in the genomic DNA in the biological sample to uracil;
d) PCR amplifying the transformed genomic DNA with the methylation specific PCR primers in the kit to detect nucleic acid methylation of the p16 gene and the H-cadherin gene in the lung tumor tissue sample, a regional lymph node or a mediastinal lymph node in the transformed genomic DNA;
   Wherein the methylation specific PCR primers are specific for bisulfite transformed unmethylated cytosines;
e) detecting methylation of genomic p16 and H-cadherin DNA;
f) diagnosing non-small cell lung cancer metastases in the human subject; and
g) administering a therapeutically effective amount of a demethylating agent to the human_subject diagnosed as having non-small cell lung cancer metastases, thereby treating the recurrence of NSCLC in the human subject.

* * * * *